(12) United States Patent
Futase

(10) Patent No.: US 12,422,429 B2
(45) Date of Patent: *Sep. 23, 2025

(54) METHODS FOR REDUCING NOISE IN SIGNAL-GENERATING DIGITAL ASSAYS

(71) Applicant: ABBOTT JAPAN LLC, Tokyo (JP)

(72) Inventor: Atsuko Futase, Tokyo (JP)

(73) Assignee: ABBOTT JAPAN LLC, Tokyo (JP)

( * ) Notice: Subject to any disclaimer, the term of this patent is extended or adjusted under 35 U.S.C. 154(b) by 1176 days.

This patent is subject to a terminal disclaimer.

(21) Appl. No.: 17/313,978

(22) Filed: May 6, 2021

(65) Prior Publication Data

US 2021/0333271 A1    Oct. 28, 2021

Related U.S. Application Data

(63) Continuation of application No. 15/888,952, filed on Feb. 5, 2018, now Pat. No. 11,047,854.

(60) Provisional application No. 62/455,436, filed on Feb. 6, 2017.

(51) Int. Cl.
*G01N 33/543* (2006.01)

(52) U.S. Cl.
CPC . *G01N 33/54373* (2013.01); *G01N 33/54306* (2013.01); *G01N 33/54393* (2013.01)

(58) Field of Classification Search
CPC ....... G01N 33/54373; G01N 33/54306; G01N 33/54393
See application file for complete search history.

(56) References Cited

U.S. PATENT DOCUMENTS

| | | | |
|---|---|---|---|
| 5,026,159 A | 6/1991 | Allen et al. | |
| 5,162,990 A | 11/1992 | Odeyale et al. | |
| 5,481,401 A | 1/1996 | Kita et al. | |
| 5,501,952 A | 3/1996 | Cubbage et al. | |
| 5,620,850 A | 4/1997 | Bamdad et al. | |
| 5,811,312 A | 9/1998 | Hasegawa et al. | |
| 5,880,473 A | 3/1999 | Ginestet | |
| 6,169,816 B1 | 1/2001 | Ravkin | |
| 6,259,807 B1 | 7/2001 | Ravkin | |
| 6,266,459 B1 | 7/2001 | Walt et al. | |
| 6,385,272 B1 | 5/2002 | Takahashi | |
| 7,050,613 B2 | 5/2006 | Murao et al. | |
| 7,070,921 B2 | 7/2006 | Huang et al. | |
| 7,272,252 B2 | 9/2007 | De La Torre-Bueno et al. | |
| 7,602,952 B2 | 10/2009 | Kersey et al. | |
| 7,838,250 B1 | 11/2010 | Goix et al. | |
| 7,843,634 B2 | 11/2010 | Kawahito | |
| 8,031,918 B2 | 10/2011 | Roth | |
| 8,304,026 B2 | 11/2012 | Smith et al. | |
| 8,460,879 B2 | 6/2013 | Walt et al. | |
| 8,704,196 B2 | 4/2014 | Wolleschensky et al. | |
| 8,759,790 B2 | 6/2014 | Kishima et al. | |
| 8,791,427 B2 | 7/2014 | Honda et al. | |
| 8,912,007 B2 | 12/2014 | Bjornson et al. | |
| 9,046,516 B2 | 6/2015 | Tsuchiya et al. | |
| 9,110,306 B2 | 8/2015 | Hayashi et al. | |
| 9,224,031 B2 | 12/2015 | Glensbjerg et al. | |
| 9,310,302 B2 | 4/2016 | Garsha et al. | |
| 2003/0096302 A1 | 5/2003 | Yguerabide | |
| 2003/0151735 A1 | 8/2003 | Blumenfeld et al. | |
| 2005/0083536 A1 | 4/2005 | Fouquet | |
| 2005/0118584 A1 | 6/2005 | Nomura | |
| 2006/0121544 A1 | 6/2006 | Boge et al. | |
| 2006/0154303 A1 | 7/2006 | Myogadani | |
| 2007/0141645 A1 | 6/2007 | Okamura et al. | |
| 2007/0263210 A1 | 11/2007 | Taguchi et al. | |
| 2008/0032324 A1 | 2/2008 | Walt et al. | |
| 2008/0240543 A1 | 10/2008 | Budach et al. | |
| 2008/0254492 A1 | 10/2008 | Tsuchiya et al. | |
| 2009/0015831 A1 | 1/2009 | Yguerabide | |
| 2009/0021735 A1 | 1/2009 | Shigeura | |
| 2009/0315987 A1 | 12/2009 | Straus | |
| 2010/0228513 A1 | 9/2010 | Roth et al. | |
| 2011/0195852 A1 | 8/2011 | Walt et al. | |
| 2011/0236964 A1 | 9/2011 | Oldham | |

(Continued)

FOREIGN PATENT DOCUMENTS

| | | |
|---|---|---|
| EP | 2369325 A1 | 9/2011 |
| JP | 3727026 | 12/2005 |

(Continued)

OTHER PUBLICATIONS

Banta et al., "Replacing antibodies: engineering new binding proteins." Annu Rev Biomed Eng. 2013; 15:93-113.

Behar et al., "Tolerance of the archaeal Sac7d scaffold protein to alternative library designs: characterization of anti-immunoglobulin G Affitins." Protein Eng Des Sel. Apr. 2013,26(4):267-75.

Chang et al., "Single molecule enzyme-linked immunosorbent assays: Theoretical considerations." Journal of Immunological Methods 378 (2012), 102-115.

Esparza et al., "Amyloid-Beta Oligomerization in Alzheimer Dementia versus High-Pathology Controls." American Neurological Association 2012, 73:104-107.

Gilbreth & Koide, "Structural insights for engineering binding proteins based on non-antibody scaffolds." Curr Opin Struct Biol. Aug. 2012;22(4):413-20.

(Continued)

*Primary Examiner* — Changhwa J Cheu
(74) *Attorney, Agent, or Firm* — Lisa Mueller; Casimir Jones

(57) ABSTRACT

Methods of reducing background noise in signal-generating digital assays, such as fluorescent digital immunoassays, using a colorant are disclosed. The methods utilize a binding member that specifically binds to an analyte in a biological sample. The binding member is conjugated to a signal generating compound, e.g., an enzyme, which is dissociated from the binding member. A colorant is added with a signal generating substrate, e.g., a fluorogenic or chromogenic substrate for the enzyme, or after a signal generating substrate to reduce background noise in a fluorescent digital immunoassay. The signal generated between the signal generating compound and the signal generating substrate is detected and correlated to the presence and/or concentration of the analyte.

31 Claims, 14 Drawing Sheets

(56) References Cited

U.S. PATENT DOCUMENTS

| | | | |
|---|---|---|---|
| 2012/0064543 | A1 | 3/2012 | Takakura et al. |
| 2012/0140055 | A1 | 6/2012 | Narusawa et al. |
| 2012/0196296 | A1 | 8/2012 | Oldham |
| 2012/0196774 | A1 | 8/2012 | Fournier et al. |
| 2012/0212740 | A1 | 8/2012 | Oldham |
| 2012/0274760 | A1 | 11/2012 | King et al. |
| 2014/0206580 | A1 | 7/2014 | Grudzien et al. |
| 2014/0274786 | A1 | 9/2014 | Mccoy et al. |
| 2014/0323330 | A1 | 10/2014 | Bergo |
| 2015/0060700 | A1 | 3/2015 | Bjornson et al. |
| 2015/0070699 | A1 | 3/2015 | King et al. |
| 2015/0087614 | A1* | 3/2015 | Gilmore ............... C09B 33/056 |
| | | | 435/253.4 |
| 2015/0185152 | A1 | 7/2015 | Maher |
| 2015/0247190 | A1 | 9/2015 | Ismagilov et al. |
| 2015/0308944 | A1 | 10/2015 | Bjornson et al. |
| 2015/0355079 | A1 | 12/2015 | Empedolcles et al. |
| 2016/0041094 | A1 | 2/2016 | Lei |
| 2016/0146834 | A1 | 5/2016 | Quyyumi |
| 2016/0217315 | A1 | 7/2016 | Adalsteinsson |
| 2016/0228876 | A1 | 8/2016 | Chu et al. |
| 2016/0230210 | A1 | 8/2016 | Chen et al. |
| 2016/0245805 | A1 | 8/2016 | Baer et al. |
| 2016/0333400 | A1 | 11/2016 | Makino et al. |
| 2017/0023566 | A1 | 1/2017 | Merandon et al. |
| 2017/0343466 | A1 | 11/2017 | Dou et al. |
| 2017/0343476 | A1 | 11/2017 | Boege |
| 2018/0023124 | A1 | 1/2018 | Collins et al. |

FOREIGN PATENT DOCUMENTS

| | | |
|---|---|---|
| WO | 2001058956 | 8/2001 |
| WO | 2007104057 A1 | 9/2007 |
| WO | 2012121310 | 9/2012 |
| WO | 2016006208 | 1/2016 |

OTHER PUBLICATIONS

Gottlin et al., "Isolation of novel EGFR-specific VHH domains." J Biomol Screen. Jan. 2009; 14(1):77-85.

Heller, "Electrical wiring of redox enzymes," Acc. Chem. Res., 1990, 23(5):128-134.

Holt et al., "Domain antibodies: proteins for therapy" Trends in Biotechnology, 2014, 21:484-490.

Jeromin, "Ultrasensitive Detection Of Neurodegenerative Biomarkers In Blood With The Fullyautomated Simoa Analyzer: Clinical Applications." Poster Presentations: p. 515-516, 2014.

Jetha et al., "Nanopore Analysis of Wild-Type and Mutant Prion Protein (PrPC): Single Molecule Discrimination and PrPC Kinetics." PLOS ONE Feb. 2013, 8(2):e54982.

Kan et al., "Isolation and detection of single molecules on paramagnetic beads using sequential fluid flows in microfabricated polymer array assemblies." Lab Chip, 2012, 12:977-985.

Kuhle, "Comparison of three analytical platforms for quantification of the neurofilament light chain in blood samples: ELISA, electrochemiluminescence immunoassay and Simoa." Clin Chem Lab Med 2016; 54(10): 1655-1661.

"Lepor et al., ""Clinical evaluation of a novel method for the measurement of prostate-specifi c antigen, AccuPSA TM , as a predictor of 5-yearbiochemical recurrence-free survival afterradical prostatectomy: results of a pilot study.""" BJU International 2011, 109:1770-1775".

Mcenaney et al., "Antibody-recruiting molecules: an emerging paradigm for engaging immune function in treating human disease." ACS Chem Biol. Jul. 20, 2012; 7(7):1139-51.

Merouane et al., "Automated profiling of individual cell-cell interactions from high-throughput time-lapse imaging microscopy in nanowell grids (TIMING)." Bioinformatics. Oct. 1, 2015; 31(19):3189-97.

Millward et al., "Iterative in situ click chemistry assembles a branched capture agent and allosteric inhibitor for Akt1." J Am Chem Soc. Nov. 16, 2011; 133(45):18280-8.

Rissin et al., "Simultaneous Detection of Single Molecules and Singulated Ensembles of Molecules Enables Immunoassays with Broad Dynamic Range." Analytical Chemistry, 2011, 83:2279-2285.

Rissin et al., "Single-molecule enzyme-linked immunosorbent assay detects serum proteins at subfemtomolar concentrations." Nature Biotechnology Jun. 2010, 28(6):595-599.

Rondelez et al., "Microfabricated arrays of femtoliter chambers allow single molecule enzymology." Nat Biotechnol. Mar. 2005, 23(3):361-5.

Schubert et al., ""Ultra-sensitive protein detectionvia Single Molecule Arrays towards early stage cancer monitoring."" Jun. 8, 2015, 5:11034.

Shim et al., ""Ultrarapid Generation of FemtoliterMicrofluidic Droplets for Single-Molecule-Counting Immunoassays."" ACSNANO 2013, 7(7):5955-5964.

Tessler et al., "Sensitive single-molecule protein quantification and protein complex detection in a microarray format." Proteomics 2011, 11:4731-4735.

Tiede et al., "Adhiron: a stable and versatile peptide display scaffold for molecular recognition applications." Protein Eng Des Sel. May 2014; 27(5):145-55.

Wu et al., "Simultaneous targeting of multiple disease mediators by a dual-variable-domain immunoglobulin." Nat Biotechnol. Nov. 2007;25(11):1290-7.

Xu et al., "Novel solution-phase immunoassays for molecular analysis of tumor markers." Analyst 2001, 126: 1285-1292.

Zetterberg et al., "Hypoxia Due to Cardiac Arrest Induces a Time-Dependent Increase in Serum Amyloid b Levels In Humans." PLoS ONE Dec. 2011, 6(12):e28263.

Kim et al., "Large-scale femtoliter droplet array for digital counting of single biomolecules." Lab Chip. Dec. 7, 2012; 12 (23):4986-91.

Neuweiler et al., "Sensitive detection of p53 antibodies in a homogenous fluorescence assay format." Biomedical Nanotechnology Architectures and Applications, Darryl J. Bornhop, et al., Editors, Proceedings of SPIE vol. 4626 (2002), 259-267.

Patel et al. "Selection of a high-affinity WW domain against the extracellular region of VEGF receptor isoform-2 from a combinatorial library using CIS display." Protein Eng Des Sel. Apr. 2013, 26(4):307-15.

Radar, "Chemically programmed antibodies." Trends in Biotechnology, 2014, 32:186-197.

Obayashi et al., "A single-molecule digital enzyme assay using alkaline phosphatase with a cumarin-based fluorgenic substrate." Analyst 2015, 140: 5065-5073.

Bancroft et al., Theory and Practice of Histological Techniques, 2008.

Thermo Scientific Pierce Assay Development Technical Handbook, 2011.

Buma et al., "Thermoelastic Expansion vs. Piezoelectricity for High-Frequencey, 2-D Arrays." IEEE Transactions on Ultrasonices, Ferroelectrics, and Frequence Control Aug. 2003, 50(8): 1065-1068.

Chang et al., "Candle soot nanoparticles-polydimethylsiloxane composites for laser ultrasound transducers." Appl. Phys. Lett. 2015, 107:161903.

European Patent Office, Examination Report for EP Application No. 18748418.3, mailed Sep. 12, 2024.

* cited by examiner

METHODS FOR REDUCING NOISE IN SIGNAL-GENERATING DIGITAL ASSAYS

CROSS-REFERENCE TO RELATED APPLICATION(S)

This application is a continuation of granted U.S. application Ser. No. 15/888,952, filed Feb. 5, 2018, now U.S. Pat. No. 11,047,854, issued Jun. 29, 2021, which claims the benefit of U.S. Provisional Patent Application No. 62/455,436, filed on Feb. 6, 2017, both of which are incorporated by reference herein.

TECHNICAL FIELD

This disclosure relates to methods of reducing background noise in signal-generating digital assays using a colorant, such as an ink or dye.

BACKGROUND

Methods and devices that can accurately analyze analyte(s) of interest in a sample are essential for diagnostics, such as for example diagnosing a disease, disorder or condition, prognostics, environmental assessment, food safety, detection of chemical or biological warfare agents and the like. Most current techniques for quantifying low levels of analyte molecules in a sample use amplification procedures to increase the number of reporter molecules to provide a measurable signal. Examples of current techniques include enzyme-linked immunosorbent assays (ELISA) for amplifying the signal in antibody-based assays, as well as the polymerase chain reaction (PCR) for amplifying target DNA strands in DNA-based assays. Most detection schemes require the presence of a large number of molecules in the ensemble for the aggregate signal to be above the detection threshold. This requirement limits the sensitivity of most detection techniques and the dynamic range (i.e., the range of concentrations that can be detected). Many of the known methods and techniques are further plagued with problems of non-specific binding, which leads to an increase in the background signal and limits the lowest concentration that may be accurately or reproducibly detected.

Digital ELISA is a candidate for the next generation of immunoassays as it can detect one molecule of enzyme using a conjugate. See FIGS. 1 and 2. In the digital ELISA procedure, individual target analytes are captured on antibody-coated solid phases (e.g., beads) and then reacted with detection antibody conjugated with an enzyme. After removing unbound detection antibody, the beads are entrapped in each droplet chamber with the substrate of the enzyme and the beads are enclosed with the heavy oil (see yellow layer in step 3 of FIG. 2). During steps 3-8 of FIG. 2, the aqueous phase is displaced by the heavy oil and subsequently removed. It typically takes 30-40 minutes to completely remove the aqueous phase, which also includes the fluorescent substance (see sky blue layer in steps 1-7 of FIG. 2. Because the removal step 7 shown in FIG. 2 is performed manually, this poses challenges given the wide variety of times such assays are performed which results in accuracy issues depending upon the individual differences of each assay as well as the number of samples being tested. By way of example, if step 7 is performed incorrectly (i.e., there is incomplete removal of the aqueous layer), the signal ("glow") background noise obstructs the counting of the number of fluorescent droplets under a digital counting device (e.g., an optical microscope). In addition, any light source, such as a room lamp, may cause high background noise. As a result, there is a need for improved digital assays that are easily adaptable for a high throughput assay with reduced background noise, i.e., background signal (e.g., fluorescence or glow), and high accuracy.

SUMMARY

The present invention is directed to a signal-generating digital assay for determining the presence or absence of a single molecule of an analyte in a fluid sample. The assay includes: (a) contacting the fluid sample containing or suspected of containing the analyte with a plurality of solid supports to create a mixture, wherein each solid support comprises one or more first specific binding member capable of binding to the analyte thereby producing solid support-first specific binding member-analyte complexes; (b) washing the solid support-first specific binding member-analyte complexes in the mixture with a first wash buffer to remove any solid support-first specific binding member not bound to the analyte thereby producing a washed mixture; (c) adding to the washed mixture one or more second specific binding members capable of binding to the analyte thereby producing solid support-first specific binding member-analyte-second specific binding member complexes, wherein the second specific binding member comprises a signal generating compound attached thereto; (d) washing the solid support-first specific binding member-analyte-second specific binding member complexes with a second wash buffer to remove any second specific binding member not bound to the analyte bound to the first specific binding member thereby producing washed solid support complexes; (e) adding to the washed solid support complexes a signal generating substrate and a colorant, wherein the signal generating compound and the signal generating substrate produce a detectable signal; (f) spatially segregating at least a portion of the washed solid support complexes into a plurality of separate locations, wherein the plurality of separation locations comprises a plurality of reaction vessels and wherein the washed solid support complexes are present in an aqueous phase; (g) covering the plurality of reaction vessels with a sealant, wherein the aqueous phase is displaced by the sealant in the reaction chamber; and (h) detecting the presence or absence of the detectable signal using a digital counting device, wherein detection of the presence of the detectable signal indicates the presence of a single molecule of analyte in the sample.

The present invention is directed to a fluorescent digital immunoassay for determining the presence or absence of a single molecule of an analyte in a fluid sample. The immunoassay includes: (a) contacting the fluid sample containing or suspected of containing the analyte with a plurality of solid supports to create a mixture, wherein each solid support comprises one or more first specific binding member capable of binding to the analyte thereby producing solid support-first specific binding member-analyte complexes; (b) washing the solid support-first specific binding member-analyte complexes in the mixture with a first wash buffer to remove any solid support-first specific binding member not bound to the analyte thereby producing a washed mixture; (c) adding to the washed mixture one or more second specific binding members capable of binding to the analyte thereby producing solid support-first specific binding member-analyte-second specific binding member complexes, wherein the second specific binding member comprises a signal generating compound attached thereto; (d) washing the solid support-first specific binding member-analyte-second specific binding member complexes with a second wash buffer to remove any second specific binding member not bound to the analyte bound to the first specific binding member thereby producing washed solid support complexes; (e) adding to the washed solid support complexes a signal generating substrate and a colorant, wherein the signal generating compound and the signal generating substrate produce a detectable signal; (f) spatially segregating at least a portion of the washed solid support complexes into a plurality of separate locations, wherein the plurality of separation locations comprises a plurality of reaction vessels and wherein the washed solid support complexes are present in an aqueous phase; (g) covering the plurality of reaction vessels with a sealant, wherein the aqueous phase is displaced by the sealant in the reaction chamber; and (h) detecting the presence or absence of the detectable signal using a digital counting device, wherein detection of the presence of the detectable signal indicates the presence of a single molecule of analyte in the sample.

The present invention is directed to a signal-generating digital assay for determining the presence or absence of a single molecule of an analyte in a fluid sample. The assay includes: (a) contacting the fluid sample containing or suspected of containing the analyte with a plurality of solid supports to create a mixture, wherein each solid support comprises one or more first specific binding member capable of binding to the analyte thereby producing solid support-first specific binding member-analyte complexes; (b) washing the solid support-first specific binding member-analyte complexes in the mixture with a first wash buffer to remove any solid support-first specific binding member not bound to the analyte thereby producing a washed mixture; (c) adding to the washed mixture one or more second specific binding members capable of binding to the analyte thereby producing solid support-first specific binding member-analyte-second specific binding member complexes, wherein the second specific binding member comprises a signal generating compound attached thereto; (d) washing the solid support-first specific binding member-analyte-second specific binding member complexes with a second wash buffer to remove any second specific binding member not bound to the analyte bound to the first specific binding member thereby producing washed solid support complexes; (e) adding to the washed solid support complexes a signal generating substrate, wherein the signal generating compound and the signal generating substrate produce a detectable signal; (f) spatially segregating at least a portion of the washed solid support complexes into a plurality of separate locations, wherein the plurality of separation locations comprises a plurality of reaction vessels and wherein the washed solid support complexes are present in an aqueous phase; (g) covering the plurality of reaction vessels with a sealant, wherein the aqueous phase is displaced by the sealant in the reaction chamber; (h) adding a colorant to the displaced aqueous phase; and (i) detecting the presence or absence of the detectable signal using a digital counting device, wherein detection of the presence of the detectable signal indicates the presence of a single molecule of analyte in the sample.

The present invention is directed to a signal-generating digital assay for determining the presence or absence of a single molecule of an analyte in a fluid sample. The assay includes: (a) contacting the fluid sample containing or suspected of containing the analyte with a plurality of solid supports to create a mixture, wherein each solid support comprises one or more first specific binding member capable of binding to the analyte thereby producing solid support-first specific binding member-analyte complexes; (b) washing the solid support-first specific binding member-analyte complexes in the mixture with a first wash buffer to remove any solid support-first specific binding member not bound to the analyte thereby producing a washed mixture; (c) adding to the washed mixture one or more second specific binding members capable of binding to the analyte thereby producing solid support-first specific binding member-analyte-second specific binding member complexes, wherein the second specific binding member comprises a signal generating compound attached thereto; (d) washing the solid support-first specific binding member-analyte-second specific binding member complexes with a second wash buffer to remove any second specific binding member not bound to the analyte bound to the first specific binding member thereby producing washed solid support complexes; (e) adding to the washed solid support complexes a signal generating substrate, wherein the signal generating compound and the signal generating substrate produce a detectable signal; (f) spatially segregating at least a portion of the washed solid support complexes into a plurality of separate locations, wherein the plurality of separation locations comprises a plurality of reaction vessels and wherein the washed solid support complexes are present in an aqueous phase; (g) covering the plurality of reaction vessels with a sealant, wherein the aqueous phase is displaced by the sealant in the reaction chamber; (h) adding a colorant to the sealant; and (i) detecting the presence or absence of the detectable signal using a digital counting device, wherein detection of the presence of the detectable signal indicates the presence of a single molecule of analyte in the sample.

The present invention is directed to a fluorescent digital immunoassay for determining the presence or absence of a single molecule of an analyte in a fluid sample. The immunoassay includes: (a) contacting the fluid sample containing or suspected of containing the analyte with a plurality of solid supports to create a mixture, wherein each solid support comprises one or more first specific binding member capable of binding to the analyte thereby producing solid support-first specific binding member-analyte complexes; (b) washing the solid support-first specific binding member-analyte complexes in the mixture with a first wash buffer to remove any solid support-first specific binding member not bound to the analyte thereby producing a washed mixture; (c) adding to the washed mixture one or more second specific binding members capable of binding to the analyte thereby producing solid support-first specific binding member-analyte-second specific binding member complexes, wherein the second specific binding member comprises a signal generating compound attached thereto; (d) washing the solid support-first specific binding member-analyte-second specific binding member complexes with a second wash buffer to remove any second specific binding member not bound to the analyte bound to the first specific binding member thereby producing washed solid support complexes; (e) adding to the washed solid support complexes a signal generating substrate, wherein the signal generating compound and the signal generating substrate produce a detectable signal; (f) spatially segregating at least a portion of the washed solid support complexes into a plurality of separate locations, wherein the plurality of separation locations comprises a plurality of reaction vessels and wherein the washed solid support complexes are present in an aqueous phase; (g) covering the plurality of reaction vessels with a sealant, wherein the aqueous phase is displaced by the sealant in the reaction chamber; (h) adding a colorant to the displaced aqueous phase; and (i) detecting the presence or absence of the detectable signal using a digital counting device, wherein detection of the presence of the detectable signal indicates the presence of a single molecule of analyte in the sample.

The present invention is directed to a fluorescent digital immunoassay for determining the presence or absence of a single molecule of an analyte in a fluid sample. The immunoassay includes: (a) contacting the fluid sample containing or suspected of containing the analyte with a plurality of solid supports to create a mixture, wherein each solid support comprises one or more first specific binding member capable of binding to the analyte thereby producing solid support-first specific binding member-analyte complexes; (b) washing the solid support-first specific binding member-analyte complexes in the mixture with a first wash buffer to remove any solid support-first specific binding member not bound to the analyte thereby producing a washed mixture; (c) adding to the washed mixture one or more second specific binding members capable of binding to the analyte thereby producing solid support-first specific binding member-analyte-second specific binding member complexes, wherein the second specific binding member comprises a signal generating compound attached thereto; (d) washing the solid support-first specific binding member-analyte-second specific binding member complexes with a second wash buffer to remove any second specific binding member not bound to the analyte bound to the first specific binding member thereby producing washed solid support complexes; (e) adding to the washed solid support complexes a signal generating substrate, wherein the signal generating compound and the signal generating substrate produce a detectable signal; (f) spatially segregating at least a portion of the washed solid support complexes into a plurality of separate locations, wherein the plurality of separation locations comprises a plurality of reaction vessels and wherein the washed solid support complexes are present in an aqueous phase; (g) covering the plurality of reaction vessels with a sealant, wherein the aqueous phase is displaced by the sealant in the reaction chamber; (h) adding a colorant to the sealant; and (i) detecting the presence or absence of the detectable signal using a digital counting device, wherein detection of the presence of the detectable signal indicates the presence of a single molecule of analyte in the sample.

The present invention is directed to a method for reducing fluorescence background noise in a signal-generating digital assay used to detect an analyte in a sample. The method includes: (a) contacting a fluid sample containing or suspected of containing the analyte with a plurality of solid supports to create a mixture, wherein each solid support comprises one or more first specific binding member capable of binding to the analyte thereby producing solid support-first specific binding member-analyte complexes; (b) washing the solid support-first specific binding member-analyte complexes in the mixture with a first wash buffer to remove any solid support-first specific binding member not bound to the analyte thereby producing a washed mixture; (c) adding to the washed mixture one or more second specific binding members capable of binding to the analyte thereby producing solid support-first specific binding member-analyte-second specific binding member complexes, wherein the second specific binding member comprises a signal generating compound attached thereto; (d) washing the solid support-first specific binding member-analyte-second specific binding member complexes with a second wash buffer to remove any second specific binding member not bound to the analyte bound to the first specific binding member thereby producing washed solid support complexes; (e) adding to the washed solid support complexes a signal generating substrate, wherein the signal generating compound and the signal generating substrate produce a detectable signal; (f) spatially segregating at least a portion of the washed solid support complexes into a plurality of separate locations, wherein the plurality of separation locations comprises a plurality of reaction vessels and wherein the washed solid support complexes are present in an aqueous phase; (g) covering the plurality of reaction vessels with a sealant, wherein the aqueous phase is displaced by the sealant in the reaction chamber; and (h) detecting the presence or absence of the detectable signal using a digital counting device, wherein detection of the presence of the detectable signal indicates the presence of a single molecule of analyte in the sample, wherein the digital counting device comprises a black device.

The present invention is directed to a method for reducing fluorescence background noise in a fluorescent digital immunoassay used to detect an analyte in a sample. The method includes: (a) contacting a fluid sample containing or suspected of containing the analyte with a plurality of solid supports to create a mixture, wherein each solid support comprises one or more first specific binding member capable of binding to the analyte thereby producing solid support-first specific binding member-analyte complexes; (b) washing the solid support-first specific binding member-analyte complexes in the mixture with a first wash buffer to remove any solid support-first specific binding member not bound to the analyte thereby producing a washed mixture; (c) adding to the washed mixture one or more second specific binding members capable of binding to the analyte thereby producing solid support-first specific binding member-analyte-second specific binding member complexes, wherein the second specific binding member comprises a signal generating compound attached thereto; (d) washing the solid support-first specific binding member-analyte-second specific binding member complexes with a second wash buffer to remove any second specific binding member not bound to the analyte bound to the first specific binding member thereby producing washed solid support complexes; (e) adding to the washed solid support complexes a signal generating substrate, wherein the signal generating compound and the signal generating substrate produce a detectable signal; (f) spatially segregating at least a portion of the washed solid support complexes into a plurality of separate locations, wherein the plurality of separation locations comprises a plurality of reaction vessels and wherein the washed solid support complexes are present in an aqueous phase; (g) covering the plurality of reaction vessels with a sealant, wherein the aqueous phase is displaced by the sealant in the reaction chamber; and (h) detecting the presence or absence of the detectable signal using a digital counting device, wherein detection of the presence of the detectable signal indicates the presence of a single molecule of analyte in the sample, wherein the digital counting device comprises a black device.

BRIEF DESCRIPTION OF THE DRAWINGS

The details of the subject matter set forth herein, both as to its structure and operation, may be apparent by study of the accompanying figures, in which like reference numerals refer to like parts. The components in the figures are not necessarily to scale, emphasis instead being placed upon illustrating the principles of the subject matter. Moreover, all illustrations are intended to convey concepts, where relative sizes, shapes and other detailed attributes may be illustrated schematically rather than literally or precisely.

DETAILED DESCRIPTION

Figure 1:
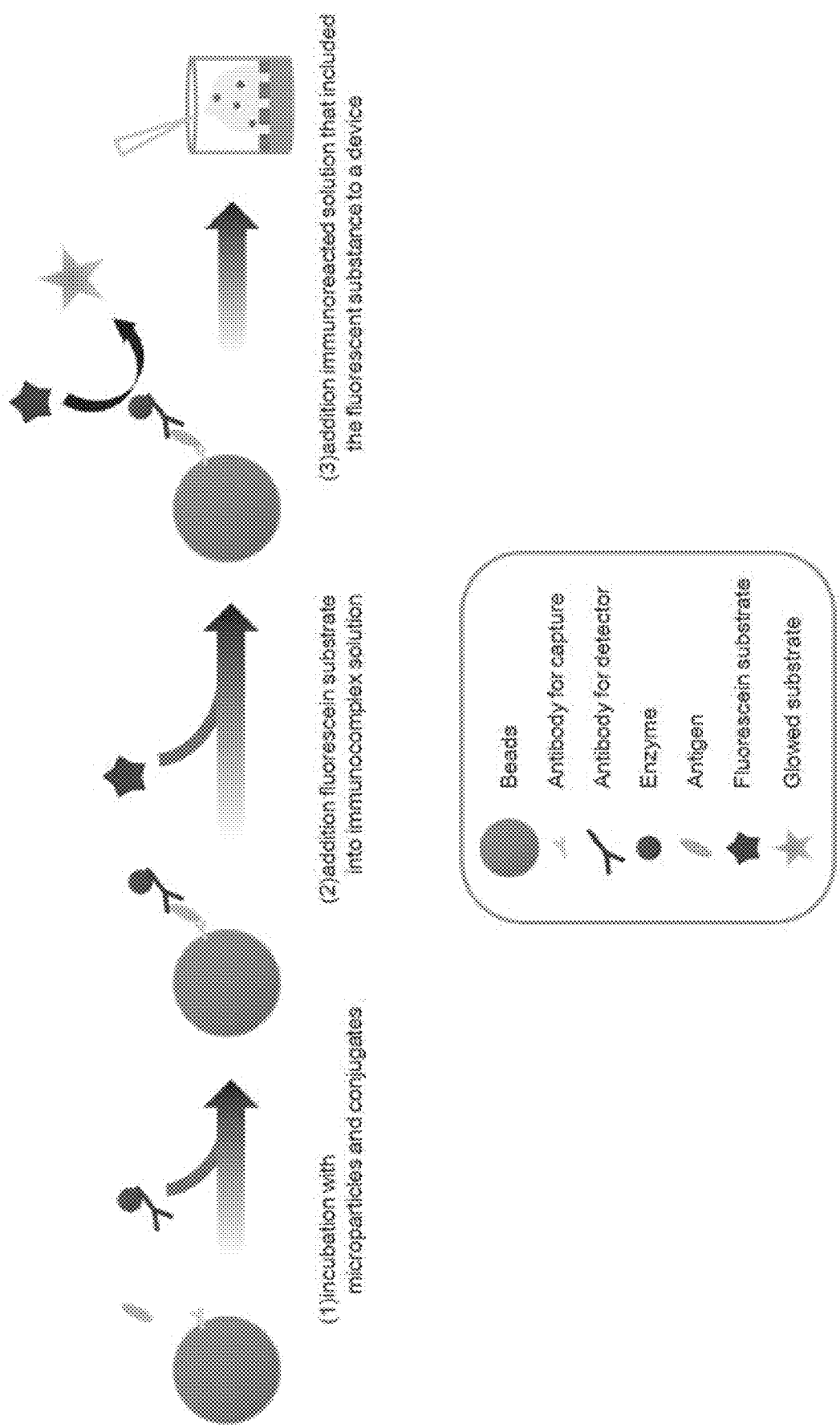
FIG. 1 shows the procedure of a fluorescent digital ELISA assay.

Embodiments of the present disclosure relate to the use of a colorant, such as one or more dark/black inks or dyes, to reduce background signal (e.g., fluorescence) in an assay, such as a digital ELISA, without the need to remove an aqueous phase. For example, in digital immunoassays, analytes of interest are captured on solid supports between a capture molecule and a detection molecule (which is bound to a signal generating compound (e.g., such as an enzyme)) to form a capture molecule-analyte of interest-detection molecule complex. The solid supports containing the capture molecule-analyte of interest-detection molecule complex are then entrapped in a droplet and the droplet is moved to an array of reaction vessels (e.g., wells) which creates an aqueous phase within each of the reaction vessels. The reaction vessels can be sealed or covered in a "solvent well-sealing" method by the addition of a sealant that includes one or more solvents, such as a hydrophilic or a hydrophobic solvent that has a density that is heavier than the aqueous phase. After the sealant is added to the reaction vessels, the sealant moves towards the bottom of the reaction vessel because of its heavier density and displaces the aqueous phase, thus forcing it to the surface and creating a clear separation between the upper aqueous phase and the lower solvent phase. For example, the plurality of reaction vessels can be covered with heavy fluorinated oil and the aqueous phase and the oil phase are changed. After the aqueous phase and the oil phase are changed, the aqueous phase is removed. The upper aqueous phase can be removed using routine techniques known in the art.

One of the problems with the solvent sealing method is that the residual aqueous phase can cause background signal or detectable label (e.g., fluorescence). Another source of background signal is any light, such as a room lamp. Another problem is the need to remove the aqueous solution from the oil before detection, which is a very time consuming step and leads to very low throughput of the assay and very variable incubation time for each test. The addition of a colorant to any solution phase, including the aqueous phase or sealant (e.g., oil) phase, suppresses the background fluorescent noise and eliminates the need to remove the aqueous phase, improving the ease with which the assay can be performed and the quality of the images obtained during analysis. Thus, the present invention simplifies and shortens the protocol of digital assays by reducing the number of steps needed to perform the assay. For example, the need to remove the aqueous solution from the oil before detection is eliminated by the presently disclosed method. In addition, the present invention can be modified for use in high throughput assay, applied for full automatic dispensing system, reduce background of the assay produced signal, and improve data accuracy. The present invention can solve both the low throughput issue of the digital assays, particularly digital ELISA assays and the accuracy issue of the data depending on the individual differences or the number of testing. Additionally, the improved method described herein provides a unique application that can mimic "evanescent light detection system" without requiring the use of highly expensive digital counting devices such as a scanning near-field optical microscope. The presently disclosed methods, for example, the method shown in FIG. 7A, can limit the light area (as shown in FIG. 7B), which is comparable to the light area in an evanescent light detection system.

1. DEFINITIONS

Before the embodiments of the present disclosure are described, it is to be understood that this invention is not limited to particular embodiments described, as such may, of course, vary. It is also to be understood that the terminology used herein is for the purpose of describing particular embodiments only, and is not intended to be limiting.

"Comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

"Affinity" and "binding affinity" as used interchangeably herein refer to the tendency or strength of binding of the binding member to the analyte. For example, the binding affinity may be represented by the equilibrium dissociation constant ($K_D$), the dissociation rate ($k_d$), or the association rate ($k_a$).

"Analog" as used herein refers to a molecule that has a similar structure to a molecule of interest (e.g., nucleoside analog, nucleotide analog, sugar phosphate analog, analyte analog, etc.). An analyte analog is a molecule that is structurally similar to an analyte but for which the binding member has a different affinity.

"Analyte", "target analyte", "analyte of interest" as used interchangeably herein, refer to an analyte being measured in the methods and devices disclosed herein. Analytes of interest are further described herein.

"Antibody" and "antibodies" as used herein refers to monoclonal antibodies, multispecific antibodies, human antibodies, humanized antibodies (fully or partially humanized), animal antibodies such as, but not limited to, a bird (for example, a duck or a goose), a shark, a whale, and a mammal, including a non-primate (for example, a cow, a pig, a camel, a llama, a horse, a goat, a rabbit, a sheep, a hamster, a guinea pig, a cat, a dog, a rat, a mouse, etc.) or a non-human primate (for example, a monkey, a chimpanzee, etc.), recombinant antibodies, chimeric antibodies, single-chain Fvs ("scFv"), single chain antibodies, single domain antibodies, Fab fragments, F(ab') fragments, F(ab')2 fragments, disulfide-linked Fvs ("sdFv"), and anti-idiotypic ("anti-Id") antibodies, dual-domain antibodies, dual variable domain (DVD) or triple variable domain (TVD) antibodies (dual-variable domain immunoglobulins and methods for making them are described in Wu, C., et al., *Nature Biotechnology*, 25(11):1290-1297 (2007) and PCT International Patent Application WO 2001/058956, the contents of each of which are herein incorporated by reference), and functionally active epitope-binding fragments of any of the above. In particular, antibodies include immunoglobulin molecules and immunologically active fragments of immunoglobulin molecules, namely, molecules that contain an analyte-binding site. Immunoglobulin molecules can be of any type (for example, IgG, IgE, IgM, IgD, IgA, and IgY), class (for example, IgG1, IgG2, IgG3, IgG4, IgA1, and IgA2), or subclass. For simplicity sake, an antibody against an analyte is frequently referred to herein as being either an "anti-analyte antibody" or merely an "analyte antibody."

"Antibody fragment" as used herein refers to a portion of an intact antibody comprising the antigen-binding site or variable region. The portion does not include the constant heavy chain domains (i.e., CH2, CH3, or CH4, depending on the antibody isotype) of the Fc region of the intact antibody. Examples of antibody fragments include, but are not limited to, Fab fragments, Fab' fragments, Fab'-SH fragments, F(ab')2 fragments, Fd fragments, Fv fragments, diabodies, single-chain Fv (scFv) molecules, single-chain polypeptides containing only one light chain variable domain, single-chain polypeptides containing the three CDRs of the light-chain variable domain, single-chain polypeptides containing only one heavy chain variable region, and single-chain polypeptides containing the three CDRs of the heavy chain variable region.

"Bead" and "particle" are used herein interchangeably and refer to a substantially spherical solid support.

"Binding Protein" is used herein to refer to a monomeric or multimeric protein that binds to and forms a complex with a binding partner, such as, for example, a polypeptide, an antigen, a chemical compound or other molecule, or a substrate of any kind. A binding protein specifically binds a binding partner. Binding proteins include antibodies, as well as antigen-binding fragments thereof and other various forms and derivatives thereof as are known in the art and described herein below, and other molecules comprising one or more antigen-binding domains that bind to an antigen molecule or a particular site (epitope) on the antigen molecule. Accordingly, a binding protein includes, but is not limited to, an antibody a tetrameric immunoglobulin, an IgG molecule, an $IgG_1$ molecule, a monoclonal antibody, a chimeric antibody, a CDR-grafted antibody, a humanized antibody, an affinity matured antibody, and fragments of any such antibodies that retain the ability to bind to an antigen.

"Capture molecule" as used herein refers to a specific binding partner or specific binding member used to capture or immobilize an analyte of interest in a biological sample. A capture molecule is often one component of a complex in addition to the analyte of interest and may also contain one or more detection molecules. The complex may optionally be bound to a solid support.

"Component," "components," or "at least one component," refer generally to a capture antibody, a detection reagent or conjugate, a calibrator, a control, a sensitivity panel, a container, a buffer, a diluent, a salt, an enzyme, a co-factor for an enzyme, a detection reagent, a pretreatment reagent/solution, a substrate (e.g., as a solution), a stop solution, and the like that can be included in a kit for assay of a test sample, such as patient urine, serum, whole blood, tissue aspirate, or plasma sample, in accordance with the methods described herein and other methods known in the art. Some components can be in solution or lyophilized for reconstitution for use in an assay.

"Contacting" and grammatical equivalents thereof as used herein refer to any type of combining action which brings a binding member into sufficiently close proximity with the analyte of interest in the sample such that a binding interaction will occur if the analyte of interest specific for the binding member is present in the sample. Contacting may be achieved in a variety of different ways, including combining the sample with a binding member, exposing a target analyte to a binding member by introducing the binding member in close proximity to the analyte, and the like.

"Control" as used herein refers to a reference standard for an analyte such as is known or accepted in the art, or determined empirically using acceptable means such as are commonly employed. A "reference standard" is a standardized substance which is used as a measurement base for a similar substance. For example, there are documented reference standards published in the U.S. Pharmacopeial Convention (USP-NF), Food Chemicals Codex, and Dietary Supplements Compendium (all of which are available at http://www.usp.org), and other well-known sources. Methods for standardizing references are described in the literature. Also well-known are means for quantifying the amounts of analyte present by use of a calibration curve for analyte or by comparison to an alternate reference standard. A standard curve can be generated using serial dilutions or solutions of known concentrations of analyte, by mass spectroscopy, gravimetric methods, and by other techniques known in the art. Alternate reference standards that have been described in the literature include standard addition (also known as the method of standard addition), or digital polymerase chain reaction.

"Detection molecule" as used herein refers to a specific binding partner or specific binding member that is used to detect the presence of and/or quantify or measure the amount of an analyte of interest in a biological sample. A detection molecule is often one component of a complex that may contain a one or more capture molecules and an analyte of interest. The complex may optionally be bound to a solid support.

"Immobilized" as used herein, refers to a stable association of the first specific binding member with a surface of a solid support. By "stable association" is meant a physical association between two entities in which the mean half-life of association is one day or more, e.g., under physiological conditions. In certain aspects, the physical association between the two entities has a mean half-life of two days or more, one week or more, one month or more, including six months or more, e.g., 1 year or more, in PBS at 4° C. According to certain embodiments, the stable association arises from a covalent bond between the two entities, a non-covalent bond between the two entities (e.g., an ionic or metallic bond), or other forms of chemical attraction, such as hydrogen bonding, Van der Waals forces, and the like.

"Label" and "detectable label" as used herein refer to a moiety attached to an antibody or an analyte to render the reaction between the antibody and the analyte detectable, and the antibody or analyte so labeled is referred to as "detectably labeled." A label can produce a signal that is detectable by visual or instrumental means. Various labels include signal-producing substances, such as chromogens, fluorescent compounds, chemiluminescent compounds, radioactive compounds, and the like. Other labels are described herein. In this regard, the moiety, itself, may not be detectable but may become detectable upon reaction with yet another moiety. Use of the term "detectably labeled" is intended to encompass such labeling.

"Monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen. Furthermore, in contrast to polyclonal antibody preparations that typically include different antibodies directed against different determinants (epitopes), each monoclonal antibody is directed against a single determinant on the antigen. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological.

"Polynucleotides" or "oligonucleotides" refer to nucleobase polymers or oligomers in which the nucleobases are connected by sugar phosphate linkages (sugar-phosphate backbone). Exemplary poly- and oligonucleotides include polymers of 2'-deoxyribonucleotides (DNA) and polymers of ribonucleotides (RNA). A polynucleotide may be composed entirely of ribonucleotides, entirely of 2'-deoxyribonucleotides or combinations thereof. "Nucleic acid" encompasses "polynucleotide" and "oligonucleotides" and includes single stranded and double stranded polymers of nucleotide monomers.

"Predetermined cutoff" and "predetermined level" as used herein refer to an assay cutoff value that is used to assess diagnostic, prognostic, or therapeutic efficacy results by comparing the assay results against the predetermined cutoff/level, where the predetermined cutoff/level already has been linked or associated with various clinical parameters (e.g., presence of disease, stage of disease, severity of disease, progression, non-progression, or improvement of disease, etc.). The disclosure provides exemplary predetermined levels. However, it is well-known that cutoff values may vary depending on the nature of the immunoassay (e.g., antibodies employed, reaction conditions, sample purity, etc.). It further is well within the ordinary skill of one in the art to adapt the disclosure herein for other immunoassays to obtain immunoassay-specific cutoff values for those other immunoassays based on the description provided by this disclosure. Whereas the precise value of the predetermined cutoff/level may vary between assays, the correlations as described herein should be generally applicable.

"Pretreatment reagent," e.g., lysis, precipitation and/or solubilization reagent, as used in a diagnostic assay as described herein is one that lyses any cells and/or solubilizes any analyte that is/are present in a test sample. Pretreatment is not necessary for all samples, as described further herein. Among other things, solubilizing the analyte entails release of the analyte from any endogenous binding proteins present in the sample. A pretreatment reagent may be homogeneous (not requiring a separation step) or heterogeneous (requiring a separation step). With use of a heterogeneous pretreatment reagent, there is removal of any precipitated analyte binding proteins from the test sample prior to proceeding to the next step of the assay. The pretreatment reagent optionally can comprise: (a) one or more solvents and salt, (b) one or more solvents, salt and detergent, (c) detergent, (d) detergent and salt, or (e) any reagent or combination of reagents appropriate for cell lysis and/or solubilization of analyte.

"Quality control reagents" in the context of immunoassays and kits described herein, include, but are not limited to, calibrators, controls, and sensitivity panels. A "calibrator" or "standard" typically is used (e.g., one or more, such as a plurality) in order to establish calibration (standard) curves for interpolation of the concentration of an analyte, such as an antibody or an analyte. Alternatively, a single calibrator, which is near a predetermined positive/negative cutoff, can be used. Multiple calibrators (i.e., more than one calibrator or a varying amount of calibrator(s)) can be used in conjunction to comprise a "sensitivity panel."

"Receptor" as used herein refers to a protein-molecule that recognizes and responds to endogenous-chemical signals. When such endogenous-chemical signals bind to a receptor, they cause some form of cellular/tissue-response. Examples of receptors include, but are not limited to, neural receptors, hormonal receptors, nutrient receptors, and cell surface receptors.

"Recombinant antibody" and "recombinant antibodies" refer to antibodies prepared by one or more steps, including cloning nucleic acid sequences encoding all or a part of one or more monoclonal antibodies into an appropriate expression vector by recombinant techniques and subsequently expressing the antibody in an appropriate host cell. The terms include, but are not limited to, recombinantly produced monoclonal antibodies, chimeric antibodies, humanized antibodies (fully or partially humanized), multi-specific or multi-valent structures formed from antibody fragments, bifunctional antibodies, heteroconjugate Abs, DVD-Ig®s, and other antibodies as described in (i) herein. (Dual-variable domain immunoglobulins and methods for making them are described in Wu, C., et al., *Nature Biotechnology*, 25:1290-1297 (2007)). The term "bifunctional antibody," as used herein, refers to an antibody that comprises a first arm having a specificity for one antigenic site and a second arm having a specificity for a different antigenic site, i.e., the bifunctional antibodies have a dual specificity.

"Sample," "test sample," "biological sample," "sample from a subject," "fluid biological sample," and "patient sample" as used herein may be used interchangeable and refer to fluid sample containing or suspected of containing an analyte of interest.

As used herein, "signal generating compound" refers to any molecule, compound, protein or the like that can be converted to a detectable product or detectable label upon exposure to a suitable or appropriate converting agent, such as a signal generating substrate. A "detectable product" or "detectable label" is any molecule, particle, or the like, that facilitates detection, by acting as the detected entity, using a chosen technique known in the art. An example of a signal generating compound is an enzyme such as amylases, polynucleotidase, arginase, adenase, aminopolypeptidase, pepsin, lipases, catalase, tyrosinases, alcohol dehydrogenase, succinic dehydrogenase, diaphorase, glyoxalase, aldolase, glucose oxidase, horseradish peroxidase, a galactosidase (such as beta-galactosidase), phosphatases, phosphorylases and hexokinases or combinations thereof.

As used herein "signal generating substrate" refers any molecule, compound, protein, substance, particle, or the like, that can be converted to or result in a signal generating compound being converted to a detectable product or detectable label upon exposure to a suitable or appropriate converting agent, such as a signal generating compound. A "detectable compound" or "detectable label" is any molecule, particle, or the like, that facilitates detection, by acting as the detected entity, using a chosen technique known in the art. Signal generating substrates can be colorimetric, chemiluminescent or chemifluorescent. An example of a signal generating substrate is an enzymatic substrate, such as a chemiluminescent substrate such as CDP-Star®, (disodium 4-chloro-3-(methoxyspiro{1,2-dioxetane-3,2'-(5'-chloro)tricyclo[3.3.1.1.s-up.3,7]decane}-4-yl)phenyl phosphate), CSPD®, or (disodium 3-(4-methoxyspiro{1,2-dioxetane-3,2-(5'-chloro)tricyclo[3.3.1.1-.sup.3,7]decane}-4-yl)phenyl phosphate); a luminescent substrate such as p-nitrophenyl phosphate, 5-bromo-4-chloro-3-indolyl phosphate (BCIP), 4-nitro blue tetrazolium chloride (NBT), or iodonitrotetrazolium (INT); a fluorescent substrate such as 4-methylumbelliferyl phosphate (4-MUP); and a chromogenic substrate such as 5-bromo-4-chloro-3-indolyl phosphate (BCIP), disodium 5-bromo-6-chloro-indolyl phosphate, or p-nitrophenyl phosphate.

"Specific binding partner" or "specific binding member" as used interchangeably herein refers to one of two or more different molecules that specifically recognize the other molecule compared to substantially less recognition of other molecules. The one of two different molecules has an area on the surface or in a cavity, which specifically binds to and is thereby defined as complementary with a particular spatial and polar organization of the other molecule. The molecules may be members of a specific binding pair. For example, a specific binding member may include, but is not limited to, a protein, such as a receptor, an enzyme, and an antibody.

In addition to antigen and antibody specific binding pairs of common immunoassays, other specific binding pairs can include biotin and avidin (or streptavidin), carbohydrates and lectins, complementary nucleotide sequences, effector and receptor molecules, cofactors and enzymes, enzymes and enzyme inhibitors, and the like. Furthermore, specific binding pairs can include members that are analogs of the original specific binding members, for example, an analyte-analog. Immunoreactive specific binding members include antigens, antigen fragments, and antibodies, including monoclonal and polyclonal antibodies as well as complexes and fragments thereof, whether isolated or recombinantly produced.

"Solid phase" or "solid support" as used interchangeably herein, refers to any material that is insoluble, or can be made insoluble by a subsequent reaction. The solid phase can be chosen for its intrinsic ability to attract and immobilize a capture agent. Alternatively, the solid phase can have affixed thereto a linking agent that has the ability to attract and immobilize the capture agent. For example, the linking agent can include a charged substance that is oppositely charged with respect to the capture agent itself or to a charged substance conjugated to the capture agent. In general, the linking agent can be any binding partner (preferably specific) that is immobilized on (attached to) the solid phase and that has the ability to immobilize the capture agent through a binding reaction. The linking agent enables the indirect binding of the capture agent to a solid phase material before the performance of the assay or during the performance of the assay. For examples, the solid phase can be plastic, derivatized plastic, magnetic, or non-magnetic metal, glass or silicon, including, for example, a test tube, microtiter well, sheet, bead, microparticle, chip, and other configurations known to those of ordinary skill in the art.

"Subject" and "patient" as used herein interchangeably refers to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous or rhesus monkey, chimpanzee, etc.) and a human). In some embodiments, the subject may be a human or a non-human. The subject or patient may be undergoing other forms of treatment.

"Threshold" as used herein refers to an empirically determined and subjective cutoff level above which acquired data is considered "signal," and below which acquired data is considered "noise." A computer program based on CUSUM (Cumulative Sums Algorithm) is employed to process acquired data and detect events based on threshold input from the user. Variation between users is avoided by detection of any many events as possible followed by filtering the data afterwards for specific purposes. With a "loose" threshold a lesser number of events will be counted as signal. With a "tight" threshold a greater number of events will be counted as signal. Setting the threshold as loose or tight is a subjective choice based on the desired sensitivity or specificity for an assay, and whether in a given assessment false positives or false negatives would be preferred.

"Treat", "treating" or "treatment" are each used interchangeably herein to describe reversing, alleviating, or inhibiting the progress of a disease, or one or more symptoms of such disease, to which such term applies. Depending on the condition of the subject, the term also refers to preventing a disease, and includes preventing the onset of a disease, or preventing the symptoms associated with a disease. A treatment may be either performed in an acute or chronic way. The term also refers to reducing the severity of a disease or symptoms associated with such disease prior to affliction with the disease. Such prevention or reduction of the severity of a disease prior to affliction refers to administration of an antibody or pharmaceutical composition of the present invention to a subject that is not at the time of administration afflicted with the disease. "Preventing" also refers to preventing the recurrence of a disease or of one or more symptoms associated with such disease. "Treatment" and "therapeutically," refer to the act of treating, as "treating" is defined above.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety to disclose and describe the methods and/or materials in connection with which the publications are cited. The materials, methods, and examples disclosed herein are illustrative only and not intended to be limiting.

2. IMPROVED SIGNAL-GENERATING DIGITAL ASSAYS

The present invention relates to improved assays, such as fluorescent immunoassays, that employ an array of reaction vessels (such as one or more wells), are sealed using solvent well sealing, and exhibit reduced background noise.

In fluorescent immunoassays, a single molecule of signal generating compound can generate a detectable signal by accumulating the detectable label produced from the signal generating substrate in a femto-liter chamber. While digital ELISAs have vast potential, one of the drawbacks is that the assay requires a number of steps to be performed. These steps include: 1) forming a capture molecule-analyte of interest-detection molecule complex on a solid support; 2) entrapping the complex in a droplet; 3) moving the droplet into a reaction vessel and adding a signal generation substrate (either simultaneously or sequentially with the droplet in any order) to form an aqueous phase, 4) adding a solvent, such as fluorinated oil (FC40), to the reaction vessel, causing the aqueous and solvent phases to switch thereby resulting in the separation of the aqueous solution in the reaction vessel; 5) removing the aqueous phase (which is the upper or top layer in the reaction vessel); and 6) acquiring an image of the reaction vessel using a digital counting device (such as an optical microscope). The removal of the aqueous phase in step 5 is for the purposes of eliminating background signal phase but is very time consuming. Specifically, one skilled in the art has to make sure to remove the aqueous phase completely because incomplete removal of the aqueous phase will result in residual background signal (fluorescence or glow noise). This background noise is caused by signal (fluorescence or glow) present in the upper aqueous phase and obstructs the counting of the number of signal generating droplets under the digital counting device (such as an optical microscope).

To delete the signal background noise, the present invention involves an improved method of conducting a digital assay that involves adding one or more colorants, such as a dye component (e.g. black ink), into the solution phase (aqueous or sealant (e.g., oil)) before or after adding the droplet or before or after adding the droplet and the signal generating substrate to the reaction vessel. As a result, the addition of the colorant (such as black ink or mixed black ink) obtains the same result as removing the aqueous phase, thus eliminating the need for this step in the assay completely. In the dye mixing method described herein, the colorant suppresses not only the background signal noise in the aqueous phase which is separated by the solvent addition, but also suppresses the background signal noise anywhere in the digital counting device. As a result, true signals, free from background, can be easily obtained from the image with the deepest shade of color (such as black). While not wishing to be bound by any theory, it is believed that the reason that such true signals can be obtained is that the light path length of the reaction vessel is very small (for example, if a femto-liter reaction vessel is used, the chamber is only 4 micrometers), and the transmissivity of the true signal is not affected or be interfered by the colorant in the solution.

Figure 2:
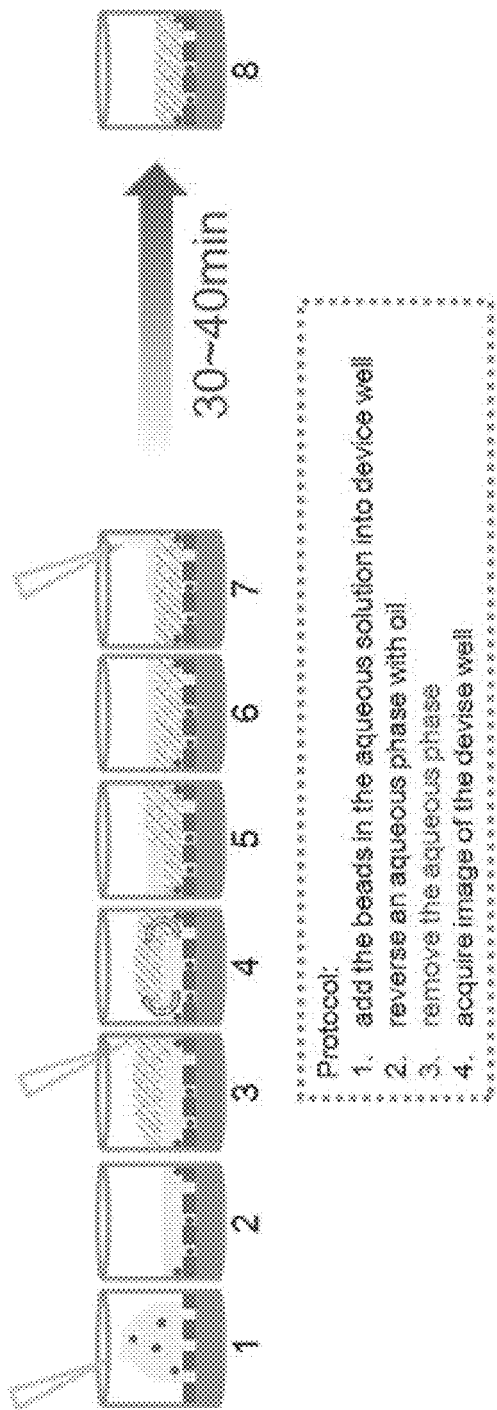
FIG. 2 shows a procedure of a fluorescent digital ELISA assay using a drip oil sealing step and an aqueous phase removal step.

The present disclosure describes improved methods for measuring or detecting an analyte present in a fluid biological sample using an array comprising a plurality of reaction vessels using the solvent sealing method which involves a sealant. For example, FIGS. 1 and 2 show schematics of a digital immunoassay using a drip oil sealing method. The 'digital ELISA' is based on the array device of a million of femto-liter size of water-in oil (W/O) droplets. The digital immunoassay may be an ultra-high sensitive immunoassay, such as a digital ELISA that could detect target molecules around the concentration of atto to sub-femto mol/L level (atto=$10^{-18}$, femto=$10^{-15}$). Other methods of drip oil sealing include those described in, for example, Rondelez et al., *Nature biotechnology* 23(3):361-365 (2005), Kim et al., *Lab on a Chip* 12(23):4986-4991(2012), Japan Patent Number 3727026, and International Patent Publication Numbers WO2012/121310 and WO2016/006208, the contents of each of which are herein incorporated by reference. In some embodiments, the signal-generating digital immunoassay includes a femto-liter droplet array.

The method for measuring or detecting the analyte includes exposing or contacting the fluid biological sample to a plurality of solid supports to create a mixture, each solid support comprises at least one first specific binding member ("binding members" alternately referred to as "specific binding members," and as described below) capable of binding to the analyte, wherein at least some fraction of the specific binding members bind to the analyte thereby producing solid support-first specific binding member-analyte complexes and at least some fraction of the specific binding members does not bind to any analyte; adding to or contacting with the mixture one or more second specific binding members capable of binding to the analyte thereby producing solid support-first specific binding member-analyte-second specific binding member complexes, the second specific binding member comprising a signal generating compound; adding a signal generating substrate to the solid support-first specific binding member-analyte-second specific binding member complexes; and spatially segregating at least a portion of the solid support-first specific binding member-analyte-second specific binding member complexes into a plurality of separate locations. In the improved method, a colorant is added before or after spatially segregating at least a portion of the solid support-first specific binding member-analyte-second specific binding member complexes into a plurality of separate locations (i.e., femtoliter chamber formation).

The plurality of reaction vessels are covered with a sealant, such as a heavy fluorinated oil, and the aqueous phase and the sealant phase (e.g., oil phase) are changed. In some embodiments, the aqueous phase and the sealant phase (e.g., oil phase) are changed by tilting the plurality of reaction vessels. In some embodiments, the heavy fluorinate oil is FC-40, FC-72, FC-84, FC-77, FC-3255, FC-3283, FC-43, FC-70), 3M Novec 4200, 3M Novec 4300, 3M FC-4432, 3M FC-4430, or 3M FC-4434. After the aqueous phase and the sealant phase (e.g., oil phase) are changed, the aqueous phase is removed. The plurality of reaction vessels are moved to a digital counting device, such as a fluorescence microscope and the presence or absence of the detectable signal is detected. The detection of the presence of the detectable signal indicates the presence of a single molecule of analyte in the sample. In some embodiments, the detectable signal is detected using an optical microscope, such as a fluorescence microscope to acquire fluorescence images. In some embodiments, the detectable signal is detected using a fluorescence microscope to acquire fluorescence images.

In some embodiments, the plurality of reaction vessels can be a microwell array or nanowell array. In some embodiments, the microwell array or nanowell array has a diameter of at least about 4 mm, at least about 5 mm, at least about 6 mm, at least about 7 mm, at least about 8 mm, at least about 9 mm, or at least about 10 mm. In some embodiments, the microwell array has a diameter of 6 mm. In some embodiments, the microwell array or nanowell array contains approximately 100,000 to approximately 1,000,000 wells, approximately 200,000 to approximately 750,000 wells, or approximately 300,000 to approximately 500,000 wells. In some embodiments, the microwell array contains about 100,000, about 200,000, about 300,000, about 350,000, about 375,000, about 400,000, about 425,000, about 450,000, about 475,000, about 500,000, about 600,000, about 700,000, about 800,000, about 900,000, or about 1,000,000 wells. In some embodiments, the microwell array contains 400,000 wells. In some embodiments, the wells can have at least about 1 µM diameter, at least about 2 µM diameter, at least about 3 µM diameter, at least about 4 µM diameter, at least about 5 µM diameter, at least about 6 µM diameter, at least about 7 µM diameter, at least about 8 µM diameter, at least about 9 µM diameter, or at least about 10 µM diameter at the bottom of the well. In some embodiments, the plurality of reaction vessels can be a microwell array or nanowell array having a diameter of 6 mm and containing approximately 400,000 wells having a 5 µm diameter at the bottom of the well.

Following complex formation between the immobilized first specific binding member and the analyte, any unbound analyte may be removed from the vicinity of the first specific binding member along with the sample while the complex of the first specific binding member and the analyte may be retained due to its association with the solid support. Optionally, the solid support may be contacted with a wash buffer to remove any molecules non-specifically bound to the solid support.

After the first contacting step, and the optional removal of sample and/or optional wash steps, the complex of the first specific binding member and the analyte may be contacted with a second specific binding member, thereby leading to the formation of a sandwich complex in which the analyte is bound by the two binding members. An optional mixing of the second member with the first specific binding member-analyte complex may be carried out during the second contacting step. In some embodiments, immobilization of the analyte molecules with respect to a surface may aid in removal of any excess second specific binding members from the solution without concern of dislodging the analyte molecule from the surface. In some embodiments, the second specific binding member may include signal generating compound, attached thereto.

As noted above, the second contacting step may be carried out in conditions sufficient for binding interaction between the analyte and the second specific binding member. Following the second contacting step, any unbound second specific binding member may be removed, followed by an optional wash step. In some embodiments, the second specific binding member not bound to the analyte bound to the first specific binding member is removed before spatially segregating at least a portion of the solid support-first specific binding member-analyte-second specific binding member complexes into a plurality of separate locations.

In some embodiments, the signal generating compound can be alkaline phosphatase or β-galactosidase (beta-Gal). In some embodiments, the signal generating substrate can be a fluorescent substrate for the signal generating compound. For example, the signal generating substrate can be 4-methylumbelliferyl phosphate (MUP), fluorescein diphosphate (FDP), 6,8-Difluoro-4-Methylumbelliferyl Phosphate (DiFMUP), or 9H-(1,3-Dichloro-9,9-Dimethylacridin-2-One-7-yl) Phosphate (DDAO Phosphate). In some embodiments, the method further includes an inhibitor of the signal generating compound in the reaction mixture. In some embodiments, the inhibitor is levamisole.

In some embodiments, the method further includes incubating the mixture for a period of time before adding to the mixture one or more second specific binding members or after adding to the mixture one or more second specific binding members, wherein the period of time is an incubation period and is about 40 minute to about 300 minutes. In some embodiments, the fluid sample is serum, plasma or a whole blood sample.

In some embodiments, the method further includes contacting the fluid sample with one or more detergents, a surfactant, a nonpolar solvent, sonication, heating, or combination thereof, prior to contacting the fluid sample to the plurality of solid supports. In some embodiments, the method further includes the step of calculating a cut-off value using the formula: CO=2S/N, S/N CO=2 S/N, S/N ratio was calculated % signal from serum specimen with analyte divided by % signal from serum specimen without analyte. In some embodiments, the solid support is a magnetic solid support.

The present disclosure describes methods of determining the presence or absence of a single molecule of an analyte in a fluid sample. The method includes contacting the fluid sample containing or suspected of containing the analyte with a plurality of solid supports to create a mixture. Each solid support includes at least one first specific binding member capable of binding to the analyte thereby producing solid support-first specific binding member-analyte complexes. The solid support-first specific binding member-analyte complexes in the mixture are washed with a first wash buffer to remove any solid support-first specific binding member not bound to the analyte thereby producing a washed mixture. The one or more second specific binding members capable of binding to the analyte are added to the washed mixture thereby producing solid support-first specific binding member-analyte-second specific binding member complexes. The second specific binding member comprises a signal generating compound attached thereto. The solid support-first specific binding member-analyte-second specific binding member complexes are washed with a second wash buffer to remove any second specific binding member not bound to the analyte bound to the first specific binding member thereby producing washed solid support complexes. A signal generating substrate is added to the washed solid support complexes. The signal generating compound and the signal generating substrate produce a detectable signal. At least a portion of the washed solid support complexes are spatially segregating into a plurality of separate location. The plurality of separation locations includes a microwell array, as described above. The microwells or nanowells are covered with a sealant, e.g., heavy fluorinated oil. The aqueous phase and the sealant phase (e.g., oil phase) are changed. The presence or absence of the detectable signal is detected using a digital counting device. The detection of the presence of the detectable signal indicates the presence of a single molecule of the analyte in the sample. In the improved method, a colorant is added before or after spatially segregating the washed solid support complexes into a plurality of separate locations (i.e., femtoliter chamber formation).

In some embodiments, the sensitivity of detection of the analyte is at least about 0.1 fM to at least about 10 fM, at least about 0.5 mIU/mL, or at least about 0.24 pg/mL. In some embodiments, the sensitivity of detection of the analyte is at least about 0.05 fM, at least about 0.06 fM, at least about 0.07 fM, at least about 0.08 fM, at least about 0.09 fM, at least about 0.10 fM, at least about 0.11 fM, at least about 0.12 fM, at least about 0.13 fM, at least about 0.14 fM, at least about 0.15 fM, at least about 0.5 fM, at least about 1.0, at least about 5 fM, at least about 10 fM, at least about 20 fM, at least about 30 fM, at least about 40 fM, at least about 50 fM, at least about 60 fM, at least about 70 fM, at least about 80 fM, at least about 90 fM, or at least about 100 fM.

For example, the disclosed methods may be used for measuring or detecting an analyte present in a biological sample or for diagnosing a patient or screening a blood supply.

In exemplary cases, the method may include contacting the sample with a first specific binding member ("binding members" alternately referred to as "specific binding members," and as described below), where the first specific binding member is immobilized on a solid support and where the first specific binding member specifically binds to the analyte; contacting the analyte with a second specific binding member, which second specific binding member specifically binds to the analyte and which second specific binding member includes a signal generating compound or signal generating substrate described below.

In certain cases, the first specific binding member may be immobilized on a solid support. The solid support having a surface on which the binding reagent (such as one or more specific binding members) is immobilized may be any convenient surface in planar or non-planar conformation, such as a surface of a microfluidic chip, an interior surface of a chamber, an exterior surface of a bead (as defined herein), or an interior and/or exterior surface of a porous bead. For example, the first specific binding member may be attached covalently or non-covalently to a bead, e.g., latex, agarose, sepharose, streptavidin, tosylactivated, epoxy, polystyrene, amino bead, amine bead, carboxyl bead, or the like. In certain embodiments, the bead may be a particle, e.g., a microparticle. In some embodiments, the microparticle may be between about 0.1 nm and about 10 microns, between about 50 nm and about 5 microns, between about 100 nm and about 1 micron, between about 0.1 nm and about 700 nm, between about 500 nm and about 10 microns, between about 500 nm and about 5 microns, between about 500 nm and about 3 microns, between about 100 nm and 700 nm, or between about 500 nm and 700 nm. For example, the microparticle may be about 4-6 microns, about 2-3 microns, or about 0.5-1.5 microns. Particles less than about 500 nm are sometimes considered nanoparticles. Thus, the microparticle optionally may be a nanoparticle between about 0.1 nm and about 500 nm, between about 10 nm and about 500 nm, between about 50 nm and about 500 nm, between about 100 nm and about 500 nm, about 100 nm, about 150 nm, about 200 nm, about 250 nm, about 300 nm, about 350 nm, about 400 nm, about 450 nm, or about 500 nm.

In certain embodiments, the bead may be a magnetic bead or a magnetic particle. Magnetic beads/particles may be ferromagnetic, ferrimagnetic, paramagnetic, superparamagnetic or ferrofluidic. Exemplary ferromagnetic materials include Fe, Co, Ni, Gd, Dy, $CrO_2$, MnAs, MnBi, EuO, NiO/Fe. Examples of ferrimagnetic materials include $NiFe_2O_4$, $CoFe_2O_4$, $Fe_3O_4$ (or $FeO \cdot Fe_2O_3$). Beads can have a solid core portion that is magnetic and is surrounded by one or more non-magnetic layers. Alternately, the magnetic portion can be a layer around a non-magnetic core. The solid support on which the first specific binding member is immobilized may be stored in dry form or in a liquid. The magnetic beads may be subjected to a magnetic field prior to or after contacting with the sample with a magnetic bead on which the first specific binding member is immobilized.

After the contacting step, the sample and the first specific binding member may be incubated for a sufficient period of time to allow for the binding interaction between the binding member and analyte to occur. In addition, the incubating may be in a binding buffer that facilitates the specific binding interaction. The binding affinity and/or specificity of the first specific binding member and/or the second specific binding member may be manipulated or altered in the assay by varying the binding buffer. In some embodiments, the binding affinity and/or specificity may be increased by varying the binding buffer. In some embodiments, the binding affinity and/or specificity may be decreased by varying the binding buffer.

The binding affinity and/or specificity of the first specific binding member and/or the second specific binding member may be measured using the disclosed methods described below. In some embodiments, the one aliquot of sample is assayed using one set of conditions and compared to another aliquot of sample assayed using a different set of conditions, thereby determining the effect of the conditions on the binding affinity and/or specificity. For instance, changing or altering the condition can be one or more of removing the target analyte from the sample, adding a molecule that competes with the target analyte or the ligand for binding, and changing the pH, salt concentration, or temperature. Additionally or alternatively, a duration of time can be the variable and changing the condition may include waiting for a duration of time before again performing the detection methods.

The binding buffer may include molecules standard for antigen-antibody binding buffers such as, albumin (e.g., BSA), non-ionic detergents (Tween-20, Triton X-100), and/or protease inhibitors (e.g., PMSF). In certain cases, the binding buffer may be added to the microfluidic chip, chamber, etc., prior to or after adding the sample. In certain cases, the first specific binding member may be present in a binding buffer prior to contacting with the sample. The length of time for binding interaction between the binding member and analyte to occur may be determined empirically and may depend on the binding affinity and binding avidity between the binding member and the analyte. In certain embodiments, the contacting or incubating may be for a period of 5 sec to 1 hour, such as, 10 seconds to 30 minutes, or 1 minute to 15 minutes, or 5 minutes to 10 minutes, e.g., 10 seconds, 15 seconds, 30 seconds, 1 minute, 5 minutes, 10 minutes, 15 minutes, 30 minutes, 45 minutes, 1 hour or 2 hours. Other conditions for the binding interaction, such as, temperature, salt concentration, may also be determined empirically or may be based on manufacturer's instructions. For example, the contacting may be carried out at room temperature (21° C.-28° C., e.g., 23° C.-25° C.), 37° C., or 4° C. In certain embodiments, an optional mixing of the sample with the first specific binding member may be carried out during the contacting step.

Following complex formation between the immobilized first specific binding member and the analyte, any unbound analyte may be removed from the vicinity of the first specific binding member along with the sample while the complex of the first specific binding member and the analyte may be retained due to its association with the solid support. Optionally, the solid support may be contacted with a wash buffer to remove any molecules non-specifically bound to the solid support.

After the first contacting step, and the optional removal of sample and/or optional wash steps, the complex of the first specific binding member and the analyte may be contacted with a second specific binding member, thereby leading to the formation of a sandwich complex in which the analyte is bound by the two binding members. An optional mixing of the second member with the first specific binding member-analyte complex may be carried out during the second contacting step. In some embodiments, immobilization of the analyte molecules with respect to a surface may aid in removal of any excess second specific binding members from the solution without concern of dislodging the analyte molecule from the surface. In some embodiments, the second specific binding member may include a signal generating compound, attached thereto.

As noted above, the second contacting step may be carried out in conditions sufficient for binding interaction between the analyte and the second specific binding member. Following the second contacting step, any unbound second specific binding member may be removed, followed by an optional wash step. Any unbound second specific binding member may be separated from the complex of the first specific binding member-analyte-second specific binding member by a suitable means such as, droplet actuation, electrophoresis, electrowetting, dielectrophoresis, electrostatic actuation, electric field mediated, electrode mediated, capillary force, chromatography, centrifugation, or aspiration. Upon removal of any unbound second specific binding member from the vicinity of the complex of the first specific binding member-analyte-second specific binding member, the signal generating compound attached to the second specific binding member present in the complex of the first specific binding member-analyte-second specific binding member may be separated by a suitable means.

In certain embodiments, the separation of the signal generating compound from the first specific binding member-analyte-second specific binding member complex is carried out under conditions that do not result in disruption of the complex, resulting in release of only the signal generating compound from the complex. In other cases, the separation of the signal generating compound from the first specific binding member-analyte-second specific binding member complex is carried out under conditions that may result in disruption of the complex, resulting in release of the signal generating compound, as well as one or more of the second specific binding member, the analyte, the first specific binding member from the complex.

The number of signal generating compound molecules can be correlated to the number of analyte molecules in the complex which are proportional to the concentration of the analyte in the sample. In certain embodiments, the correlation between the signal generating compound and the analyte concentration may be direct (higher number of signal generating compound molecules relates to higher analyte concentration). In embodiments where a signal generating compound-tagged competitor or analyte, such as a tracer (as defined herein), is combined with the sample, which signal generating compound-tagged competitor or analyte competes with the analyte in the sample for binding to the first specific binding member, the correlation between the signal generating compound and the analyte concentration may be inverse (lower number of signal generating compound molecules relates to higher analyte concentration). The correlation between the number of signal generating compound molecules and analyte concentration, whether direct or inverse, may be linear or logarithmic.

In certain embodiments, the simultaneous analysis of multiple analytes in a single sample may be performed by using a plurality of different first and second specific binding members where a pair of first and second specific binding members is specific to a single analyte in the sample. In these embodiments, the signal generating compound associated with the second specific binding member of a first pair of first and second specific binding members specific to a single analyte may be distinguishable from the signal generating compound or signal generating substrate associated with the second specific binding member of a second pair of first and second specific binding members specific to a different analyte. As noted above, a first signal generating compound may be distinguishable from second signal generating compound or signal generating substrate based on difference in substrates.

In some embodiments, the concentration of an analyte in the fluid sample that may be substantially accurately determined is less than about 5000 fM (femtomolar), less than about 3000 fM, less than about 2000 fM, less than about 1000 fM, less than about 500 fM, less than about 300 fM, less than about 200 fM, less than about 100 fM, less than about 50 fM, less than about 25 fM, less than about 10 fM, less than about 5 fM, less than about 2 fM, less than about 1 fM, less than about 500 aM (attomolar), less than about 100 aM, less than about 10 aM, less than about 5 aM, less than about 1 aM, less than about 0.1 aM, less than about 500 zM (zeptomolar), less than about 100 zM, less than about 10 zM, less than about 5 zM, less than about 1 zM, less than about 0.1 zM, or less.

In some cases, the limit of detection (e.g., the lowest concentration of an analyte which may be determined in solution) is about 100 fM, about 50 fM, about 25 fM, about 10 fM, about 5 fM, about 2 fM, about 1 fM, about 500 aM (attomolar), about 100 aM, about 50 aM, about 10 aM, about 5 aM, about 1 aM, about 0.1 aM, about 500 zM (zeptomolar), about 100 zM, about 50 zM, about 10 zM, about 5 zM, about 1 zM, about 0.1 zM, or less. In some embodiments, the concentration of analyte in the fluid sample that may be substantially accurately determined is between about 5000 fM and about 0.1 fM, between about 3000 fM and about 0.1 fM, between about 1000 fM and about 0.1 fM, between about 1000 fM and about 0.1 zM, between about 100 fM and about 1 zM, between about 100 aM and about 0.1 zM, or less.

The upper limit of detection (e.g., the upper concentration of an analyte which may be determined in solution) is at least about 100 fM, at least about 1000 fM, at least about 10 pM (picomolar), at least about 100 pM, at least about 100 pM, at least about 10 nM (nanomolar), at least about 100 nM, at least about 1000 nM, at least about 10 µM, at least about 100 µM, at least about 1000 µM, at least about 10 mM, at least about 100 mM, at least about 1000 mM, or greater.

In some cases, the presence and/or concentration of the analyte in a sample may be detected rapidly, usually in less than about 1 hour, e.g., 45 minutes, 30 minutes, 15 minutes, 10 minutes, 5 minutes, 1 minute, or 30 seconds.

In some embodiments, one or more detected signals correspond to a binding event of a binding member to an analyte. In some embodiments, one detected signal corresponds to a binding event of a binding member to an analyte. In some embodiments, two or more detected signals correspond to a binding event of a binding member to an analyte.

In some embodiments, the solid support comprising the first specific binding member and second specific binding member are added sequentially or simultaneously to the sample.

a) Colorant

In the present invention, a colorant is added before or after femto-liter chamber formation. The colorant suppresses the glow of the fluorescent substance in the upper phase without the need for the time consuming step of removing the aqueous phase. In some embodiments, the colorant is added simultaneously with the signal generating substrate. In some embodiments, the colorant is added to the washed solid support complexes before the signal generating substrate. In some embodiments, the colorant is added to the washed solid support complexes after the signal generating substrate. In some embodiments, the colorant is added to the displaced aqueous phase or to the sealant phase (e.g., oil phase).

Figure 12A:
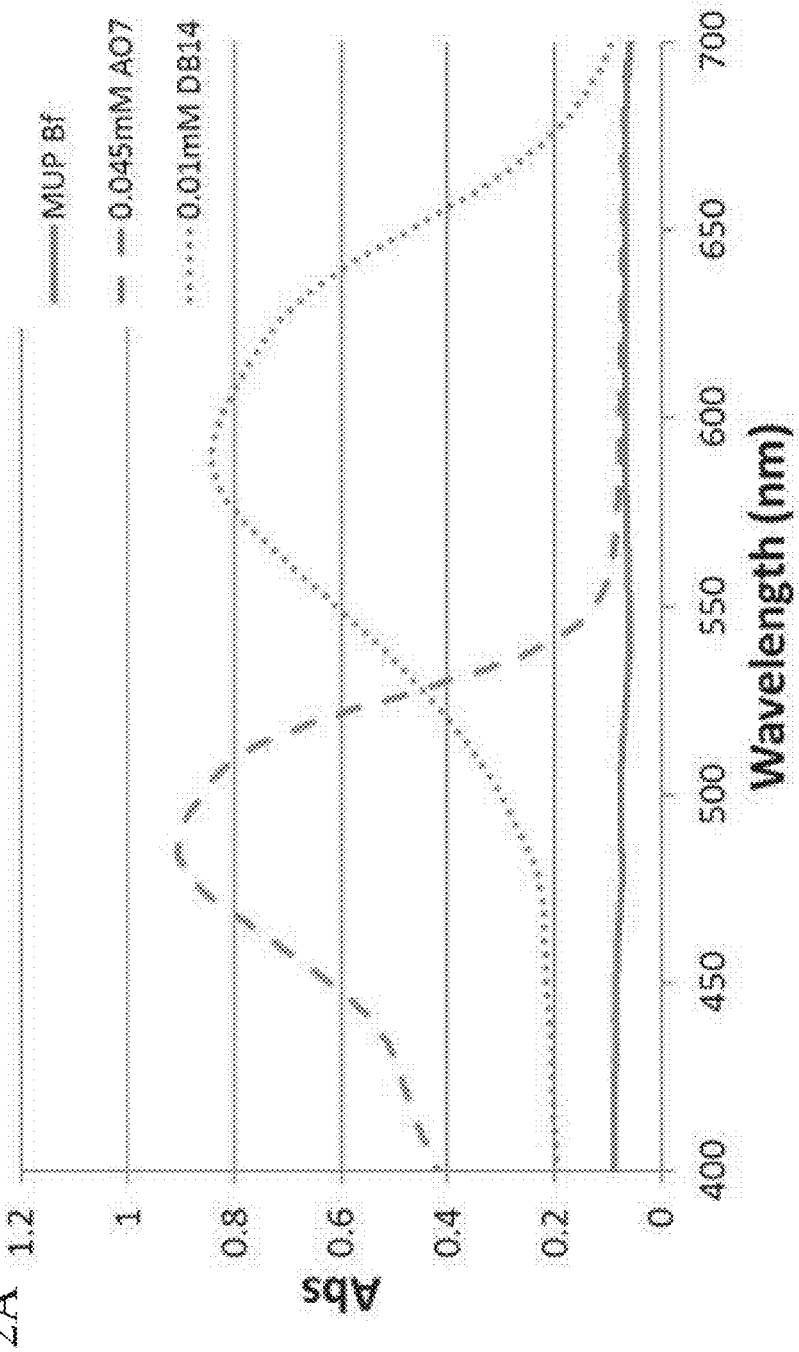
FIGS. 12A and 12B show the absorbing spectra of the combination of 15 mM Acid Orange 7 (AO7) and 4 mM Direct Blue 14 (DBu14) (FIG. 12A) and the emission and excitation spectra of Fluorescein (FIG. 12B). Note; emission peak is located around the valley between AO7 and DBu14.
Figure 12B:
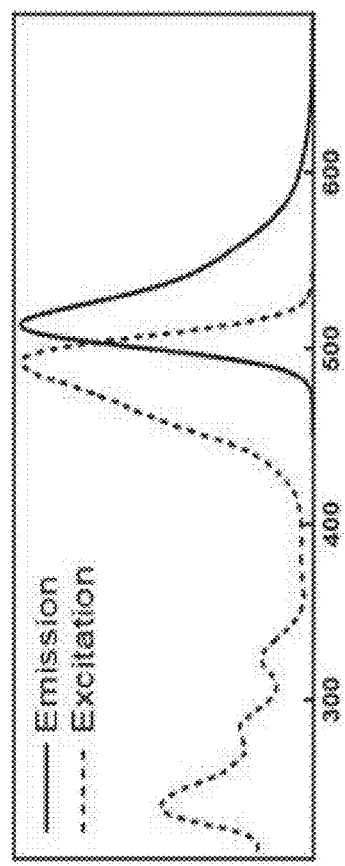

In some embodiments, the colorant is a black colorant, such as a black or dark colored ink, such as a black ink, dye component, or pigment-based composition. In some embodiments, the colorant is India ink, acid black 2, acid orange 7, direct Blue 14, or combination thereof. Any suitable dye components can be selected depending on the fluorescent material used for the signal detection on the digital measurement technique. For example, a combination of AO7 and DBu14 reagents can be used as this combination may influence the fluorescein signal effectively in the femto-liter chambers. In some embodiments, a dye combination can be selected to observe the target (favorable) emission signal for any assay (see e.g., FIG. 12).

i) India Ink

India ink (also known as Chinese ink) is a simple black or colored ink composed of a variety of fine soot, known as lampblack, combined with water to form a liquid. The carbon molecules are in a colloidal suspension and form a waterproof layer after drying. A binding agent such as gelatin or, more commonly, shellac may be added to make the ink more durable once dried, however no binding agent is necessary. India ink may be in bottled form or solid form as an inkstick (most commonly, a stick), which must be ground and mixed with water before use. India ink may be waterproof or non-waterproof if a binder is used.

ii) Acid Black 2

Figure 9B:
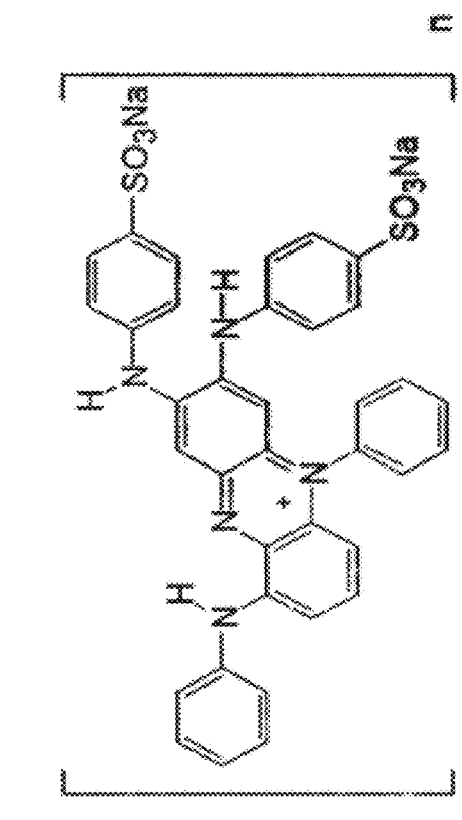
FIG. 9B shows the chemical structure of Acid black 2 ("ABk2").
Figure 9D:
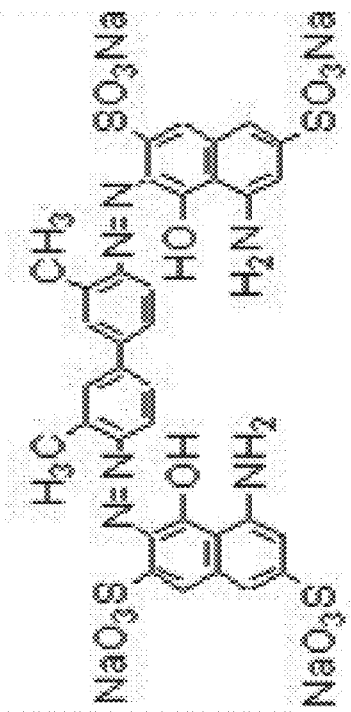
FIG. 9D shows the chemical structure of Direct Blue 14 ("DBu14").

Acid black 2, also known as nigrosin, is a dark black pigment (or dye) obtained primarily from aniline. The chemical structure of acid black 2 is shown in FIG. 9B.

iii) Acid Orange 7

Figure 9A:
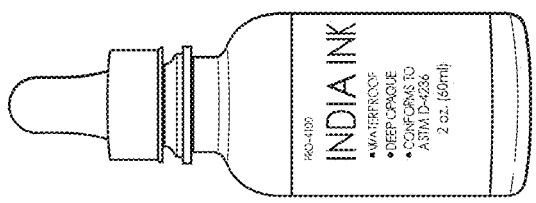
FIG. 9A shows an example of India Ink.
Figure 9C:
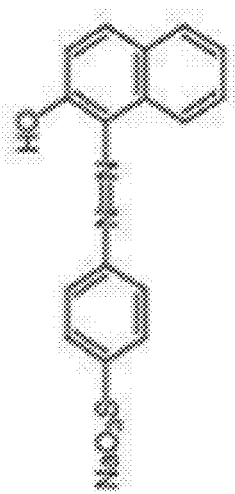
FIG. 9C shows the chemical structure of Acid Orange 7 ("AO7").

Acid orange 7 ("AO7") also known as 2-naphthol orange, Orange II or acidic orange II, is a dye produced by a coupling reaction between 2-Naphthol, or β-naphthol, and the diazonium compound of sulfanilic acid. The chemical structure of acid orange 7 is shown in FIG. 9C.

iv) Direct Blue 14

Direct Blue 14 ("DBU14"), also known as TRYPAN BLUE and VisionBlue, is a diazo-naphthalene sulfonate that is widely used as a stain. The chemical structure of Direct Blue 14 is shown in FIG. 9C.

b) "Addition" Method

The colorant can be used to reduce background fluorescence using an "Addition" method. The "Addition" method includes adding a colorant to the aqueous phase or aqueous phase solution after the aqueous phase is displaced by sealant (e.g., oil) (i.e., the upper liquid phase including a fluorescent substance), or adding a colorant to the sealant (e.g., oil), to effectively reduce the background fluorescence noise in the femto-liter chamber. The colorant suppresses the glow of the fluorescent substance in the upper liquid phase or aqueous phase. For example, a "Black Ink Addition" method involves adding black ink to the aqueous phase or aqueous phase solution after the displacement of the aqueous phase by the sealant (e.g., oil), or to the sealant (e.g., oil), thus the time consuming step of removing the aqueous phase solution is not necessary.

c) "Pre-Mix" Method

Figure 7A:
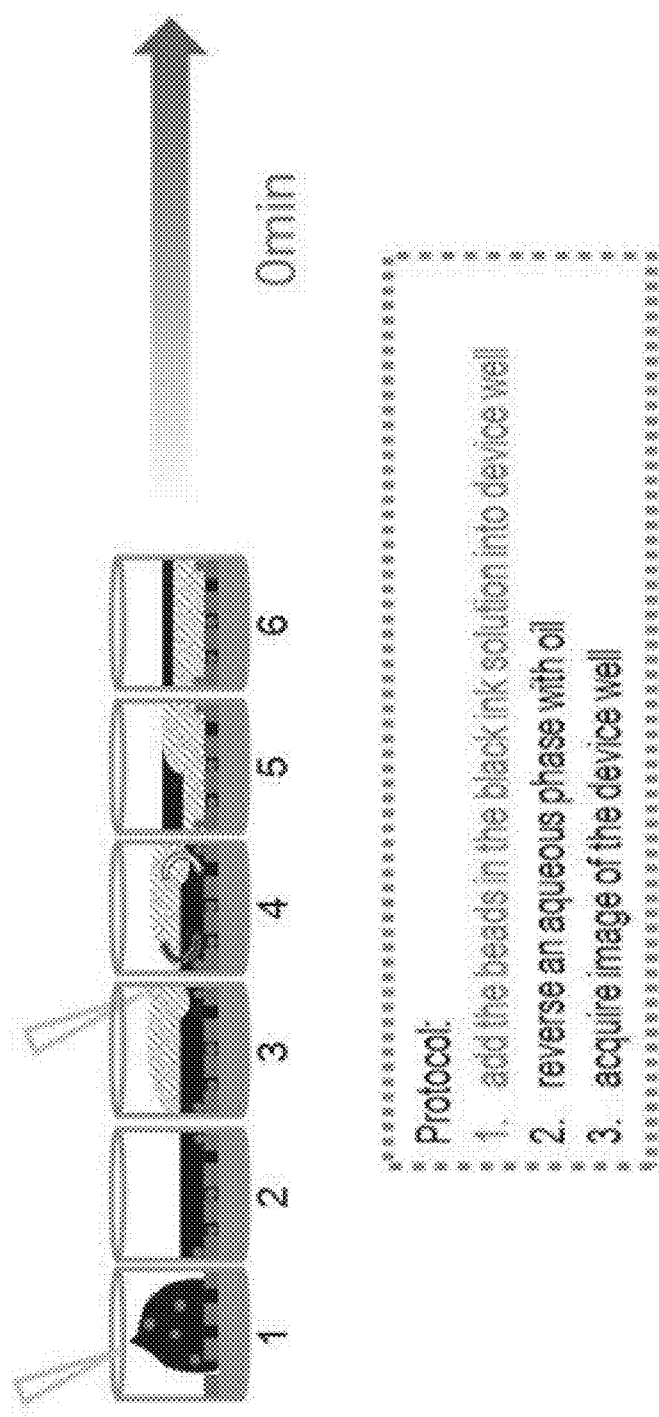
FIG. 7A shows an improved procedure of a fluorescent digital ELISA assay using black ink mixing with the solution for enzymatic reaction.
Figure 7B:
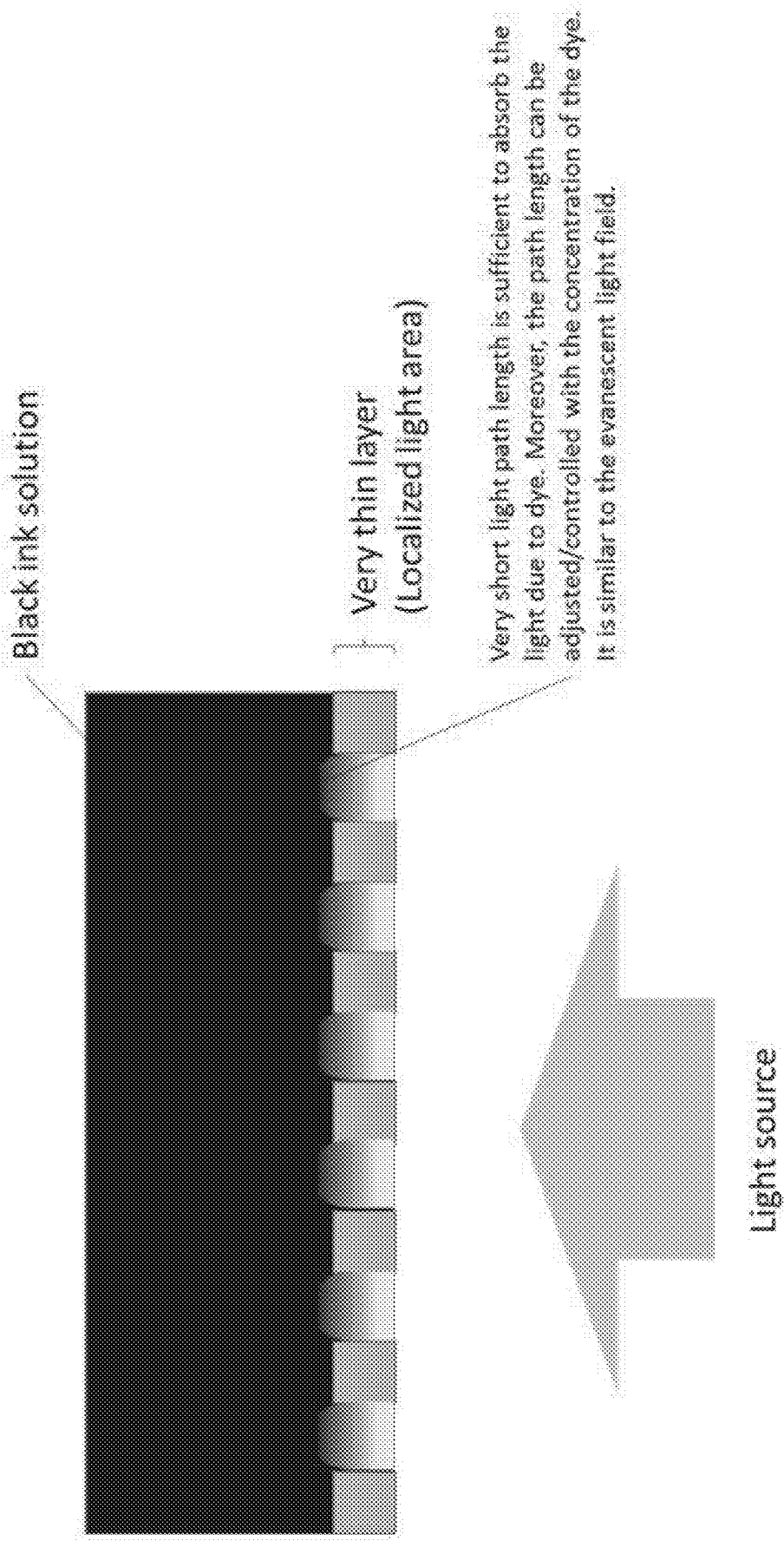
FIG. 7B shows a schematic of how the disclosed methods can limit the light area similar to an evanescent light detection system.

The colorant can be used to reduce background fluorescence using a "Pre-Mix" method (see FIG. 7A). The "Pre-Mix" method does not need any additional procedure after sealant (e.g., oil) sealing because the aqueous phase or aqueous phase solution in itself is a dark color, such as a black color, thus the procedure is simplified and more efficient as only inverting the sealant (e.g., oil) is needed. The colorant, such as black ink, is added with a signal generating substrate to the aqueous phase or aqueous phase solution that include washed solid support complexes, that includes a signal generating compound attached thereto, or added to an aqueous phase or aqueous phase solution containing the signal generating compound or washed solid support complexes before the signal generating substrate is added to the washed solid support complexes. Pre-mixing the colorant, such as black ink, with the aqueous phase or aqueous phase solution could suppress the glow of fluorescein even though the upper liquid phase (aqueous phase) includes the fluorescent substance. For example, a "Black Ink Pre-Mix" method involves mixing black ink with the reacted signal generating compound/signal generating substrate (i.e., enzyme/substrate) solution, thus the time consuming step of removing the aqueous phase solution is not necessary.

d) Sealant

In the present invention, the reaction vessels can be sealed or covered by the addition of one or more solvents ("solvent well sealing") using a sealant, such as a hydrophilic or a hydrophobic solvent that has a density that is heavier than the aqueous phase. Hydrophilic solvents that can be used include hydrophilic alcohols, hydrophilic ethers, ketones, nitrile solvents, dimethyl sulfoxides, and N,N-dimethylformamides, or mixtures thereof. Examples of hydrophilic alcohols include ethanol, methanol, propanol, and glycerin. Examples of hydrophilic ethers include tetrahydrofuran, polyethylene oxide, and 1,4-dioxane. Examples of ketone include acetone and methyl ethyl ketone. Examples of the nitrile solvents include acetonitrile. Hydrophobic solvents that can be used include hydrocarbons, unsaturated hydrocarbons, aromatic hydrocarbons, silicone oils, perfluorocarbons, halogen solvents, hydrophobic ionic liquids and mixtures thereof. Examples of saturated hydrocarbons include alkanes, such as decane and hexadecane. Examples of unsaturated hydrocarbon include squalene. Examples of aromatic hydrocarbon include benzene and toluene. Examples of perfluorocarbon encompass Fluorinert®, FC-40, FC-72, FC-84, FC-77, FC-3255, FC-3283, FC-43, FC-70), 3M Novec 4200, 3M Novec 4300, 3M FC-4432, 3M FC-4430, or 3M FC-4434. Examples of halogen solvents encompass chloroform, methylene chloride, and chlorobenzene. The hydrophobic ionic liquid denotes ionic liquid which is not dissociated at least in water. Examples of ionic liquids include 1-butyl-3-methylimidazolium hexafluorophosphate.

e) Signal Generating Compound and Signal Generating Substrate

The detection of the analyte is correlated by the detectable product or detectable label, namely, a signal, generated by the at least one signal generating compound and the at least one signal generating substrate. In some embodiments, the at least one signal generating compound is an enzyme and the at least one signal generating substrate is a substrate for the enzyme. In some embodiments, the substrate for the enzyme is a colorimetric, fluorogenic (non-fluorescent) substrate or a chromogenic substrate. In some embodiments, the detectable signal is a fluorescent signal. For example, the enzyme may be a, polynucleotidase, arginase, adenase, aminopolypeptidase, pepsin, lipases, catalase, tyrosinases, alcohol dehydrogenase, succinic dehydrogenase, diaphorase, glyoxalase, aldolase, glucose oxidase, horseradish peroxidase, galactosidase (such as beta-galactosidase), phosphatases, phosphorylases and hexokinases or combinations thereof. Examples of enzymatic substrates that can be used include a chemiluminescent substrate such as CDP-Star®, (disodium 4-chloro-3-(methoxyspiro{1,2-dioxetane-3,2'-(5'-chloro)tricyclo[3.3.1.1.s-up.3,7]decane}-4-yl)phenyl phosphate), CSPD®, or (disodium 3-(4-methoxyspiro{1,2-dioxetane-3,2-(5'-chloro)tricyclo[3.3.1.1-.sup.3,7]decane}-4-yl)phenyl phosphate); a luminescent substrate such as p-nitrophenyl phosphate, 5-bromo-4-chloro-3-indolyl phosphate (BCIP), 4-nitro blue tetrazolium chloride (NBT), or iodonitrotetrazolium (INT); a fluorescent substrate such as 4-methylumbelliferyl phosphate (4-MUP); and a chromogenic substrate such as 5-bromo-4-chloro-3-indolyl phosphate (BCIP), disodium 5-bromo-6-chloro-indolyl phosphate, or p-nitrophenyl phosphate.

In some aspects, enzymes that can be used include those which contain an inhibitor molecule (such as a protein, peptide, etc.) bound to a site other than the active binding site of the enzyme. Such inhibitor molecules change the conformation of the active binding site of the enzyme and prevent it from binding to the substrate. Examples of inhibitor molecules include protease inhibitors. The inhibitor can be removed from the enzyme using routine techniques known in the art to allow the enzyme to bind to the substrate thus allowing a signal generating reaction to occur.

In some embodiments, the enzyme can convert a non-fluorescent substrate into a fluorescent substrate. In some embodiments, the enzyme can generate color using a chromogenic substrate.

3. METHODS FOR REDUCING FLUORESCENCE BACKGROUND NOISE IN A FLUORESCENT DIGITAL IMMUNOASSAY

The disclosed methods also relate to methods for reducing fluorescence background noise in a fluorescent digital immunoassay used to detect an analyte in a sample, as described above. Solid phase material, such as CYTOP, cyclic olefin polymers (COP), and other resins, have some auto fluorescence which affects the detection by increasing background noise. The disclosed methods use a digital counting device that includes a black device. The black device includes a solid phase material comprising carbon black or a black film sheet attached to a transparent device. The solid phase material comprising carbon black or a black film sheet can reduce the auto fluorescence. In some embodiments, the solid phase material is CYTOP, cyclic olefin polymers (COP), or polydimethylsiloxane (PDMS). In some embodiments, the solid phase material includes CYTOP®, cyclic olefin polymers (COP), polydimethylsiloxane (PDMS), poly(methyl methacrylate), Polycarbonate (PC), or Polypropylene (PP). In some embodiments, the black device is thick enough so that excitation light to the nanowells and signal light from the nanowells can be transmitted. In some embodiments, the device thickness is between about 0.1 mm and about 1 mm, between about 0.5 mm and about 1 mm, about 0.1 mm and about 0.75 mm, about 0.5 mm and about 0.75 mm. In some embodiments, the device thickness is less than about 1 mm, less than about 0.9 mm, less than about 0.8 mm, less than about 0.7 mm, less than about 0.6 mm, less than about 0.5 mm, less than about 0.4 mm, less than about 0.3 mm, less than about 0.2 mm, or less than about 0.1 mm.

In some embodiments, the method includes contacting a fluid sample containing or suspected of containing the analyte with a plurality of solid supports to create a mixture, wherein each solid support comprises one or more first specific binding member capable of binding to the analyte thereby producing solid support-first specific binding member-analyte complexes; washing the solid support-first specific binding member-analyte complexes in the mixture with a first wash buffer to remove any solid support-first specific binding member not bound to the analyte thereby producing a washed mixture; adding to the washed mixture one or more second specific binding members capable of binding to the analyte thereby producing solid support-first specific binding member-analyte-second specific binding member complexes, wherein the second specific binding member comprises a signal generating compound attached thereto; washing the solid support-first specific binding member-analyte-second specific binding member complexes with a second wash buffer to remove any second specific binding member not bound to the analyte bound to the first specific binding member thereby producing washed solid support complexes; adding to the washed solid support complexes a signal generating substrate, wherein the signal generating compound and the signal generating substrate produce a detectable signal; spatially segregating at least a portion of the washed solid support complexes into a plurality of separate locations, wherein the plurality of separation locations comprises a plurality of reaction vessels and wherein the washed solid support complexes are present in an aqueous phase; covering the plurality of reaction vessels with a sealant (e.g., oil), wherein the aqueous phase is displaced by the sealant (e.g., oil) in the reaction chamber; and detecting the presence or absence of the detectable signal using a digital counting device, wherein detection of the presence of the detectable signal indicates the presence of a single molecule of analyte in the sample. In some embodiments, the method further includes adding a colorant, as described above. In some embodiments, the colorant is added to the washed solid support complexes simultaneously with the signal generating substrate, added to the washed solid support complexes before the signal generating substrate, added to the washed solid support complexes after the signal generating substrate, added to the displaced aqueous phase, or added to the sealant (e.g., oil), as described above.

4. SPECIFIC BINDING MEMBERS

As will be appreciated by those in the art, the binding members will be determined by the analyte to be analyzed. Binding members for a wide variety of target molecules are known or can be readily found or developed using known techniques. For example, when the target analyte is a protein, the binding members may include proteins, particularly antibodies or fragments thereof (e.g., antigen-binding fragments (Fabs), Fab' fragments, F(ab')$_2$ fragments, recombinant antibodies, chimeric antibodies, single-chain Fvs ("scFv"), single chain antibodies, single domain antibodies, such as variable heavy chain domains ("VHH"; also known as "VHH fragments") derived from animals in the Camelidae family (VHH and methods of making them are described in Gottlin et al., *Journal of Biomolecular Screening*, 14:77-85 (2009)), recombinant VHH single-domain antibodies, and $V_{NAR}$ fragments, disulfide-linked Fvs ("sdFv"), and anti-idiotypic ("anti-Id") antibodies, and functionally active epitope-binding fragments of any of the above, full-length polyclonal or monoclonal antibodies, antibody-like fragments, etc.), other proteins, such as receptor proteins, Protein A, Protein C, or the like. In case where the analyte is a small molecule, such as, steroids, bilins, retinoids, and lipids, the first and/or the second specific binding member may be a scaffold protein (e.g., lipocalins) or a receptor. In some cases, binding member for protein analytes may be a peptide. For example, when the target analyte is an enzyme, suitable binding members may include enzyme substrates and/or enzyme inhibitors which may be a peptide, a small molecule and the like. In some cases, when the target analyte is a phosphorylated species, the binding members may comprise a phosphate-binding agent. For example, the phosphate-binding agent may comprise metal-ion affinity media such as those describe in U.S. Pat. No. 7,070,921 and U.S. Patent Application No. 2006/0121544.

When the target molecule is a carbohydrate, potentially suitable capture components (as defined herein) include, for example, antibodies, lectins, and selectins. As will be appreciated by those of ordinary skill in the art, any molecule that can specifically associate with a target molecule of interest may potentially be used as a binding member.

For certain embodiments, suitable target analyte/binding member complexes can include, but are not limited to, antibodies/antigens, antigens/antibodies, receptors/ligands, ligands/receptors, proteins/nucleic acid, enzymes/substrates and/or inhibitors, carbohydrates (including glycoproteins and glycolipids)/lectins and/or selectins, proteins/proteins, proteins/small molecules, etc.

In a particular embodiment, the first specific binding member and/or second specific binding member may be attached to a solid support via a linkage, which may comprise any moiety, functionalization, or modification of the support and/or binding member that facilitates the attachment of the binding member to the support. The linkage between the binding member and the support may include one or more chemical or physical (e.g., non-specific attachment via van der Waals forces, hydrogen bonding, electrostatic interactions, hydrophobic/hydrophilic interactions; etc.) bonds and/or chemical spacers providing such bond(s).

In certain embodiments, a solid support may also comprise a protective, blocking, or passivating layer that can eliminate or minimize non-specific attachment of non-capture components (e.g., analyte molecules, binding members) to the binding surface during the assay which may lead to false positive signals during detection or to loss of signal. Examples of materials that may be utilized in certain embodiments to form passivating layers include, but are not limited to: polymers, such as poly(ethylene glycol), that repel the non-specific binding of proteins; naturally occurring proteins with this property, such as serum albumin and casein; surfactants, e.g., zwitterionic surfactants, such as sulfobetaines; naturally occurring long-chain lipids; polymer brushes, and nucleic acids, such as salmon sperm DNA.

Certain embodiments utilize binding members that are proteins or polypeptides. As is known in the art, any number of techniques may be used to attach a polypeptide to a wide variety of solid supports. A wide variety of techniques are known to add reactive moieties to proteins, for example, the method outlined in U.S. Pat. No. 5,620,850. Further, methods for attachment of proteins to surfaces are known, for example, see Heller, Acc. Chem. Res. 23:128 (1990).

As explained herein, binding between the binding members and the analyte, is specific, e.g., as when the binding member and the analyte are complementary parts of a binding pair. In certain embodiments, the binding member binds specifically to the analyte. By "specifically bind" or "binding specificity," it is meant that the binding member binds the analyte molecule with specificity sufficient to differentiate between the analyte molecule and other components or contaminants of the test sample. For example, the binding member, according to one embodiment, may be an antibody that binds specifically to an epitope on an analyte. The antibody, according to one embodiment, can be any antibody capable of binding specifically to an analyte of interest. For example, appropriate antibodies include, but are not limited to, monoclonal antibodies, bispecific antibodies, minibodies, domain antibodies (dAbs) (e.g., such as described in Holt et al., (2014) *Trends in Biotechnology* 21:484-490), and including single domain antibodies sdAbs that are naturally occurring, e.g., as in cartilaginous fishes and camelid, or which are synthetic, e.g., nanobodies, VHH, or other domain structure), synthetic antibodies (sometimes referred to as antibody mimetics), chimeric antibodies, humanized antibodies, antibody fusions (sometimes referred to as "antibody conjugates"), and fragments of each, respectively. As another example, the analyte molecule may be an antibody and the first specific binding member may be an antigen and the second specific binding member may be a secondary antibody that specifically binds to the target antibody or the first specific binding member may be a secondary antibody that specifically binds to the target antibody and the second specific binding member may be an antigen.

In some embodiments, the binding member may be chemically programmed antibodies (cpAbs) (described in Rader (2014) *Trends in Biotechnology* 32:186-197), bispecific cpAbs, antibody-recruiting molecules (ARMs) (described in McEnaney et al., (2012) *ACS Chem. Biol.* 7:1139-1151), branched capture agents, such as a triligand capture agent (described in Millward et al., (2011) *J. Am. Chem. Soc.* 133:18280-18288), engineered binding proteins derived from non-antibody scaffolds, such as monobodies (derived from the tenth fibronectin type III domain of human fibronectin), affibodies (derived from the immunoglobulin binding protein A), DARPins (based on Ankyrin repeat modules), anticalins (derived from the lipocalins bilin-binding protein and human lipocalin 2), and cysteine knot peptides (knottins) (described in Gilbreth and Koide, (2012) *Current Opinion in Structural Biology* 22:1-8; Banta et al., (2013) Annu. Rev. Biomed. Eng. 15:93-113), WW domains (described in Patel et al., (2013) *Protein Engineering, Design & Selection* 26(4):307-314), repurposed receptor ligands, affitins (described in Béhar et al., (2013) 26:267-275), and/or Adhirons (described in Tiede et al., (2014) *Protein Engineering, Design & Selection* 27:145-155).

According to one embodiment in which an analyte is a biological cell (e.g., mammalian, avian, reptilian, other vertebrate, insect, yeast, bacterial, cell, etc.), the binding members may be ligands having specific affinity for a cell surface antigen (e.g., a cell surface receptor). In one embodiment, the binding member may be an adhesion molecule receptor or portion thereof, which has binding specificity for a cell adhesion molecule expressed on the surface of a target cell type. In use, the adhesion molecule receptor binds with an adhesion molecule on the extracellular surface of the target cell, thereby immobilizing or capturing the cell, the bound cell may then be detected by using a second specific binding member that may be the same as the first specific binding member or may bind to a different molecule expressed on the surface of the cell.

In some embodiments, the binding affinity between analyte molecules and binding members should be sufficient to remain bound under the conditions of the assay, including wash steps to remove molecules or particles that are non-specifically bound. In some cases, for example in the detection of certain biomolecules, the binding constant of the analyte molecule to its complementary binding member may be between at least about $10^4$ and about $10^6 M^{-1}$, at least about $10^5$ and about $10^9 M^{-1}$, at least about $10^7$ and about $10^9 M^{-1}$, greater than about $10^9$ $M^{-1}$, or greater.

5. EXEMPLARY TARGET ANALYTES

As will be appreciated by those in the art, any analyte that can be specifically bound by a first specific binding member and a second specific binding member may be detected and, optionally, quantified using methods and devices of the present disclosure.

In some embodiments, the analyte may be a biomolecule or biological molecule. Non-limiting examples of biomolecules and biological molecules include macromolecules such as, proteins, lipids, and carbohydrates. In certain instances, the analyte may be hormones, antibodies, growth factors, cytokines, enzymes, receptors (e.g., neural, hormonal, nutrient, and cell surface receptors) or their ligands, cancer markers (e.g., PSA, TNF-alpha), markers of myocardial infarction (e.g., troponin, creatine kinase, BNP, pro-BNP, NT-ProBNP, CK-MB, Galectin-3, and the like), thyroid markers (e.g., Anti-Tg, Anti-TPO, Free T3, Free T4, T-uptake, Total T3, Total T4, TSH), toxins, drugs (e.g., drugs of addiction), metabolic agents (e.g., including vitamins), and the like. Non-limiting embodiments of protein analytes include peptides, polypeptides, protein fragments, protein complexes, fusion proteins, recombinant proteins, phosphoproteins, glycoproteins, lipoproteins, or the like. In some embodiments, the analyte may be a biomarker, such as a biomarker for traumatic brain injury, sepsis, or coagulation, an analyte involved with general chemistry (e.g., ammonia, AST, cholesterol, etc.), a protein (e.g., transferrin, CRP, etc.), an analyte for therapeutic drug monitoring (e.g., Methotrexate), an analyte for transplant (e.g., tacrolimus), a drug of abuse, or a biomarker for genetic disorders.

In certain embodiments, the analyte may be a post-translationally modified protein (e.g., phosphorylated, methylated, glycosylated protein) and the first or the second specific binding member may be an antibody specific to a post-translational modification. A modified protein may be bound to a first specific binding member immobilized on a solid support where the first specific binding member binds to the modified protein but not the unmodified protein. In other embodiments, the first specific binding member may bind to both the unmodified and the modified protein, and the second specific binding member may be specific to the post-translationally modified protein.

In some embodiments, the analyte may be a cell, such as, circulating tumor cell, pathogenic bacteria, viruses (including retroviruses, herpesviruses, adenoviruses, lentiviruses, Filoviruses (e.g., West Nile, Ebola and Zika viruses), hepatitis viruses (e.g., A, B, C, D, and E); HPV, Parvovirus, etc.; spores, etc.

A non-limiting list of analytes that may be analyzed by the methods presented herein include Aβ42 amyloid beta-protein, fetuin-A, tau, secretogranin II, prion protein, Alpha-synuclein, tau protein, neurofilament light chain, parkin, PTEN induced putative kinase 1, DJ-1, leucine-rich repeat kinase 2, mutated ATP13A2, Apo H, ceruloplasmin, Peroxisome proliferator-activated receptor gamma coactivator-1 alpha (PGC-1α), transthyretin, Vitamin D-binding Protein, Active-B12, B12, cortisol, folate, frustosamine, homocysteine, intact PTH, pepsinogen I & II, DHEA-S, Estradiol, hCG, progesterone, prolactin, SHBG, testosterone, proapoptotic kinase R (PKR) and its phosphorylated PKR (pPKR), IL-12p40, CXCL13, IL-8, Dkk-3 (semen), p14 endocan fragment, Serum, ACE2, autoantibody to CD25, hTERT, CAI25 (MUC 16), VEGF, sIL-2, Osteopontin, Human epididymis protein 4 (HE4), Alpha-Fetoprotein, Albumin, albuminuria, microalbuminuria, neutrophil gelatinase-associated lipocalin (NGAL), Cystatin C, interleukin 18 (IL-18), Kidney Injury Molecule-1 (KIM-1), Liver Fatty Acid Binding Protein (L-FABP), LMP1, BARF1, IL-8, BRAF, CCNI, EGRF, FGF19, FRS2, GREB1, and LZTS1, alpha-amylase, carcinoembryonic antigen (CEA), CA 125, thioredoxin, beta-2 microglobulin levels—monitor activity of the virus, tumor necrosis factor-alpha receptors—monitor activity of the virus, Alpha-fetoprotein (AFP), CA15-3, CA 19-9, CYFRA 21-1, HE-4, PIVKA-11, ProGRP, SCC, follicle-stimulating hormone (FSH), leutinizing hormone (LH), T-cell lymphoma invasion and metastasis 1 (TIAM1), N-cadherin, EC39, amphiregulin, dUTPase, secretory gelsolin (pGSN), PSA (prostate specific antigen), thymosin β15, insulin, plasma C-peptide, glycosylated hemoglobin (HBA1c), C-Reactive Protein (CRP), Interleukin-6 (IL-6), ARHGDIB (Rho GDP-dissociation inhibitor 2), CFL1 (Cofilin-1), PFN1 (profilin-1), GSTP1 (Glutathione S-transferase P), S100A11 (Protein S100-A11), PRDX6 (Peroxiredoxin-6), HSPE1 (10 kDa heat shock protein, mitochondrial), LYZ (Lysozyme C precursor), GPI (Glucose-6-phosphate isomerase), HIST2H2AA (Histone H2A type 2-A), GAPDH (Glyceraldehyde-3-phosphate dehydrogenase), HSPG2 (Basement membrane-specific heparan sulfate proteoglycan core protein precursor), LGALS3BP (Galectin-3-binding protein precursor), CTSD (Cathepsin D precursor), APOE (Apolipoprotein E precursor), IQGAP1 (Ras GTPase-activating-like protein IQGAP1), CP (Ceruloplasmin precursor), and IGLC2 (IGLC1 protein), PCDGF/GP88, EGFR, HER2, MUC4, IGF-IR, p27(kip1), Akt, HER3, HER4, PTEN, PIK3CA, SHIP, Grb2, Gab2, PDK-1 (3-phosphoinositide dependent protein kinase-1), TSC1, TSC2, mTOR, MIG-6 (ERBB receptor feedback inhibitor 1), S6K, src, KRAS, MEK mitogen-activated protein kinase 1, cMYC, TOPO II topoisomerase (DNA) II alpha 170 kDa, FRAP1, NRG1, ESR1, ESR2, PGR, CDKN1B, MAP2K1, NEDD4-1, FOXO3A, PPP1R1B, PXN, ELA2, CTNNB1, AR, EPHB2, KLF6, ANXA7, NKX3-1, PITX2, MKI67, PHLPP, adiponectin (ADIPOQ), fibrinogen alpha chain (FGA), leptin (LEP), advanced glycosylation end product-specific receptor (AGER aka RAGE), alpha-2-HS-glycoprotein (AHSG), angiogenin (ANG), CD14 molecule (CD14), ferritin (FTH1), insulin-like growth factor binding protein 1 (IGFBP1), interleukin 2 receptor, alpha (IL2RA), vascular cell adhesion molecule 1 (VCAM1) and Von Willebrand factor (VWF), myeloperoxidase (MPO), IL1α, TNFα, perinuclear anti-neutrophil cytoplasmic antibody (p-ANCA), lactoferrin, calprotectin, Wilm's Tumor-1 protein, Aquaporin-1, MLL3, AMBP, VDAC1, *E. coli* enterotoxins (heat-labile exotoxin, heat-stable enterotoxin), influenza HA antigen, tetanus toxin, diphtheria toxin, botulinum toxins, Shiga toxin, Shiga-like toxin I, Shiga-like toxin II, *Clostridium difficile* toxins A and B, etc.

Exemplary targets of may be measured in a sample such as an environmental sample, a biological sample obtained from a patient or subject in need using the subject methods include: drugs of abuse (e.g. cocaine), protein biomarkers (including, but not limited to, Nucleolin, nuclear factor-kB essential modulator (NEMO), CD-30, protein tyrosine kinase 7 (PTK7), vascular endothelial growth factor (VEGF), MUC1 glycoform, immunoglobulin µ Heavy Chains (IGHM), Immunoglobulin E, αvβ3 integrin, α-thrombin, HIV gp120, NF-κB, E2F transcription factor, HER3, Plasminogen activator inhibitor, Tenascin C, CXCL12/SDF-1, prostate specific membrane antigen (PSMA), gastric cancer cells, HGC-27; cells (including, but not limited to, non-small cell lung cancer (NSCLC), colorectal cancer cells, (DLD-1), H23 lung adenocarcinoma cells, Ramos cells, T-cell acute lymphoblastic leukemia (T-ALL) cells, CCRF-CEM, acute myeloid leukemia (AML) cells (HL60), small-cell lung cancer (SCLC) cells, NCIH69, human glioblastoma cells, U118-MG, PC-3 cells, HER-2-overexpressing human breast cancer cells, SK-BR-3, pancreatic cancer cell line (Mia-PaCa-2), and infectious agents (including, but not limited to, *Mycobacterium tuberculosis, Staphylococcus aureus, Shigella dysenteriae, Escherichia coli* O157:H7, *Campylobacter jejuni, Listeria monocytogenes, Pseudomonas aeruginosa, Salmonella* O8, and *Salmonella enteritidis*).

Exemplary targets that may be measured in a sample obtained from a patient or subject in need using the subject methods include, but are not limited to: HBV core capsid protein, CDK2, E2F transcription factor, Thymidylate synthase, Ras, EB1, and Receptor for Advanced Glycated End products (RAGE).

6. SAMPLES

As used herein, "sample", "test sample", "biological sample" refer to fluid sample containing or suspected of containing an analyte of interest. The sample may be derived from any suitable source. In some cases, the sample may comprise a liquid, fluent particulate solid, or fluid suspension of solid particles. In some cases, the sample may be processed prior to the analysis described herein. For example, the sample may be separated or purified from its source prior to analysis; however, in certain embodiments, an unprocessed sample containing the analyte may be assayed directly. The source of the analyte molecule may be synthetic (e.g., produced in a laboratory), the environment (e.g., air, soil, fluid samples, e.g., water supplies, etc.), an animal, e.g., a mammal, a plant, or any combination thereof. In a particular example, the source of an analyte is a human bodily substance (e.g., bodily fluid, blood, serum, plasma, urine, saliva, sweat, sputum, semen, mucus, lacrimal fluid, lymph fluid, amniotic fluid, interstitial fluid, lung lavage, cerebrospinal fluid, feces, tissue, organ, or the like). Tissues may include, but are not limited to skeletal muscle tissue, liver tissue, lung tissue, kidney tissue, myocardial tissue, brain tissue, bone marrow, cervix tissue, skin, etc. The sample may be a liquid sample or a liquid extract of a solid sample. In certain cases, the source of the sample may be an organ or tissue, such as a biopsy sample, which may be solubilized by tissue disintegration/cell lysis.

A wide range of volumes of the fluid sample may be analyzed. In a few exemplary embodiments, the sample volume may be about 0.5 nL, about 1 nL, about 3 nL, about 0.01 µL, about 0.1 µL, about 1 µL, about 5 µL, about 10 µL, about 100 µL, about 1 mL, about 5 mL, about 10 mL, or the like. In some cases, the volume of the fluid sample is between about 0.01 µL and about 10 mL, between about 0.01 µL and about 1 mL, between about 0.01 µL and about 100 µL, or between about 0.1 µL and about 10 µL.

In some cases, the fluid sample may be diluted prior to use in an assay. For example, in embodiments where the source of an analyte molecule is a human body fluid (e.g., blood, serum), the fluid may be diluted with an appropriate solvent (e.g., a buffer such as PBS buffer). A fluid sample may be diluted about 1-fold, about 2-fold, about 3-fold, about 4-fold, about 5-fold, about 6-fold, about 10-fold, about 100-fold, or greater, prior to use.

In some cases, the sample may undergo pre-analytical processing. Pre-analytical processing may offer additional functionality such as nonspecific protein removal and/or effective yet cheaply implementable mixing functionality. General methods of pre-analytical processing may include the use of electrokinetic trapping, AC electrokinetics, surface acoustic waves, isotachophoresis, dielectrophoresis, electrophoresis, or other pre-concentration techniques known in the art. In some cases, the fluid sample may be concentrated prior to use in an assay. For example, in embodiments where the source of an analyte molecule is a human body fluid (e.g., blood, serum), the fluid may be concentrated by precipitation, evaporation, filtration, centrifugation, or a combination thereof. A fluid sample may be concentrated about 1-fold, about 2-fold, about 3-fold, about 4-fold, about 5-fold, about 6-fold, about 10-fold, about 100-fold, or greater, prior to use.

In certain embodiments, the analyte is not amplified (i.e., the copy number of the analyte is not increased) prior to the measurement of the analyte. For example, in cases where the analyte is DNA or RNA, the analyte is not replicated to increase copy numbers of the analyte. In certain cases, the analyte is a protein or a small molecule.

7. VARIATIONS ON METHODS

The disclosed methods of determining the presence or amount of analyte of interest present in a sample may be as described above. The methods may also be adapted in view of other methods for analyzing analytes. Examples of well-known variations include, but are not limited to, immunoassay, such as sandwich immunoassay (e.g., monoclonal-polyclonal sandwich immunoassays, including enzyme detection (enzyme immunoassay (EIA) or enzyme-linked immunosorbent assay (ELISA), competitive inhibition immunoassay (e.g., forward and reverse), enzyme multiplied immunoassay technique (EMIT), a competitive binding assay, bioluminescence resonance energy transfer (BRET), one-step antibody detection assay, homogeneous assay, heterogeneous assay, capture on the fly assay, etc. In some instances, the descriptions below may overlap the method described above; in others, the descriptions below may provide alternates.

a) Immunoassay

The analyte of interest, and/or peptides or fragments thereof, may be analyzed using an immunoassay. The presence or amount of analyte of interest can be determined using the herein-described antibodies and detecting specific binding to analyte of interest. Any immunoassay may be utilized. The immunoassay may be an enzyme-linked immunoassay (ELISA), a competitive inhibition assay, such as forward or reverse competitive inhibition assays, or a competitive binding assay, for example. In some embodiments, one signal generating compound or signal generating substrate is attached to the capture antibody and the detection antibody. Alternately, a microparticle employed for capture, also can function for detection.

A homogeneous format may be used. For example, after the test sample is obtained from a subject, a mixture is prepared. The mixture contains the test sample being assessed for analyte, a first specific binding partner, and a second specific binding partner. The order in which the test sample, the first specific binding partner, and the second specific binding partner are added to form the mixture is not critical. The test sample is simultaneously contacted with the first specific binding partner and the second specific binding partner. In some embodiments, the first specific binding partner and any analyte of interest contained in the test sample may form a first specific binding partner-analyte of interest-antigen complex and the second specific binding partner may form a first specific binding partner-analyte of interest-second specific binding partner complex. In some embodiments, the second specific binding partner and any analyte of interest contained in the test sample may form a second specific binding partner-analyte of interest-antigen complex and the first specific binding partner may form a first specific binding partner-analyte of interest-second specific binding partner complex. Moreover, the second specific binding partner is labeled with or contains a detectable label as described herein.

A heterogeneous format may be used. For example, after the test sample is obtained from a subject, a first mixture is prepared. The mixture contains the test sample being assessed for analyte of interest and a first specific binding partner, wherein the first specific binding partner and any analyte of interest contained in the test sample form a first specific binding partner-analyte of interest complex. Preferably, the first specific binding partner is an anti-analyte of interest antibody or a fragment thereof. The order in which the test sample and the first specific binding partner are added to form the mixture is not critical. Preferably, the first specific binding partner is immobilized on a solid phase. The solid phase used in the immunoassay (for the first specific binding partner and, optionally, the second specific binding partner) can be any solid phase known in the art, such as, but not limited to, a magnetic particle, a bead a nanobead, a microbead, a nanoparticle, a microparticle, a membrane, a scaffolding molecule, a film, a filter paper, a disc, or a chip (e.g., a microfluidic chip). In those embodiments where the solid phase is a bead, the bead may be a magnetic bead or a magnetic particle. Magnetic beads/particles may be ferromagnetic, ferrimagnetic, paramagnetic, superparamagnetic or ferrofluidic. Exemplary ferromagnetic materials include Fe, Co, Ni, Gd, Dy, $CrO_2$, MnAs, MnBi, EuO, and NiO/Fe. Examples of ferrimagnetic materials include $NiFe_2O_4$, $CoFe_2O_4$, $Fe_3O_4$ (or $FeO \cdot Fe_2O_3$). Beads can have a solid core portion that is magnetic and is surrounded by one or more non-magnetic layers. Alternately, the magnetic portion can be a layer around a non-magnetic core. The solid support on which the first specific binding member is immobilized may be stored in dry form or in a liquid. The magnetic beads may be subjected to a magnetic field prior to or after contacting with the sample with a magnetic bead on which the first specific binding member is immobilized.

After the mixture containing the first specific binding partner-analyte of interest complex is formed, any unbound analyte of interest is removed from the complex using any technique known in the art. For example, the unbound analyte of interest can be removed by washing. Desirably, however, the first specific binding partner is present in excess of any analyte of interest present in the test sample, such that all analyte of interest that is present in the test sample is bound by the first specific binding partner.

After any unbound analyte of interest is removed, a second specific binding partner is added to the mixture to form a first specific binding partner-analyte of interest-second specific binding partner complex. The second specific binding partner is preferably an anti-analyte of interest antibody that binds to an epitope on analyte of interest that differs from the epitope on analyte of interest bound by the first specific binding partner. Moreover, also preferably, the second specific binding partner is labeled with or contains a signal generating compound or signal generating substrate, as described above.

The use of immobilized antibodies or fragments thereof may be incorporated into the immunoassay. The antibodies may be immobilized onto a variety of supports, such as magnetic or chromatographic matrix particles, latex particles or modified surface latex particles, polymer or polymer film, plastic or plastic film, planar substrate, a microfluidic surface, pieces of a solid substrate material, and the like.

b) Sandwich Immunoassay

The sandwich immunoassay measures the amount of antigen between two layers of antibodies (i.e., a capture antibody (i.e., at least one capture antibody) and a detection antibody (i.e. at least one detection antibody). The capture antibody and the detection antibody bind to different epitopes on the antigen, e.g., analyte of interest. Desirably, binding of the capture antibody to an epitope does not interfere with binding of the detection antibody to an epitope. Either monoclonal or polyclonal antibodies may be used as the capture and detection antibodies in the sandwich immunoassay.

Generally, at least two antibodies are employed to separate and quantify analyte of interest in a test sample. More specifically, the at least two antibodies bind to certain epitopes of analyte of interest or an analyte of interest fragment forming an immune complex which is referred to as a "sandwich". One or more antibodies can be used to capture the analyte of interest in the test sample (these antibodies are frequently referred to as a "capture" antibody or "capture" antibodies), and one or more antibodies with a signal generating compound or signal generating substrate that also bind the analyte of interest (these antibodies are frequently referred to as the "detection" antibody or "detection" antibodies) can be used to complete the sandwich. In a sandwich assay, the binding of an antibody to its epitope desirably is not diminished by the binding of any other antibody in the assay to its respective epitope. In other words, antibodies are selected so that the one or more first antibodies brought into contact with a test sample suspected of containing analyte of interest do not bind to all or part of an epitope recognized by the second or subsequent antibodies, thereby interfering with the ability of the one or more second detection antibodies to bind to the analyte of interest. The capture antibody described above is an example of a capture molecule. The detection antibody described above is an example of a detection molecule.

In a preferred embodiment, a test sample suspected of containing analyte of interest can be contacted with at least one capture antibody (or antibodies) and at least one detection antibodies either simultaneously or sequentially. In the sandwich assay format, a test sample suspected of containing analyte of interest (membrane-associated analyte of interest, soluble analyte of interest, fragments of membrane-associated analyte of interest, fragments of soluble analyte of interest, variants of analyte of interest (membrane-associated or soluble analyte of interest) or any combinations thereof) is first brought into contact with the at least one capture antibody that specifically binds to a particular epitope under conditions which allow the formation of an antibody-analyte of interest complex. If more than one capture antibody is used, a multiple capture antibody-analyte of interest complex is formed. In a sandwich assay, the antibodies, preferably, the at least one capture antibody, are used in molar excess amounts of the maximum amount of analyte of interest or the analyte of interest fragment expected in the test sample.

Optionally, prior to contacting the test sample with the at least one first capture antibody, the at least one capture antibody can be bound to a solid support which facilitates the separation the antibody-analyte of interest complex from the test sample. Any solid support known in the art can be used, including but not limited to, solid supports made out of polymeric materials in the form of planar substrates or beads, and the like. The antibody (or antibodies) can be bound to the solid support by adsorption, by covalent bonding using a chemical coupling agent or by other means known in the art, provided that such binding does not interfere with the ability of the antibody to bind analyte of interest or analyte of interest fragment. Moreover, if necessary, the solid support can be derivatized to allow reactivity with various functional groups on the antibody. Such derivatization requires the use of certain coupling agents such as, but not limited to, maleic anhydride, N-hydroxysuccinimide, azido, alkynyl, and 1-ethyl-3-(3-dimethylaminopropyl)carbodiimide.

After the test sample suspected of containing analyte of interest is brought into contact with the at least one capture antibody, the test sample is incubated in order to allow for the formation of a capture antibody (or capture antibodies)-analyte of interest complex. The incubation can be carried out at a pH of from about 4.5 to about 10.0, at a temperature of from about 2° C. to about 45° C., and for a period from at least about one (1) minute to about eighteen (18) hours, from about 2-6 minutes, or from about 3-4 minutes.

After formation of the capture antibody (antibodies)-analyte of interest complex, the complex is then contacted with at least one detection antibody (under conditions which allow for the formation of a capture antibody (antibodies)-analyte of interest-detection antibody (antibodies) complex). If the capture antibody-analyte of interest complex is contacted with more than one detection antibody, then a capture antibody (antibodies)-analyte of interest-detection antibody (antibodies) detection complex is formed. As with the capture antibody, when the at least one detection (and subsequent) antibody is brought into contact with the capture antibody-analyte of interest complex, a period of incubation under conditions similar to those described above is required for the formation of the capture antibody (antibodies)-analyte of interest-detection antibody (antibodies) complex. Preferably, at least one detection antibody contains a signal generating compound or signal generating substrate. The signal generating compound or signal generating substrate can be bound to the at least one detection antibody prior to, simultaneously with or after the formation of the capture antibody (antibodies)-analyte of interest-detection antibody (antibodies) complex.

The order in which the test sample and the specific binding partner(s) are added to form the mixture for assay is not critical. If the first specific binding partner is attached to the signal generating compound or signal generating substrate, then signal generating compound or signal generating substrate-attached first specific binding partner-analyte of interest complexes form. Alternatively, if a second specific binding partner is used and the second specific binding partner is attached to the signal generating compound or signal generating substrate, then signal generating compound or signal generating substrate-attached complexes of first specific binding partner-analyte of interest-second specific binding partner form. Any unbound specific binding partner, whether labeled or unlabeled, can be removed from the mixture using any technique known in the art, such as washing.

Next, signal, indicative of the presence of analyte of interest or a fragment thereof is generated. Based on the parameters of the signal generated, the amount of analyte of interest in the sample can be quantified. Optionally, a standard curve can be generated using serial dilutions or solutions of known concentrations of analyte of interest by mass spectroscopy, gravimetric methods, and other techniques known in the art.

c) Forward Competitive Inhibition

In a forward competitive format, an aliquot of labeled analyte of interest of a known concentration is used to compete with analyte of interest in a test sample for binding to analyte of interest antibody.

In a forward competition assay, an immobilized specific binding partner (such as an antibody) can either be sequentially or simultaneously contacted with the test sample and a labeled analyte of interest, analyte of interest fragment or analyte of interest variant thereof. The analyte of interest peptide, analyte of interest fragment or analyte of interest variant can be attached with a signal generating compound or signal generating substrate. In this assay, the antibody can be immobilized on to a solid support. Alternatively, the antibody can be coupled to an antibody, such as an antispecies antibody, that has been immobilized on a solid support, such as a microparticle or planar substrate.

The labeled analyte of interest, the test sample and the antibody are incubated under conditions similar to those described above in connection with the sandwich assay format. Two different species of antibody-analyte of interest complexes may then be generated. Specifically, one of the antibody-analyte of interest complexes generated contains a signal generating compound or signal generating substrate while the other antibody-analyte of interest complex does not contain a signal generating compound or signal generating substrate. The antibody-analyte of interest complex can be, but does not have to be, separated from the remainder of the test sample prior to quantification of the detectable product or detectable label. Regardless of whether the antibody-analyte of interest complex is separated from the remainder of the test sample, the amount of detectable product or detectable label (e.g., detectable signal) in the antibody-analyte of interest complex is then quantified. The concentration of analyte of interest (such as membrane-associated analyte of interest, soluble analyte of interest, fragments of soluble analyte of interest, variants of analyte of interest (membrane-associated or soluble analyte of interest) or any combinations thereof) in the test sample can then be determined, e.g., as described above. If helpful, determination can be done by comparing the quantity of detectable product or detectable label (e.g., detectable signal) in the antibody-analyte of interest complex to a standard curve. The standard curve can be generated using serial dilutions of analyte of interest (such as membrane-associated analyte of interest, soluble analyte of interest, fragments of soluble analyte of interest, variants of analyte of interest (membrane-associated or soluble analyte of interest) or any combinations thereof) of known concentration, where concentration is determined by mass spectroscopy, gravimetrically and by other techniques known in the art.

Optionally, the antibody-analyte of interest complex can be separated from the test sample by binding the antibody to a solid support, such as the solid supports discussed above in connection with the sandwich assay format, and then removing the remainder of the test sample from contact with the solid support.

d) Reverse Competition Assay

In a reverse competition assay, an immobilized analyte of interest can either be sequentially or simultaneously contacted with a test sample and at least one labeled antibody. The analyte of interest can be bound to a solid support, such as the solid supports discussed above in connection with the sandwich assay format.

The immobilized analyte of interest, test sample and at least one labeled antibody are incubated under conditions similar to those described above in connection with the sandwich assay format. Two different species analyte of interest-antibody complexes are then generated. Specifically, one of the analyte of interest-antibody complexes generated is immobilized and contains a signal generating compound or signal generating substrate while the other analyte of interest-antibody complex is not immobilized and contains signal generating compound or signal generating substrate. The non-immobilized analyte of interest-antibody complex and the remainder of the test sample are removed from the presence of the immobilized analyte of interest-antibody complex through techniques known in the art, such as washing. Once the non-immobilized analyte of interest antibody complex is removed, the amount of signal generating compound or signal generating substrate in the immobilized analyte of interest-antibody complex is then quantified. The concentration of analyte of interest in the test sample can then be determined by comparing the quantity of detectable signal as described above. If helpful, this can be done with use of a standard curve. The standard curve can be generated using serial dilutions of analyte of interest or analyte of interest fragment of known concentration, where concentration is determined by mass spectroscopy, gravimetrically and by other techniques known in the art.

e) One-Step Immunoassay or Capture on the Fly Assay

In a one-step immunoassay or capture on the fly assay, a solid substrate is pre-coated with an immobilization agent. The capture agent, the analyte and the detection agent are added to the solid substrate together, followed by a wash step prior to detection. The capture agent can bind the analyte and comprises a ligand for an immobilization agent. The capture agent and the detection agents may be antibodies or any other moiety capable of capture or detection as described herein or known in the art. The ligand may comprise a peptide tag and an immobilization agent may comprise an anti-peptide tag antibody. Alternately, the ligand and the immobilization agent may be any pair of agents capable of binding together so as to be employed for a capture on the fly assay (e.g., specific binding pair, and others such as are known in the art). More than one analyte may be measured. In some embodiments, the solid substrate may be coated with an antigen and the analyte to be analyzed is an antibody.

In some embodiments, a solid support (such as a microparticle) pre-coated with an immobilization agent (such as biotin, streptavidin, etc.) and at least a first specific binding member and a second specific binding member (which function as capture and detection reagents, respectively) are used. The first specific binding member comprises a ligand for the immobilization agent (for example, if the immobilization agent on the solid support is streptavidin, the ligand on the first specific binding member may be biotin) and also binds to the analyte of interest. The second specific binding member comprises a signal generating compound or signal generating substrate and binds to an analyte of interest. The solid support and the first and second specific binding members may be added to a test sample (either sequentially or simultaneously). The ligand on the first specific binding member binds to the immobilization agent on the solid support to form a solid support/first specific binding member complex. Any analyte of interest present in the sample binds to the solid support/first specific binding member complex to form a solid support/first specific binding member/analyte complex. The second specific binding member binds to the solid support/first specific binding member/analyte complex and the signal generating compounds or signal generating substrates detected. An optional wash step may be employed before the detection. In certain embodiments, in a one-step assay more than one analyte may be measured. In certain other embodiments, more than two specific binding members can be employed. In certain other embodiments, multiple signal generating compounds or signal generating substrates can be added. In certain other embodiments, multiple analytes of interest can be detected.

The use of a one step immunoassay or capture on the fly assay can be done in a variety of formats as described herein, and known in the art. For example the format can be a sandwich assay such as described above, but alternately can be a competition assay, can employ a single specific binding member, or use other variations such as are known.

f) Combination Assays (Co-Coating of Microparticles with Ag/Ab)

In a combination assay, a solid substrate, such as a microparticle is co-coated with an antigen and an antibody to capture an antibody and an antigen from a sample, respectively. The solid support may be co-coated with two or more different antigens to capture two or more different antibodies from a sample. The solid support may be co-coated with two or more different antibodies to capture two or more different antigens from a sample.

Additionally, the methods described herein may use blocking agents to prevent either specific or non-specific binding reactions (e.g., HAMA concern) among assay compounds. Once the agent (and optionally, any controls) is immobilized on the support, the remaining binding sites of the agent may be blocked on the support. Any suitable blocking reagent known to those of ordinary skill in the art may be used. For example, bovine serum albumin ("BSA"), phosphate buffered saline ("PBS") solutions of casein in PBS, Tween 20™ (Sigma Chemical Company, St. Louis, Mo.), or other suitable surfactant, as well as other blocking reagents, may be employed.

As is apparent from the present disclosure, the methods disclosed herein, including variations, may be used for diagnosing a disease, disorder or condition in a subject suspected of having the disease, disorder, or condition. For example, the sample analysis may be useful for detecting a disease marker, such as, a cancer marker, a marker for a cardiac condition, a toxin, a pathogen, such as, a virus, a bacteria, or a portion thereof. The methods also may be used for measuring analyte present in a biological sample. The methods also may be used in blood screening assays to detect a target analyte. The blood screening assays may be used to screen a blood supply.

8. MULTIPLEXING

The methods may include one or more (or alternately two or more) specific binding members to detect one or more (or alternately two or more) target analytes in the sample in a multiplexing assay. Each of the one or more (or alternately two or more) specific binding members binds to a different target analyte and each specific binding member is conjugated to a different signal generating compound or signal generated substrate. For example, a first specific binding member binds to a first target analyte, a second specific binding member binds to a second target analyte, a third specific binding member binds to a third target analyte, etc. and the first specific binding member is labeled with a first signal generating compound or first signal generating substrate, the second specific binding member is labeled with a second signal generating compound or second signal generating substrate, the third specific binding member is labeled with a third signal generating compound or a third signal generating substrate, etc. In some embodiments, the conditions of the sample can be changed at various times during the assay, allowing detection of the first signal generating compound or first signal generating substrate, the second signal generating compound or second signal generating substrate, the third signal generating compound or third signal generating substrate, etc., thereby detecting one or more (or alternately two or more) target analytes. In some embodiments, the one or more (or alternately two or more) signal generating compounds or signal generating substrates are detected simultaneously. In some embodiments, the one or more (or alternately two or more) signal generating compounds or signal generating substrates are detected consecutively. In some embodiments, the one or more (or alternately two or more) signal generating compounds or signal generating substrates generates a different detectable signal, such as a different wavelength of fluorescence signal.

Alternatively, each of the one or more (or alternately two or more) specific binding members binds to a different target analyte and each specific binding member is conjugated to a different solid support, such as a different fluorophore bead. For example, a first specific binding member binds to a first target analyte, a second specific binding member binds to a second target analyte, a third specific binding member binds to a third target analyte, etc., the first specific binding member is labeled with a first signal generating compound or first signal generating substrate, the second specific binding member is labeled with a second signal generating compound or second signal generating substrate, the third specific binding member is labeled with a third signal generating compound or a third signal generating substrate, etc., and the first specific binding member is immobilized on a first solid support, the second specific binding member is immobilized on a second solid support, the third specific binding member is immobilized on a third solid support, etc. In some embodiments, the one or more (or alternately two or more) signal generating compounds or signal generating substrates generates a different detectable signal, such as a different wavelength or fluorescence signal, and the different solid supports is detected simultaneously or consecutively.

In some embodiments, a first specific binding member binds to a first target analyte, a second specific binding member binds to a second target analyte, a third specific binding member binds to a third target analyte, etc., the first specific binding member, the second specific binding member, the third specific binding member, etc. are labeled with a signal generating compound or a signal generating substrate, and the first specific binding member is immobilized on a first solid support, the second specific binding member is immobilized on a second solid support, the third specific binding member is immobilized on a third solid support, etc. In some embodiments, the signal generating compounds or signal generating substrates generates a detectable signal, such as a different wavelength or fluorescence signal, and the different solid supports is detected simultaneously or consecutively.

9. KITS

Also provided herein is a kit for use in performing the above-described methods. The kit may include instructions for analyzing the analyte with the disclosed methods. Instructions included in the kit may be affixed to packaging material or may be included as a package insert. The instructions may be written or printed materials, but are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, "instructions" may include the address of an internet site that provides the instructions.

Alternatively or additionally, the kit may comprise a calibrator or control, e.g., purified, and optionally lyophilized analyte of interest or in liquid, gel or other forms, and/or at least one container (e.g., tube, microtiter plates or strips) for use with the methods described above, and/or a buffer, such as an assay buffer or a wash buffer, either one of which can be provided as a concentrated solution. In some embodiments, the kit comprises all components, i.e., reagents, standards, buffers, diluents, etc., which are necessary to perform the assay. The instructions also can include instructions for generating a standard curve.

The kit may further comprise reference standards for quantifying the analyte of interest. The reference standards may be employed to establish standard curves for interpolation and/or extrapolation of the analyte of interest concentrations. The kit may include reference standards that vary in terms of concentration level. For example, the kit may include one or more reference standards with either a high concentration level, a medium concentration level, or a low concentration level. In terms of ranges of concentrations for the reference standard, this can be optimized per the assay. Exemplary concentration ranges for the reference standards include but are not limited to, for example: about 10 fg/mL, about 20 fg/mL, about 50 fg/mL, about 75 fg/mL, about 100 fg/mL, about 150 fg/mL, about 200 fg/mL, about 250 fg/mL, about 500 fg/mL, about 750 fg/mL, about 1000 fg/mL, about 10 pg/mL, about 20 pg/mL, about 50 pg/mL, about 75 pg/mL, about 100 pg/mL, about 150 pg/mL, about 200 pg/mL, about 250 pg/mL, about 500 pg/mL, about 750 pg/mL, about 1 ng/mL, about 5 ng/mL, about 10 ng/mL, about 12.5 ng/mL, about 15 ng/mL, about 20 ng/mL, about 25 ng/mL, about 40 ng/mL, about 45 ng/mL, about 50 ng/mL, about 55 ng/mL, about 60 ng/mL, about 75 ng/mL, about 80 ng/mL, about 85 ng/mL, about 90 ng/mL, about 95 ng/mL, about 100 ng/mL, about 125 ng/mL, about 150 ng/mL, about 165 ng/mL, about 175 ng/mL, about 200 ng/mL, about 225 ng/mL, about 250 ng/mL, about 275 ng/mL, about 300 ng/mL, about 400 ng/mL, about 425 ng/mL, about 450 ng/mL, about 465 ng/mL, about 475 ng/mL, about 500 ng/mL, about 525 ng/mL, about 550 ng/mL, about 575 ng/mL, about 600 ng/mL, about 700 ng/mL, about 725 ng/mL, about 750 ng/mL, about 765 ng/mL, about 775 ng/mL, about 800 ng/mL, about 825 ng/mL, about 850 ng/mL, about 875 ng/mL, about 900 ng/mL, about 925 ng/mL, about 950 ng/mL, about 975 ng/mL, about 1000 ng/mL, about 2 µg/mL, about 3 µg/mL, about 4 µg/mL, about 5 µg/mL, about 6 µg/mL, about 7 µg/mL, about 8 µg/mL, about 9 µg/mL, about 10 µg/mL, about 20 µg/mL, about 30 µg/mL, about 40 µg/mL, about 50 µg/mL, about 60 µg/mL, about 70 µg/mL, about 80 µg/mL, about 90 µg/mL, about 100 µg/mL, about 200 µg/mL, about 300 µg/mL, about 400 µg/mL, about 500 µg/mL, about 600 µg/mL, about 700 µg/mL, about 800 µg/mL, about 900 µg/mL, about 1000 µg/mL, about 2000 µg/mL, about 3000 µg/mL, about 4000 µg/mL, about 5000 µg/mL, about 6000 µg/mL, about 7000 µg/mL, about 8000 µg/mL, about 9000 µg/mL, or about 10000 µg/mL.

Any specific binding members, which are provided in the kit may incorporate an at least one signal generating compound, one or more signal generating substrates, or the like, or the kit can include reagents for labeling the specific binding members or reagents for detecting the specific binding members and/or for labeling the analytes or reagents for detecting the analyte. If desired, the kit can contain one or more different signal generating compounds and/or signal generating or substrates. The specific binding members, calibrators, and/or controls can be provided in separate containers or pre-dispensed into an appropriate assay format.

The kit may include one or more specific binding members, for example, to detect one or more target analytes in the sample in a multiplexing assay. The number of different types of specific binding members in the kit may range widely depending on the intended use of the kit. The number of specific binding members in the kit may range from 1 to about 10, or higher. For example, the kit may include 1 to 10 specific binding members, 1 to 9 specific binding members, 1 to 8 specific binding members, 1 to 7 specific binding members, 1 to 6 specific binding members, 1 to 5 specific binding members, 1 to 4 specific binding members, 1 to 3 specific binding members, 1 to 2 specific binding members, 2 to 10 specific binding members, 2 to 9 specific binding members, 2 to 8 specific binding members, 2 to 7 specific binding members, 2 to 6 specific binding members, 2 to 5 specific binding members, 2 to 4 specific binding members, 3 to 10 specific binding members, 3 to 9 specific binding members, 3 to 8 specific binding members, 3 to 7 specific binding members, 3 to 6 specific binding members, 3 to 5 specific binding members, 3 to 4 specific binding members, 4 to 10 specific binding members, 4 to 9 specific binding members, 4 to 8 specific binding members, 4 to 7 specific binding members, 4 to 6 specific binding members, 5 to 10 specific binding members, 5 to 9 specific binding members, 5 to 8 specific binding members, 5 to 7 specific binding members, 5 to 6 specific binding members, 6 to 10 specific binding members, 6 to 9 specific binding members, 6 to 8 specific binding members, 6 to 7 specific binding members, 7 to 10 specific binding members, 7 to 9 specific binding members, 7 to 8 specific binding members, 8 to 10 specific binding members, 8 to 9 specific binding members, or 9 to 10 specific binding members. Each of the one or more specific binding members may bind to a different target analyte and each specific binding member may be associated with a different signal generating compound and/or signal generating substrate. For example, the kit may include a first specific binding member that binds to a first target analyte, a second specific binding member that binds to a second target analyte, a third specific binding member that binds to a third target analyte, etc. and the first specific binding member is associated with a first signal generating compound and/or first signal generating substrate, the second specific binding member is associated with a second signal generating compound and/or second signal generating substrate, the third specific binding member is associated with a third signal generating compound and/or third signal generating substrate, etc. In addition to the one or more specific binding members, the kits may further comprise one or more additional assay components, such as suitable buffer media, and the like. The kits may also include a device for detecting and measuring the signal generating compound and/or signal generating substrate, such as those described supra. Finally, the kits may comprise instructions for using the specific binding members in methods of analyte detection according to the subject invention, where these instructions for use may be present on the kit packaging and/or on a package insert.

Optionally, the kit includes quality control components (for example, sensitivity panels, calibrators, and positive controls). Preparation of quality control reagents is well-known in the art and is described on insert sheets for a variety of immunodiagnostic products. Sensitivity panel members optionally are used to establish assay performance characteristics, and further optionally are useful indicators of the integrity of the kit reagents, and the standardization of assays.

The kit can also optionally include other reagents required to conduct a diagnostic assay or facilitate quality control evaluations, such as buffers, salts, enzymes, enzyme co-factors, substrates, detection reagents, and the like. Other components, such as buffers and solutions for the isolation and/or treatment of a test sample (e.g., pretreatment reagents), also can be included in the kit. The kit can additionally include one or more other controls. One or more of the components of the kit can be lyophilized, in which case the kit can further comprise reagents suitable for the reconstitution of the lyophilized components. One or more of the components may be in liquid form.

The various components of the kit optionally are provided in suitable containers as necessary. The kit further can include containers for holding or storing a sample (e.g., a container for a urine, saliva, plasma, cerebrospinal fluid, or serum sample, or appropriate container for storing, transporting or processing tissue so as to create a tissue aspirate). Where appropriate, the kit optionally also can contain reaction vessels, mixing vessels, and other components that facilitate the preparation of reagents or the test sample. The kit can also include one or more sample collection/acquisition instruments for assisting with obtaining a test sample, such as various blood collection/transfer devices such as microsampling devices, micro-needles, or other minimally invasive pain-free blood collection methods; blood collection tube(s); lancets; capillary blood collection tubes; other single fingertip-prick blood collection methods; buccal swabs, nasal/throat swabs; 16-gauge or other size needle, circular blade for punch biopsy (e.g., 1-8 mm, or other appropriate size), surgical knife or laser (e.g., particularly hand-held), syringes, sterile container, or cannula, for obtaining, storing or aspirating tissue samples; or the like. The kit can include one or more instruments for assisting with joint aspiration, cone biopsies, punch biopsies, fine-needle aspiration biopsies, image-guided percutaneous needle aspiration biopsy, bronchoaveolar lavage, endoscopic biopsies, and laparoscopic biopsies.

If desired, the kit can contain a solid phase, such as a magnetic particle, bead, membrane, scaffolding molecule, film, filter paper, disc, or chip.

If desired, the kit can further comprise one or more components, alone or in further combination with instructions, for assaying the test sample for another analyte, which can be a biomarker, such as a biomarker of a disease state or disorder, such as infectious disease, cardiac disease, metabolic disease, thyroid disease, etc.

The present invention has multiple aspects, illustrated by the following non-limiting examples.

10. EXAMPLES

Example 1

"Black Ink Addition" Method

Figure 3:
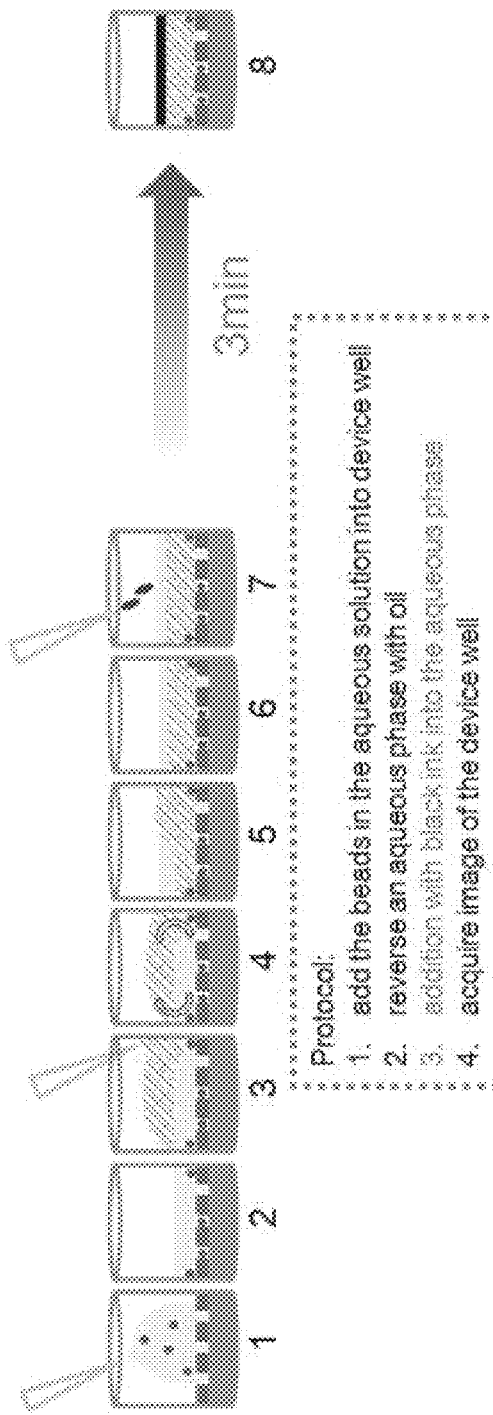
FIG. 3 shows an improved procedure of a fluorescent digital ELISA assay using "Black Ink Addition" to the displaced aqueous phase.

The "Black Ink Addition" method, shown in FIG. 3, involves the addition of black ink, such as India Ink, into the aqueous phase (the upper liquid phase including the fluorescent substrate) after the displacement of the aqueous phase by the sealant (e.g., oil) (see step 7 of FIG. 3). The substrate for the assay was fluorescein-di-phosphate (FDP). The buffer for the enzymatic reaction was 1M diethanolamine (DEA), 1 mM $MgCl_2$, 0.05% Tween20, and 300 µM FDP, pH 9.25. The digital ELISA using the "Black Ink Addition" method, in which black ink was added to the aqueous phase and the aqueous phase was not removed (C; see FIG. 3), was compared with digital ELISA that did not remove the aqueous phase (A) and digital ELISA that removed the aqueous phase (B). The number of target molecules was determined by counting the number of fluorescent droplets under an optical microscope using a fluorescein filter. At the same time, the total number of beads was counted using a tetramethylrhodamine (TRITC) filter. The digital ELISA with the "Black Ink Addition" method showed an improvement for counting the number of fluorescent droplets and increased number of analyzable images (FIGS. 4 and 5 and Table 1).

TABLE 1

| | | Aqueous Phase | Analyzable Image (# of pieces/45 pieces) |
|---|---|---|---|
| A | remained | with fluorescein | 0 |
| B | removed | sometime some remaining with fluorescein | 29 |
| C | remained | with fluorescein and black ink | 44 |

Figures 4A, 4B, 4C:
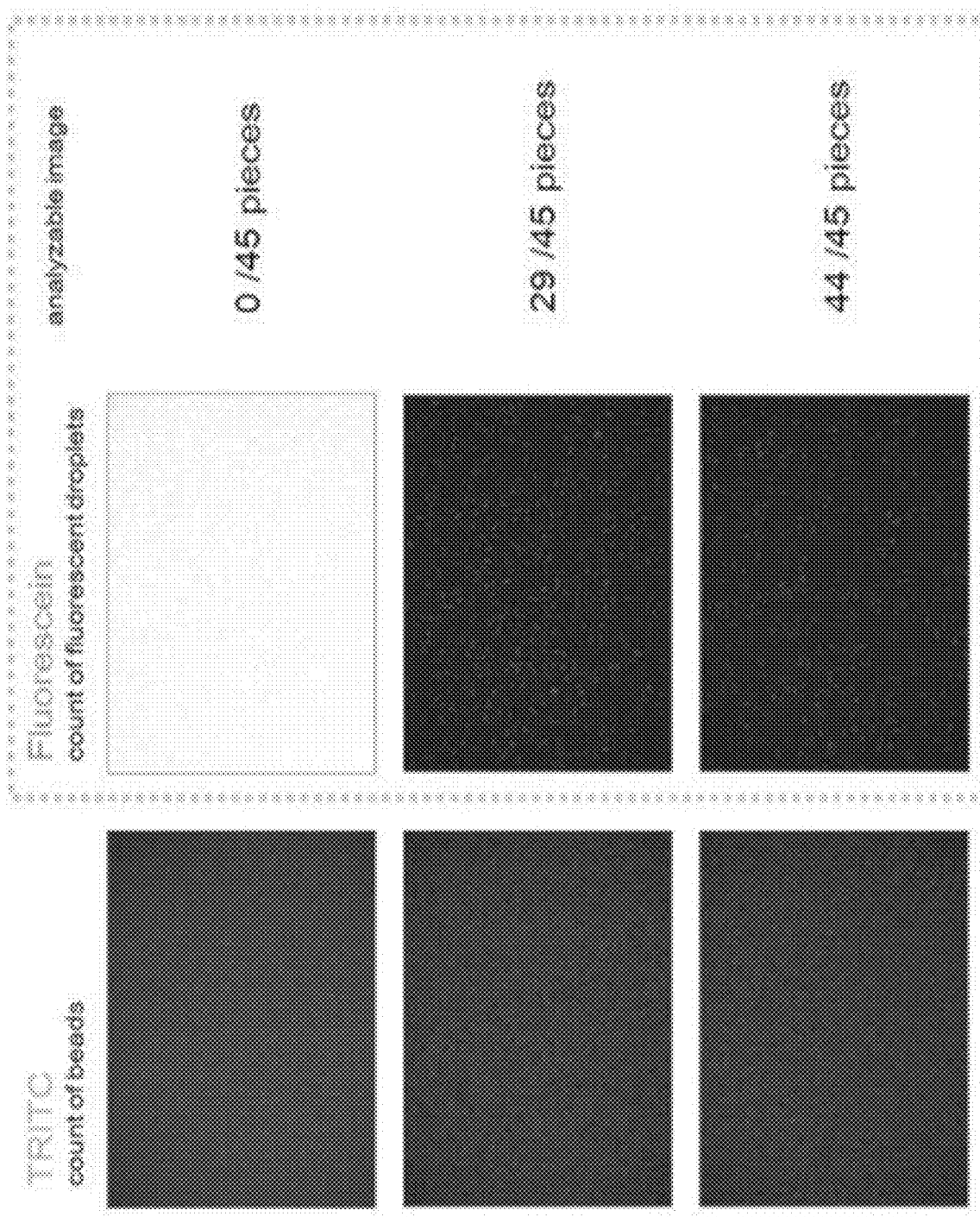
FIG. 4 shows image analysis data of treatments A (digital ELISA that did not remove the aqueous phase) (FIG. 4A), B (digital ELISA that removed the aqueous phase) (FIG. 4B), and C (black ink added to the aqueous phase and the aqueous phase was not removed) (FIG. 4C), using a tetramethylrhodamine (TRITC) filter for counting the number of beads and a fluorescein filter for counting the number of fluorescent droplets.
Figure 5:
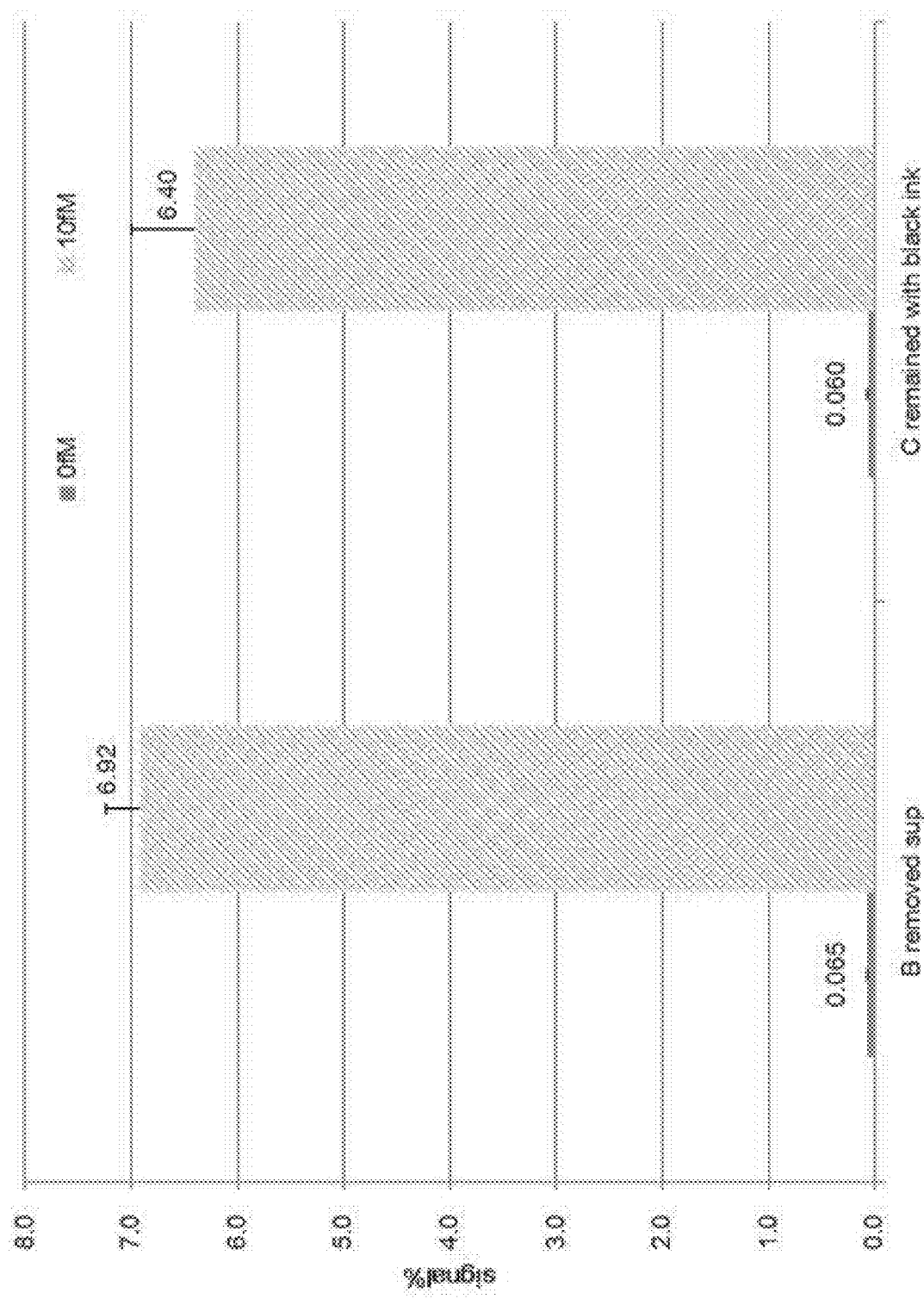
FIG. 5 shows the signal % (true signal) for treatments (B) and (C) as described in Example 1.

As shown in FIG. 4, both the TRITC and fluorescein filtered images were clear even if black ink was added. Fluorescent substance present in the upper aqueous phase obstructed the counting of the number of fluorescent droplets under an optical microscope. There was no fluorescein data for "A" (FIG. 4 and Table 3), in which the aqueous phase was not removed, due to the strong brightness of the fluorescent substance present in the upper aqueous phase. Only 29 pieces of analyzable images were obtained for "B" in which the upper aqueous solution was removed manually (FIG. 4 and Table 3), due to the fluorescent substance present in incomplete removal of the upper aqueous phase which resulted in some upper aqueous phase remaining in the well that obstructed the counting of the number of fluorescent droplets in 16 pieces of data. In contrast, 44 out of 45 images were acquired using the "Black Ink Addition" method without the removal of the aqueous phase.

Figure 6:
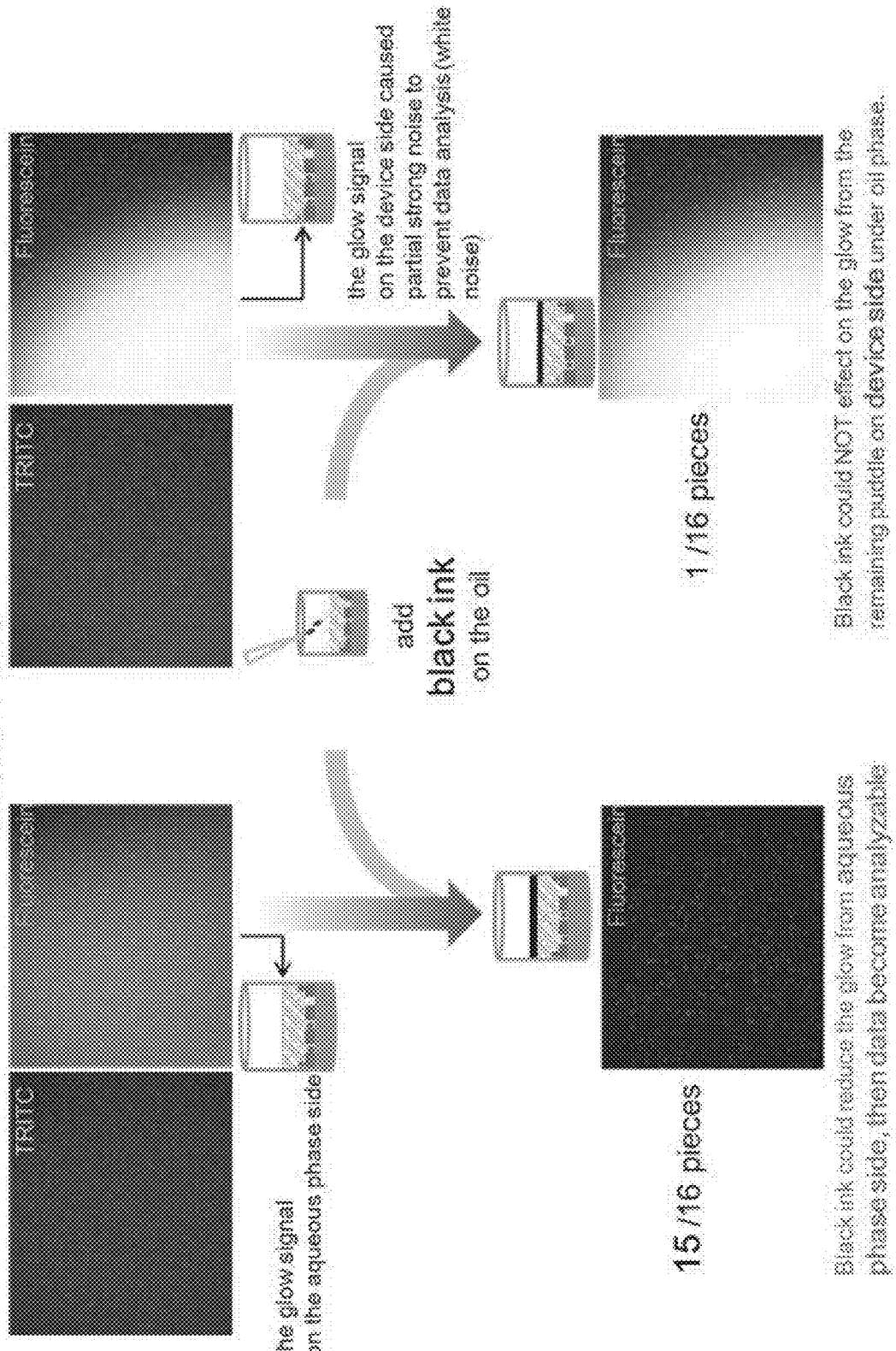
FIG. 6 shows 2 representative patterns of glowed images in fluorescein detection (16 unanalyzable pieces of treatment (B)).

There were 2 patterns of the glowed image in the acquired image for the 16 pieces of data that were unanalyzable for "B" (FIG. 6—top left and top right images). One pattern (15 out of 16 pieces) showed a high background image with the fluorescein filter due to glowing widely (top left images), and the other pattern (1 out of 16 pieces) showed an the image that strongly glowed around an edge (top right images). In the bottom images of FIG. 6, black ink was added into the sealant (e.g., oil) of the device well containing the fluorescent reaction. In the bottom left image, the high background due to the incomplete removal of the upper aqueous phase disappeared by adding the black ink as the 15 pieces that had high background image with the fluorescein filter showed clearer images, indicating that adding black ink can reduce background fluorescence even if the manual removal of the upper aqueous solution is incomplete. On the other hand, the right image pattern seen in the one piece that had an image that strongly glowed around an edge could not be analyzed even if black ink was added, as this glow signal came from residual aqueous phase on the device side (bottom side of the device well).

Example 2

"Black Ink Pre-Mix" Method

Figure 8:
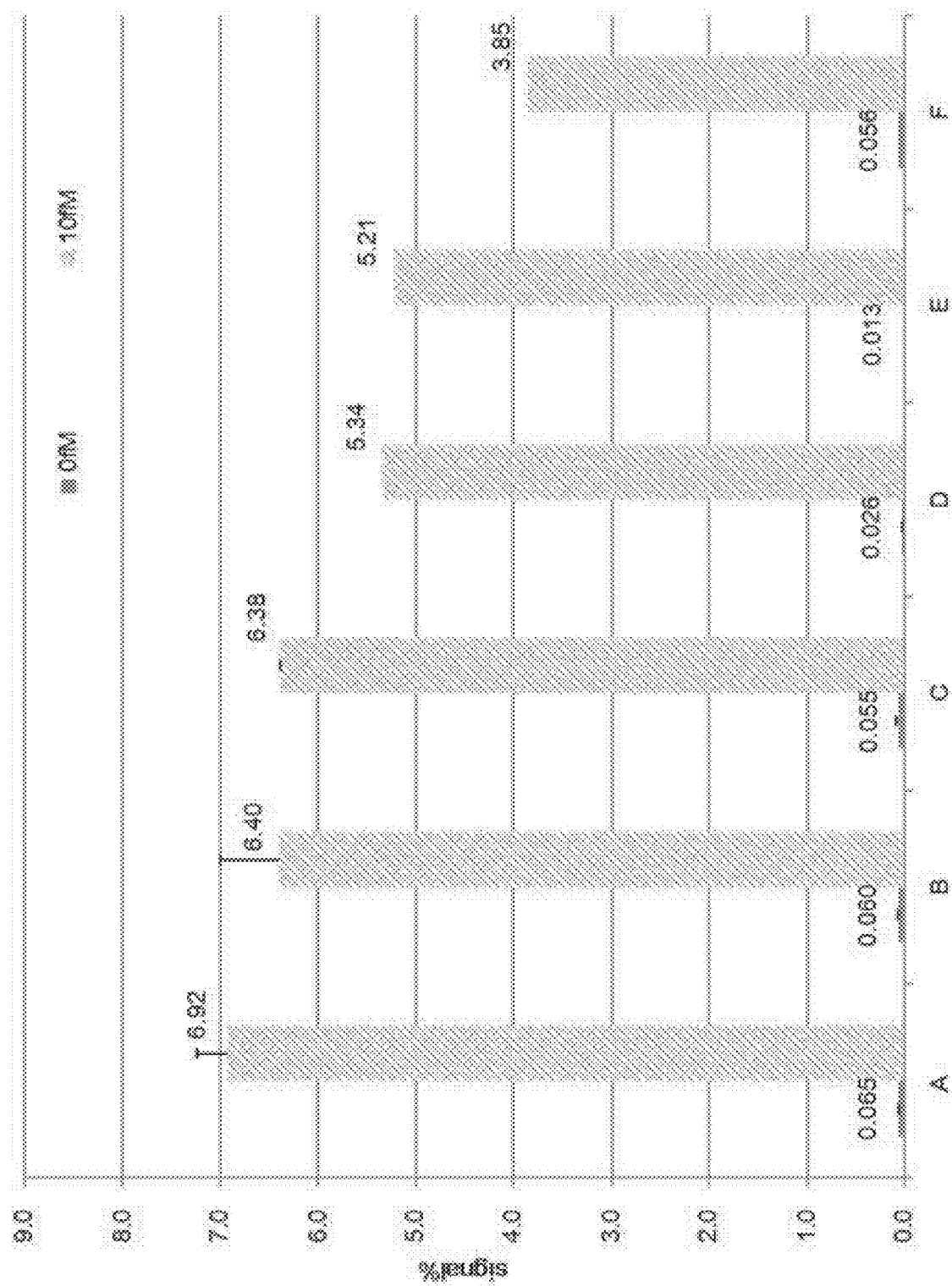
FIG. 8 shows the signal % (true signal) and S/N ratio of the "Black Ink Pre-Mix" study.

To solve the issue of the time consuming step of removing the aqueous phase, which can be incomplete, the "Black Ink Pre-Mix X" method was developed. As shown in FIG. 7A, the "Black Ink Pre-Mix" method involves the addition of black ink, such as India Ink, to the solution of the enzyme reaction before adding the enzyme reaction to the device well. The digital ELISA with the "Black Ink Pre-Mix" method (i.e., black ink was added to the substrate solution) showed an improved counting of the number of fluorescent droplets and increased analyzable images, as compared with the "Black Ink Addition" method. Table 2 shows the experimental conditions and the final concentration of black ink in each sample. The substrate for the assay was fluorescein-di-phosphate (FDP). The buffer for the enzymatic reaction was 1M diethanolamine (DEA), 1 mM $MgCl_2$, 0.05% Tween20, and 300 µM FDP, pH 9.25. As shown in FIG. 8, the signal % levels were almost same indicating that all images could be analyzed by the "Black Ink Pre-Mix" method with little or no affect on the detection of the true signal (Signal %).

TABLE 2

|   | Methods | Final Conc. Of Ink |
|---|---|---|
| A | Remove Aqueous Phase | 0% |
| B | ADDITION | 10% |
| C | PRE-MIX | 3.3% |
| D | | 6.7% |
| E | | 10% |
| F | | 13% |

For the sample treated with the "Black Ink Addition" method ("ADDITION"), some images could not be analyzed because the glow signal originated from the residual aqueous phase on the device side (bottom side of the device well). In the samples treated with the "Black Ink Pre-Mix" method, the glow of the fluorescence in the aqueous phase was suppressed no matter regardless of whether aqueous phase was present or not. Therefore, all images were analyzed completely because the glowed signal was eliminated by the black ink/substrate solution. Furthermore 3.3%, 6.7%, 10% of black ink with the "Black Ink Pre-Mix IX" method obtained similar results to the 10% result of the "Black Ink Addition" method (see FIG. 8). These result showed that black ink did not affect the enzyme reaction in the solution. In addition, the true signals could be observed even if the background was completely black.

Example 3

Other Dyes

Figure 10:
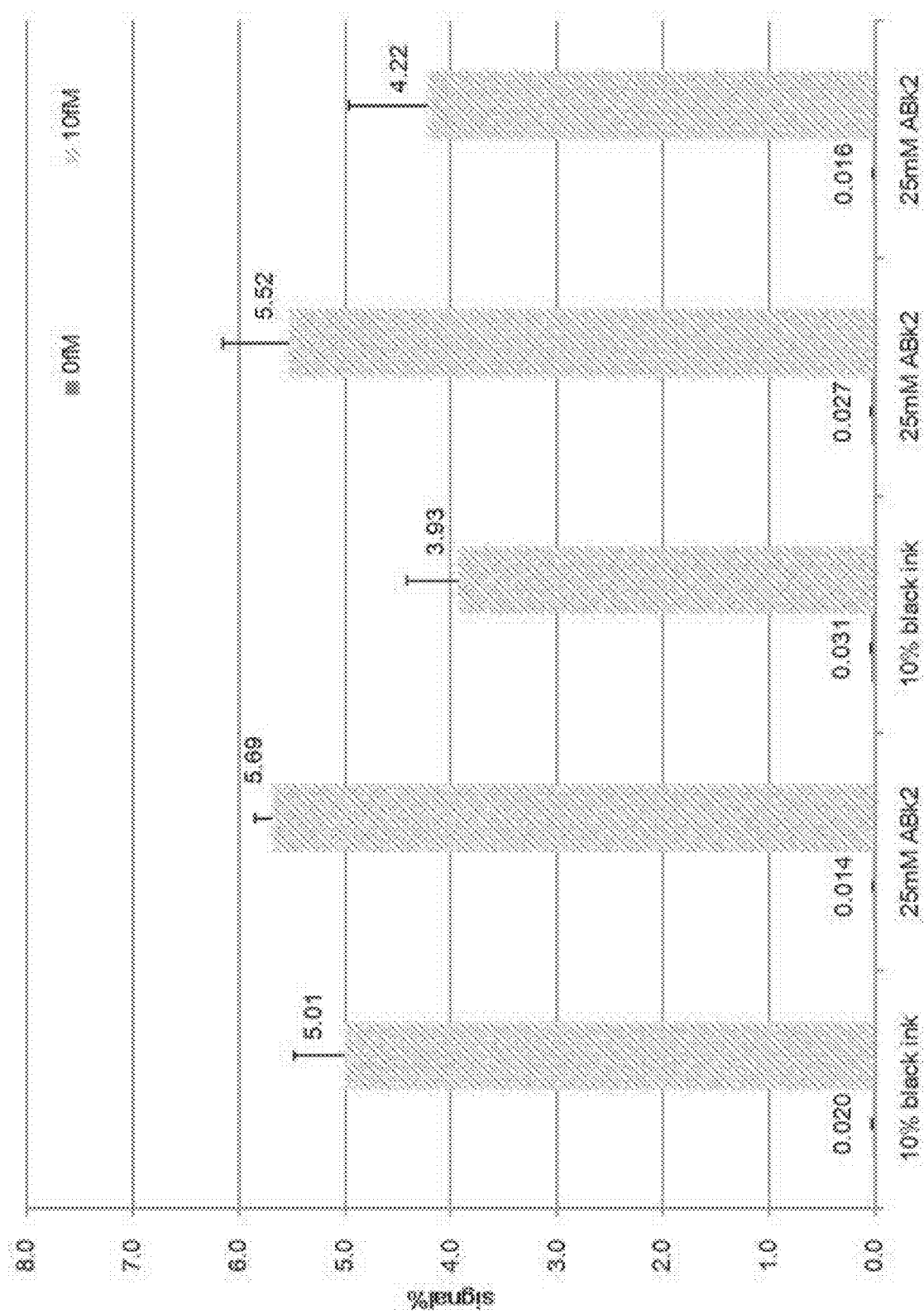
FIG. 10 shows the signal % (true signal) and S/N ratio of the dye compound pre-mix study.

Acid Black 2 ("ABk2"), another dye component, was used to reduce background glow noise in both "Black Ink Addition" and "Black Ink Pre-Mix" methods. 10% India Ink and 25 mM Acid Black 2 were compared and had similar images for signal detection with threshold optimization. See FIG. 10 and Table 3. When the images of the digital assay were analyzed, a bright spot was used as a threshold for detection. All pixels that made up an image had unique intensity values corresponding with the brightness. The dark pixels had lower values than bright pixels. A threshold was set to determine if a pixel was bright or dark (binarization). When using the black ink method, an appropriate threshold was different against previous assays, thus a new threshold was set ("threshold optimization"). Both India Ink ("Black Ink") and Acid Black 2 ("ABk2") effectively reduced the background fluorescence ("glow noise") using the "Black Ink Addition" or "Black Ink Pre-mix" method.

TABLE 3

|   | Method | Sample (Threshold) | Sample | Average % of Signal |
|---|---|---|---|---|
| A | Addition | 10% black ink (700/1000) | 0 fM | 0.020 |
|   |   |   | 10 fM | 5.008 |
| B |   | 25 mM ABk2 (700/1000) | 0 fM | 0.014 |
|   |   |   | 10 fM | 5.689 |
| C | Pre-Mix | 10% black ink (700/1000) | 0 fM | 0.031 |
|   |   |   | 10 fM | 3.929 |
| D |   | 25 mM ABk2 (1100/450) | 0 fM | 0.027 |
|   |   |   | 10 fM | 5.523 |
| E |   | 25 mM ABk2 (1100/500) | 0 fM | 0.016 |
|   |   |   | 10 fM | 4.222 |

Other dyes, Acid Orange 7 (AO7) and Direct Blue 14 (DBu14) (see FIGS. 9A and 9B), were combined and compared with black ink, i.e., ABk2. See Table 4 and FIG. 11. The combination of dyes reduced background glow noise in the "Black Ink Addition" or "Black Ink Pre-mix" method.

TABLE 4

|   | Method | Dye Additive | Sample | Average % of Signal | % CV |
|---|---|---|---|---|---|
| A | Addition | 10% black ink | 0 fM | 0.092 | 32.17 |
|   |   |   | 10 fM | 6.520 | 2.64 |
| B |   | 15 mM AO7 4 mM DBu14 | 0 fM | 0.113 | 12.69 |
|   |   |   | 10 fM | 6.492 | 4.77 |
| C | Pre-Mix | 10% black ink | 0 fM | 0.067 | 19.11 |
|   |   |   | 10 fM | 5.953 | 2.25 |
| D |   | 5 mM AO7 1 mM DBu14 | 0 fM | 0.070 | 21.40 |
|   |   |   | 10 fM | 5.78 | 2.36 |

Figure 11:
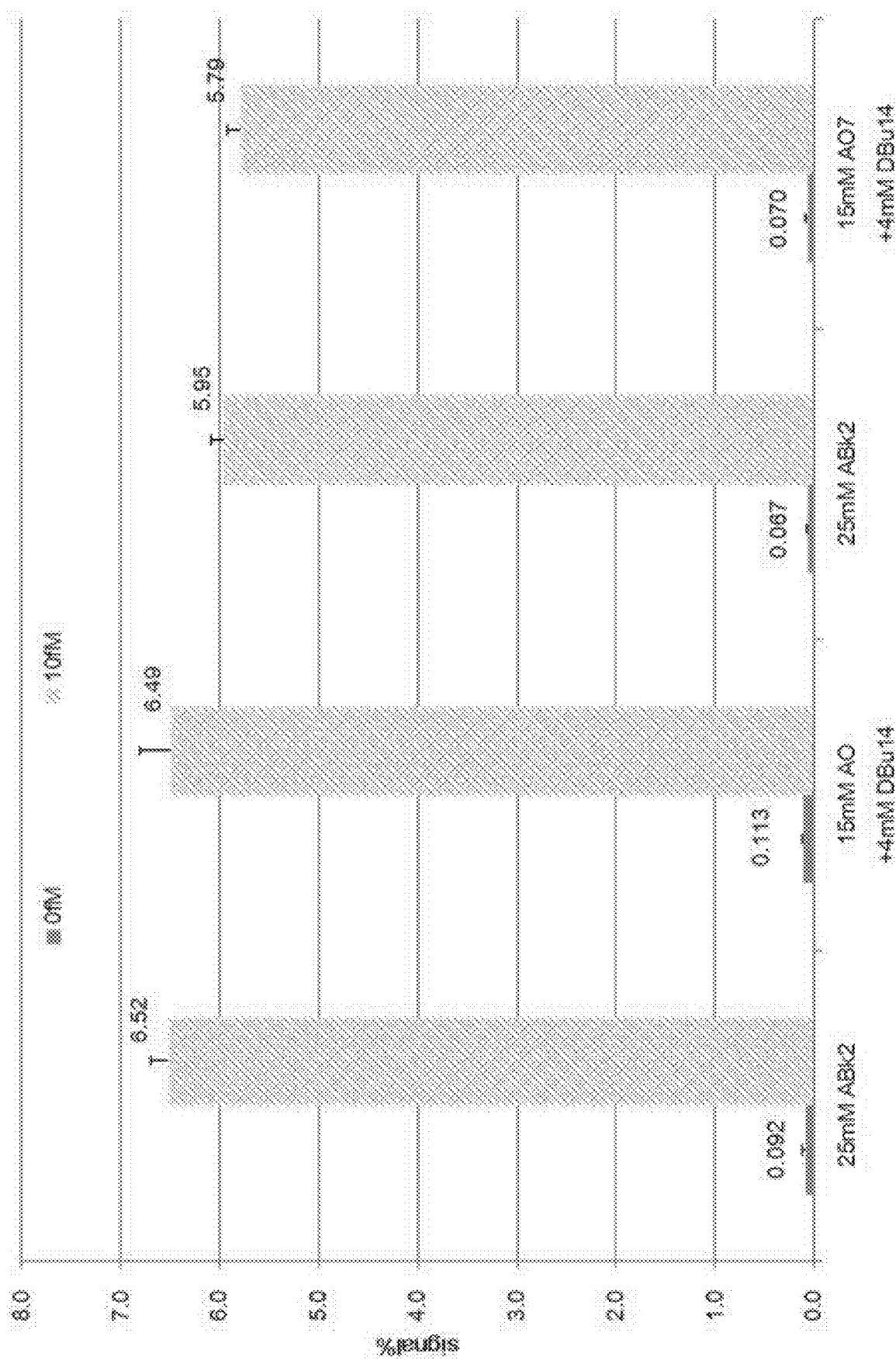
FIG. 11 shows the signal % (true signal) of the dye combination study. Black Ink: India Ink, ABk2: Acid Black 2, AO7: Acid Orange 7 and DBu14: Direct Blue 14.

The combination of 15 mM Acid Orange 7 (AO7) and 4 mM Direct Blue 14 (DBu14) reduced the background glow noise in the "Black Ink Addition." See FIG. 11. The combination of 5 mM AO7 and 1 mM DBu14 reduced the background glow noise in the "Black Ink Pre-Mix" method. Higher concentrations of AO7 and DBu14 (15 mM and 4 mM, respectively) with the "Black Ink Pre-Mix" method also reduced the background glow noise but the positive signal with 10 fM antigen was low.

Example 4

Detection of Low Concentration of Antigen

Figure 13:
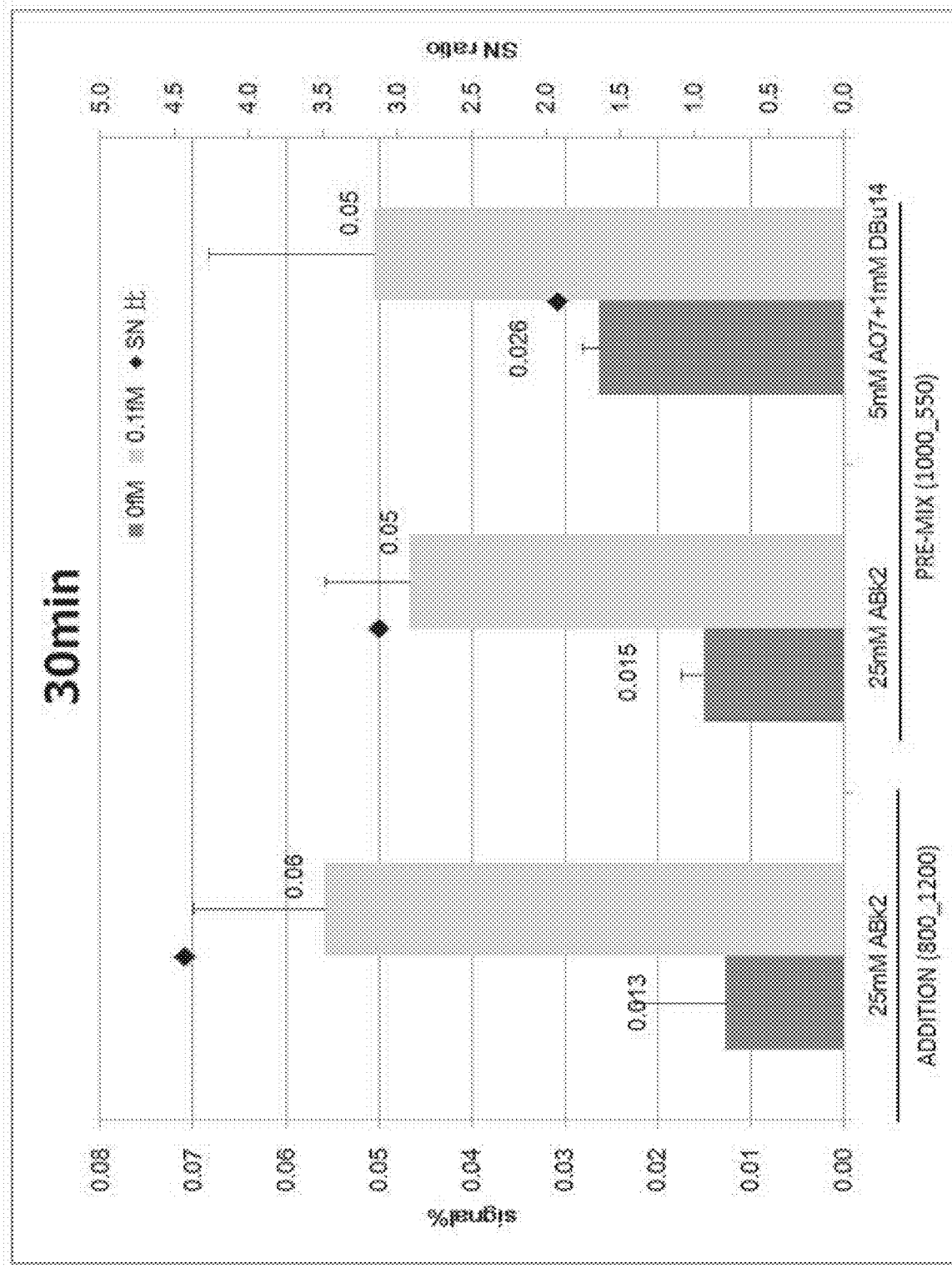
FIG. 13 shows the signal % (true signal) and S/N ratio of the improved fluorescent digital immunoassay, "Addition method" and "Pre-mix method," for the detection of low concentration of antigen (0.1 fM antigen sample) after 30 minutes. The antigen was recombinant hepatitis B surface antigen (rHBsAg).

The detection ability of the "Black Ink Addition" and "Black Ink Pre-Mix" methods were evaluated using a low concentration of antigen, 0.1 fM sample (see Table 5 and FIG. 13).

TABLE 5

|   | 0 fM | | 0.1 fM | | |
|---|---|---|---|---|---|
|   | % Signal | SD | % Signal | SD | S/N ratio |
| 25 mM ABk2 | 0.013 | 0.010 | 0.056 | 0.014 | 4.4 |
| 25 mM ABk2 | 0.015 | 0.002 | 0.047 | 0.009 | 3.1 |
| 5 mM AO7 + 1 mM DBu14 | 0.026 | 0.002 | 0.051 | 0.018 | 1.9 |

The signal to noise (S/N) ratios for the 0.1 fM sample detection were 4.4 for ABk2 using the "Black Ink Addition" method, 3.1 for ABk2 using the "Black Ink Pre-Mix MIX" method, and 1.9 for the combination of AO7 and DBu14 sing the "Black Ink Pre-Mix" method.

Example 5

Black Device

Figure 14:
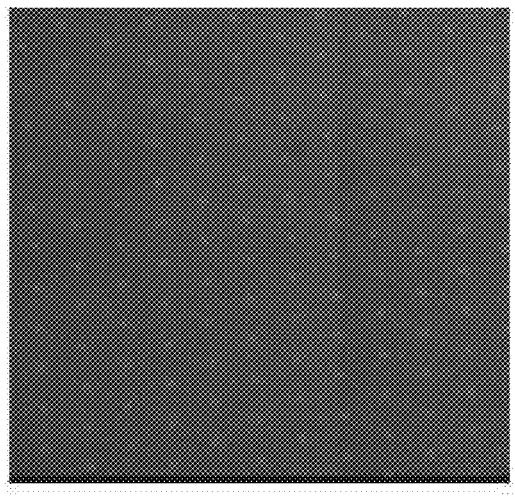
FIG. 14 shows an alternative embodiment for reducing background noise.
Figure 14:
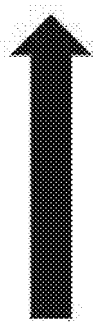
Figure 14:
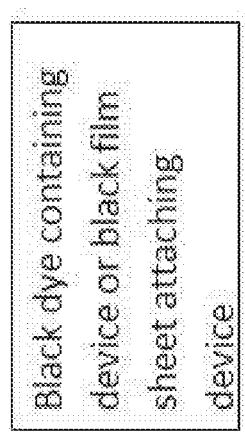
Figure 14:
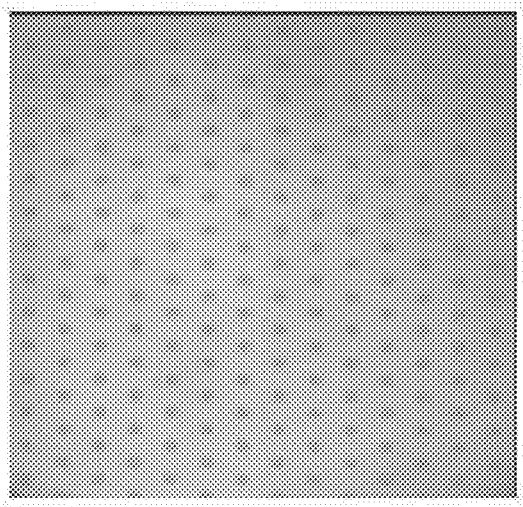

A "Black Device" can be prepared to reduce background glow noise (see FIG. 14) as an alternative to adding black ink to the digital assay. The left image of FIG. 14 shows the current device using a transparent prepared CYTOP on glass or COP, PDMS polymer. The right image of FIG. 14 shows the addition of black dye or material to the device, e.g. carbon black into CYTOP or polymer, or black film sheet attaching a transparent device for the background glow noise reduction.

Finally, although the various aspects and features of the invention have been described with respect to various embodiments and specific examples herein, all of which may be made or carried out conventionally, it will be understood that the invention is entitled to protection within the full scope of the appended claims.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

For reasons of completeness, various aspects of the invention are set out in the following numbered clause:

Clause 1. A signal-generating digital assay for determining the presence or absence of a single molecule of an analyte in a fluid sample, the method comprising: (a) contacting the fluid sample containing or suspected of containing the analyte with a plurality of solid supports to create a mixture, wherein each solid support comprises one or more first specific binding member capable of binding to the analyte thereby producing solid support-first specific binding member-analyte complexes; (b) washing the solid support-first specific binding member-analyte complexes in the mixture with a first wash buffer to remove any solid support-first specific binding member not bound to the analyte thereby producing a washed mixture; (c) adding to the washed mixture one or more second specific binding members capable of binding to the analyte thereby producing solid support-first specific binding member-analyte-second specific binding member complexes, wherein the second specific binding member comprises a signal generating compound attached thereto; (d) washing the solid support-first specific binding member-analyte-second specific binding member complexes with a second wash buffer to remove any second specific binding member not bound to the analyte bound to the first specific binding member thereby producing washed solid support complexes; (e) adding to the washed solid support complexes a signal generating substrate and a colorant, wherein the signal generating compound and the signal generating substrate produce a detectable signal; (f) spatially segregating at least a portion of the washed solid support complexes into a plurality of separate locations, wherein the plurality of separation locations comprises a plurality of reaction vessels and wherein the washed solid support complexes are present in an aqueous phase; (g) covering the plurality of reaction vessels with a sealant, wherein the aqueous phase is displaced by the sealant in the reaction chamber; and (h) detecting the presence or absence of the detectable signal using a digital counting device, wherein detection of the presence of the detectable signal indicates the presence of a single molecule of analyte in the sample.

Clause 2. The method of clause 1, wherein the signal-generating digital assay is a fluorescent digital immunoassay.

Clause 3. A fluorescent digital immunoassay for determining the presence or absence of a single molecule of an analyte in a fluid sample, the method comprising: (a) contacting the fluid sample containing or suspected of containing the analyte with a plurality of solid supports to create a mixture, wherein each solid support comprises one or more first specific binding member capable of binding to the analyte thereby producing solid support-first specific binding member-analyte complexes; (b) washing the solid support-first specific binding member-analyte complexes in the mixture with a first wash buffer to remove any solid support-first specific binding member not bound to the analyte thereby producing a washed mixture; (c) adding to the washed mixture one or more second specific binding members capable of binding to the analyte thereby producing solid support-first specific binding member-analyte-second specific binding member complexes, wherein the second specific binding member comprises a signal generating compound attached thereto; (d) washing the solid support-first specific binding member-analyte-second specific binding member complexes with a second wash buffer to remove any second specific binding member not bound to the analyte bound to the first specific binding member thereby producing washed solid support complexes; (e) adding to the washed solid support complexes a signal generating substrate and a colorant, wherein the signal generating compound and the signal generating substrate produce a detectable signal; (f) spatially segregating at least a portion of the washed solid support complexes into a plurality of separate locations, wherein the plurality of separation locations comprises a plurality of reaction vessels and wherein the washed solid support complexes are present in an aqueous phase; (g) covering the plurality of reaction vessels with a sealant, wherein the aqueous phase is displaced by the sealant in the reaction chamber; and (h) detecting the presence or absence of the detectable signal using a digital counting device, wherein detection of the presence of the detectable signal indicates the presence of a single molecule of analyte in the sample.

Clause 4. The method of any one of clauses 1 to 3, wherein the colorant is added simultaneously with the signal generating substrate.

Clause 5. The method of any one of clauses 1 to 3, wherein the colorant is added to the washed solid support complexes before the signal generating substrate.

Clause 6. The method of any one of clauses 1 to 3, wherein the colorant is added to the washed solid support complexes after the signal generating substrate.

Clause 7. A signal-generating digital assay for determining the presence or absence of a single molecule of an analyte in a fluid sample, the method comprising: (a) contacting the fluid sample containing or suspected of containing the analyte with a plurality of solid supports to create a mixture, wherein each solid support comprises one or more first specific binding member capable of binding to the analyte thereby producing solid support-first specific binding member-analyte complexes; (b) washing the solid support-first specific binding member-analyte complexes in the mixture with a first wash buffer to remove any solid support-first specific binding member not bound to the analyte thereby producing a washed mixture; (c) adding to the washed mixture one or more second specific binding members capable of binding to the analyte thereby producing solid support-first specific binding member-analyte-second specific binding member complexes, wherein the second specific binding member comprises a signal generating compound attached thereto; (d) washing the solid support-first specific binding member-analyte-second specific binding member complexes with a second wash buffer to remove any second specific binding member not bound to the analyte bound to the first specific binding member thereby producing washed solid support complexes; (e) adding to the washed solid support complexes a signal generating substrate, wherein the signal generating compound and the signal generating substrate produce a detectable signal; (f) spatially segregating at least a portion of the washed solid support complexes into a plurality of separate locations, wherein the plurality of separation locations comprises a plurality of reaction vessels and wherein the washed solid support complexes are present in an aqueous phase; (g)

covering the plurality of reaction vessels with a sealant, wherein the aqueous phase is displaced by the sealant in the reaction chamber; (h) adding a colorant to the displaced aqueous phase; and (i) detecting the presence or absence of the detectable signal using a digital counting device, wherein detection of the presence of the detectable signal indicates the presence of a single molecule of analyte in the sample.

Clause 8. A signal-generating digital assay for determining the presence or absence of a single molecule of an analyte in a fluid sample, the method comprising:

(a) contacting the fluid sample containing or suspected of containing the analyte with a plurality of solid supports to create a mixture, wherein each solid support comprises one or more first specific binding member capable of binding to the analyte thereby producing solid support-first specific binding member-analyte complexes; (b) washing the solid support-first specific binding member-analyte complexes in the mixture with a first wash buffer to remove any solid support-first specific binding member not bound to the analyte thereby producing a washed mixture; (c) adding to the washed mixture one or more second specific binding members capable of binding to the analyte thereby producing solid support-first specific binding member-analyte-second specific binding member complexes, wherein the second specific binding member comprises a signal generating compound attached thereto; (d) washing the solid support-first specific binding member-analyte-second specific binding member complexes with a second wash buffer to remove any second specific binding member not bound to the analyte bound to the first specific binding member thereby producing washed solid support complexes; (e) adding to the washed solid support complexes a signal generating substrate, wherein the signal generating compound and the signal generating substrate produce a detectable signal; (f) spatially segregating at least a portion of the washed solid support complexes into a plurality of separate locations, wherein the plurality of separation locations comprises a plurality of reaction vessels and wherein the washed solid support complexes are present in an aqueous phase; (g) covering the plurality of reaction vessels with a sealant, wherein the aqueous phase is displaced by the sealant in the reaction chamber; (h) adding a colorant to the sealant; and (i) detecting the presence or absence of the detectable signal using a digital counting device, wherein detection of the presence of the detectable signal indicates the presence of a single molecule of analyte in the sample.

Clause 9. The method of clause 7 or 8, wherein the signal-generating digital assay is a fluorescent digital immunoassay.

Clause 10. A fluorescent digital immunoassay for determining the presence or absence of a single molecule of an analyte in a fluid sample, the method comprising: (a) contacting the fluid sample containing or suspected of containing the analyte with a plurality of solid supports to create a mixture, wherein each solid support comprises one or more first specific binding member capable of binding to the analyte thereby producing solid support-first specific binding member-analyte complexes; (b) washing the solid support-first specific binding member-analyte complexes in the mixture with a first wash buffer to remove any solid support-first specific binding member not bound to the analyte thereby producing a washed mixture; (c) adding to the washed mixture one or more second specific binding members capable of binding to the analyte thereby producing solid support-first specific binding member-analyte-second specific binding member complexes, wherein the second specific binding member comprises a signal generating compound attached thereto; (d) washing the solid support-first specific binding member-analyte-second specific binding member complexes with a second wash buffer to remove any second specific binding member not bound to the analyte bound to the first specific binding member thereby producing washed solid support complexes; (e) adding to the washed solid support complexes a signal generating substrate, wherein the signal generating compound and the signal generating substrate produce a detectable signal; (f) spatially segregating at least a portion of the washed solid support complexes into a plurality of separate locations, wherein the plurality of separation locations comprises a plurality of reaction vessels and wherein the washed solid support complexes are present in an aqueous phase; (g) covering the plurality of reaction vessels with a sealant, wherein the aqueous phase is displaced by the sealant in the reaction chamber; (h) adding a colorant to the displaced aqueous phase; and (i) detecting the presence or absence of the detectable signal using a digital counting device, wherein detection of the presence of the detectable signal indicates the presence of a single molecule of analyte in the sample.

Clause 11. A fluorescent digital immunoassay for determining the presence or absence of a single molecule of an analyte in a fluid sample, the method comprising: (a) contacting the fluid sample containing or suspected of containing the analyte with a plurality of solid supports to create a mixture, wherein each solid support comprises one or more first specific binding member capable of binding to the analyte thereby producing solid support-first specific binding member-analyte complexes; (b) washing the solid support-first specific binding member-analyte complexes in the mixture with a first wash buffer to remove any solid support-first specific binding member not bound to the analyte thereby producing a washed mixture; (c) adding to the washed mixture one or more second specific binding members capable of binding to the analyte thereby producing solid support-first specific binding member-analyte-second specific binding member complexes, wherein the second specific binding member comprises a signal generating compound attached thereto; (d) washing the solid support-first specific binding member-analyte-second specific binding member complexes with a second wash buffer to remove any second specific binding member not bound to the analyte bound to the first specific binding member thereby producing washed solid support complexes; (e) adding to the washed solid support complexes a signal generating substrate, wherein the signal generating compound and the signal generating substrate produce a detectable signal; (f) spatially segregating at least a portion of the washed solid support complexes into a plurality of separate locations, wherein the plurality of separation locations comprises a plurality of reaction vessels and wherein the washed solid support complexes are present in an aqueous phase; (g) covering the plurality of reaction vessels with a sealant, wherein the aqueous phase is displaced by the sealant in the reaction chamber; (h) adding a colorant to the sealant; and (i) detecting the presence or absence of the detectable signal using a digital counting device, wherein detection of the presence of the detectable signal indicates the presence of a single molecule of analyte in the sample.

Clause 12. The method of any one of clauses 1 to 11, wherein the colorant is a black colorant.

Clause 13. The method of any one of clauses 1 to 12, wherein the colorant is a pigment-based composition.

Clause 14. The method of any one of clauses 1 to 13, wherein the colorant is one of India Ink, Acid Black 2, Acid Orange 7, Direct Blue 14, or a combination thereof.

Clause 15. The method of any one of clauses 2 to 6 and 9 to 14, wherein the fluorescent digital immunoassay has reduced background fluorescence.

Clause 16. The method of any one of clauses 1 to 15, wherein the one or more second specific binding members are added simultaneously or sequentially to the one or more first specific binding members.

Clause 17. The method of any one of clauses 1 to 16, wherein the signal generating compound is alkaline phosphatase or β-galactosidase.

Clause 18. The method of any one of clauses 1 to 17, wherein the signal generating substrate is a fluorescent substrate for the signal generating compound.

Clause 19. The method of any one of clauses 1 to 18, wherein the signal generating substrate is 4-methylumbelliferyl phosphate (MUP) or fluorescein diphosphate (FDP).

Clause 20. The method of any one of clauses 1 to 19, wherein the detectable signal is detected using a fluorescence microscope to acquire fluorescence images.

Clause 21. The method of any one of clauses 1 to 20, wherein the sealant has a density that is heavier than the aqueous phase.

Clause 22. The method of any one of clauses 1 to 21, wherein the sealant is an oil.

Clause 23. The method of clause 22, wherein the oil is a heavy fluorinated oil.

Clause 24. The method of clause 23, wherein the heavy fluorinated oil is FC-40.

Clause 25. The method of any one of clauses 1 to 24, wherein the plurality of reaction vessels is a nanowell array.

Clause 26. The method of any one of clauses 1 to 25, further comprising in step (e) an inhibitor of signal generating compound.

Clause 27. The method of clause 26, wherein the inhibitor is levamisole.

Clause 28. The method of any one of clauses 1 to 27, further comprising incubating the mixture for a period of time before adding to the mixture one or more second specific binding members or after adding to the mixture one or more second specific binding members, wherein the period of time is an incubation period and is about 40 minute to about 300 minutes.

Clause 29. The method of any one of clauses 1 to 28, wherein the fluid sample is serum, plasma or a whole blood sample.

Clause 30. The method of any one of clauses 1 to 29, further comprising contacting the fluid sample with one or more detergents, a surfactant, a nonpolar solvent, sonication, heating, or combination thereof, prior to contacting the fluid sample to the plurality of solid supports.

Clause 31. The method of any one of clauses 1 to 30, wherein the solid support is a magnetic solid support.

Clause 32. The method of any one of clauses 1 to 31, wherein the aqueous phase is displaced by the sealant in step (g) by tilting the plurality of reaction vessels.

Clause 33. A method of any one of clauses 1 to 32, wherein the analyte is a biological molecule.

Clause 34. The method of clause 33, wherein the biological molecule is a protein, a peptide, a DNA molecule, a RNA molecule, a sugar, or a lipid.

Clause 35. A method for reducing fluorescence background noise in a signal-generating digital assay used to detect an analyte in a sample, the method comprising: (a) contacting a fluid sample containing or suspected of containing the analyte with a plurality of solid supports to create a mixture, wherein each solid support comprises one or more first specific binding member capable of binding to the analyte thereby producing solid support-first specific binding member-analyte complexes; (b) washing the solid support-first specific binding member-analyte complexes in the mixture with a first wash buffer to remove any solid support-first specific binding member not bound to the analyte thereby producing a washed mixture; (c) adding to the washed mixture one or more second specific binding members capable of binding to the analyte thereby producing solid support-first specific binding member-analyte-second specific binding member complexes, wherein the second specific binding member comprises a signal generating compound attached thereto; (d) washing the solid support-first specific binding member-analyte-second specific binding member complexes with a second wash buffer to remove any second specific binding member not bound to the analyte bound to the first specific binding member thereby producing washed solid support complexes; (e) adding to the washed solid support complexes a signal generating substrate, wherein the signal generating compound and the signal generating substrate produce a detectable signal; (f) spatially segregating at least a portion of the washed solid support complexes into a plurality of separate locations, wherein the plurality of separation locations comprises a plurality of reaction vessels and wherein the washed solid support complexes are present in an aqueous phase; (g) covering the plurality of reaction vessels with a sealant, wherein the aqueous phase is displaced by the sealant in the reaction chamber; and (h) detecting the presence or absence of the detectable signal using a digital counting device, wherein detection of the presence of the detectable signal indicates the presence of a single molecule of analyte in the sample, wherein the digital counting device comprises a black device.

Clause 36. The method of clause 35, wherein the signal-generating digital assay is a fluorescent digital immunoassay.

Clause 37. A method for reducing fluorescence background noise in a fluorescent digital immunoassay used to detect an analyte in a sample, the method comprising: (a) contacting a fluid sample containing or suspected of containing the analyte with a plurality of solid supports to create a mixture, wherein each solid support comprises one or more first specific binding member capable of binding to the analyte thereby producing solid support-first specific binding member-analyte complexes; (b) washing the solid support-first specific binding member-analyte complexes in the mixture with a first wash buffer to remove any solid support-first specific binding member not bound to the analyte thereby producing a washed mixture; (c) adding to the washed mixture one or more second specific binding members capable of binding to the analyte thereby producing solid support-first specific binding member-analyte-second specific binding member complexes, wherein the second specific binding member comprises a signal generating compound attached thereto; (d) washing the solid support-first specific binding member-analyte-second specific binding member complexes with a second wash buffer to remove any second specific binding member not bound to the analyte bound to the first specific binding member thereby producing washed solid support complexes; (e) adding to the washed solid support complexes a signal generating substrate, wherein the signal generating compound and the signal generating substrate produce a detectable signal; (f) spatially segregating at least a portion of the washed solid support complexes into a plurality of separate locations, wherein the plurality of separation locations comprises a plurality of reaction vessels and wherein the washed solid support complexes are present in an aqueous phase; (g) covering the plurality of reaction vessels with a sealant, wherein the aqueous phase is displaced by the sealant in the reaction chamber; and (h) detecting the presence or absence of the detectable signal using a digital counting device, wherein detection of the presence of the detectable signal indicates the presence of a single molecule of analyte in the sample, wherein the digital counting device comprises a black device.

Clause 38. The method of any one of clauses 35 to 37, wherein the black device comprises a solid phase material comprising carbon black or a black film sheet attached to a transparent device.

Clause 39. The method of clause 38, wherein the solid phase material is CYTOP, cyclic olefin polymers (COP), or polydimethylsiloxane (PDMS).

Clause 40. The method of any one of clauses 35 to 39, further comprising adding a colorant to the washed solid support complexes simultaneously with the signal generating substrate, adding a colorant to the washed solid support complexes before the signal generating substrate, adding a colorant to the washed solid support complexes after the signal generating substrate, adding a colorant to the displaced aqueous phase, or adding a colorant to the sealant.

Clause 41. The method of clause 40, wherein the colorant is a pigment-based composition.

Clause 42. The method of clause 40 or 41, wherein the colorant is one of India Ink, Acid Black 2, Acid Orange 7, Direct Blue 14, or a combination thereof.

Clause 43. The method of clause 42, wherein the colorant is a combination of Acid Orange 7 and Direct Blue 14.

Clause 44. The method of any one of clauses 35 to 43, wherein the one or more second specific binding members are added simultaneously or sequentially to the one or more first specific binding members.

Clause 45. The method of any one of clauses 35 to 44, wherein the signal generating compound is alkaline phosphatase or β-galactosidase.

Clause 46. The method of any one of clauses 35 to 45, wherein the signal generating substrate is a fluorescent substrate for the signal generating compound.

Clause 47. The method of any one of clauses 35 to 46, wherein the signal generating substrate is 4-methylumbelliferyl phosphate (MUP) or fluorescein diphosphate (FDP).

Clause 48. The method of any one of clauses 35 to 47, wherein the detectable signal is detected using a fluorescence microscope to acquire fluorescence images.

Clause 49. The method of any one of clauses 35 to 48, wherein the sealant has a density that is heavier than the aqueous phase.

Clause 50. The method of any one of clauses 35 to 49, wherein the sealant is an oil.

Clause 51. The method of clause 50, wherein the oil is a heavy fluorinated oil.

Clause 52. The method of clause 51, wherein the heavy fluorinated oil is FC-40.

Clause 53. The method of any one of clauses 35 to 52, wherein the plurality of reaction vessels is a nanowell array.

Clause 54. The method of any one of clauses 35 to 53, further comprising in step (e) an inhibitor of signal generating compound.

Clause 55. The method of clause 54, wherein the inhibitor is levamisole.

Clause 56. The method of any one of clauses 35 to 55, further comprising incubating the mixture for a period of time before adding to the mixture one or more second specific binding members or after adding to the mixture one or more second specific binding members, wherein the period of time is an incubation period and is about 40 minute to about 300 minutes.

Clause 57. The method of any one of clauses 35 to 56, wherein the fluid sample is serum, plasma or a whole blood sample.

Clause 58. The method of any one of clauses 35 to 57, further comprising contacting the fluid sample with one or more detergents, a surfactant, a nonpolar solvent, sonication, heating, or combination thereof, prior to contacting the fluid sample to the plurality of solid supports.

Clause 59. The method of any one of clauses 35 to 58, wherein the solid support is a magnetic solid support.

Clause 60. The method of any one of clauses 35 to 59, wherein the aqueous phase is displaced by the sealant in step (g) by tilting the plurality of reaction vessels.

Clause 61. The method of any one of clauses 35 to 60, wherein the analyte is a biological molecule.

Clause 62. The method of clause 61, wherein the biological molecule is a protein, a peptide, a DNA molecule, a RNA molecule, a sugar, or a lipid.

Clause 63. The method of any one of clauses 36 to 62, wherein the fluorescent digital immunoassay includes a femto-liter droplet array.

What is claimed is:

1. A method for reducing fluorescence background noise in a signal-generating digital assay used to detect an analyte in a sample, the method comprising:
   (a) contacting a fluid sample containing or suspected of containing the analyte with a plurality of solid supports to create a mixture, wherein each solid support comprises one or more first specific binding member capable of binding to the analyte thereby producing solid support-first specific binding member-analyte complexes;
   (b) washing the solid support-first specific binding member-analyte complexes in the mixture with a first wash buffer to remove any solid support-first specific binding member not bound to the analyte thereby producing a washed mixture;
   (c) adding to the washed mixture one or more second specific binding members capable of binding to the analyte thereby producing solid support-first specific binding member-analyte-second specific binding member complexes, wherein the second specific binding member comprises a signal generating compound attached thereto;
   (d) washing the solid support-first specific binding member-analyte-second specific binding member complexes with a second wash buffer to remove any second specific binding member not bound to the analyte bound to the first specific binding member thereby producing washed solid support complexes;
   (e) adding to the washed solid support complexes a signal generating substrate, wherein the signal generating compound and the signal generating substrate produce a detectable signal;
   (f) spatially segregating at least a portion of the washed solid support complexes into a plurality of separate locations, wherein the plurality of separation locations comprises a plurality of reaction vessels and wherein the washed solid support complexes are present in an aqueous phase;

(g) covering the plurality of reaction vessels with a sealant, wherein the aqueous phase is displaced by the sealant in the reaction vessels, and wherein the aqueous phase is not removed from the reaction vessels; and (h) detecting the presence or absence of the detectable signal using a digital counting device, wherein detection of the presence of the detectable signal indicates the presence of a single molecule of analyte in the sample, wherein: the digital counting device comprises a black device; and the method comprises adding a colorant to: (1) the washed solid support complexes (i) simultaneously with the signal generating substrate; (ii) before the signal generating substrate; or (iii) after the signal generating substrate; (2) the displaced aqueous phase; or (3) to the sealant.

2. The method of claim 1, wherein the signal-generating digital assay is a fluorescent digital immunoassay.

3. A method for reducing fluorescence background noise in a fluorescent digital immunoassay used to detect an analyte in a sample, the method comprising:

(a) contacting a fluid sample containing or suspected of containing the analyte with a plurality of solid supports to create a mixture, wherein each solid support comprises one or more first specific binding member capable of binding to the analyte thereby producing solid support-first specific binding member-analyte complexes;

(b) washing the solid support-first specific binding member-analyte complexes in the mixture with a first wash buffer to remove any solid support-first specific binding member not bound to the analyte thereby producing a washed mixture;

(c) adding to the washed mixture one or more second specific binding members capable of binding to the analyte thereby producing solid support-first specific binding member-analyte-second specific binding member complexes, wherein the second specific binding member comprises a signal generating compound attached thereto;

(d) washing the solid support-first specific binding member-analyte-second specific binding member complexes with a second wash buffer to remove any second specific binding member not bound to the analyte bound to the first specific binding member thereby producing washed solid support complexes;

(e) adding to the washed solid support complexes a signal generating substrate, wherein the signal generating compound and the signal generating substrate produce a detectable signal;

(f) spatially segregating at least a portion of the washed solid support complexes into a plurality of separate locations, wherein the plurality of separation locations comprises a plurality of reaction vessels and wherein the washed solid support complexes are present in an aqueous phase;

(g) covering the plurality of reaction vessels with a sealant, wherein the aqueous phase is displaced by the sealant in the reaction vessels, and wherein the aqueous phase is not removed from the reaction vessels; and (h) detecting the presence or absence of the detectable signal using a digital counting device, wherein detection of the presence of the detectable signal indicates the presence of a single molecule of analyte in the sample, wherein: the digital counting device comprises a black device; and the method comprises adding a colorant to: (1) the washed solid support complexes (i) simultaneously with the signal generating substrate; (ii) before the signal generating substrate; or (iii) after the signal generating substrate; (2) the displaced aqueous phase; or (3) to the sealant.

4. The method of claim 1, wherein the black device comprises a solid phase material comprising carbon black or a black film sheet attached to a transparent device.

5. The method of claim 4, wherein the solid phase material is cyclic olefin polymers (COP), or polydimethylsiloxane (PDMS).

6. The method of claim 1, wherein the colorant is a pigment-based composition.

7. The method of claim 1, wherein the colorant is one of Chinese Ink, disodium; 4-amino-5-hydroxy-3-[(4-nitrophenyl)diazenyl]-6-phenyldiazenylnaphthalene-2,7-disulfonate, sodium; 4-[(2-hydroxynaphthalen-1-yl)diazenyl] benzenesulfonate, tetrasodium 3,3'-[(3,3'-dimethyl[1,1'-biphenyl]-4,4'-diyl)bis(azo)]bis[5-amino-4-hydroxynaphthalene-2,7-disulphonate], or a combination thereof.

8. The method of claim 7, wherein the colorant is a combination of sodium; 4-[(2-hydroxynaphthalen-1-yl)diazenyl]benzenesulfonate and tetrasodium 3,3'-[(3,3'-dimethyl [1,1'-biphenyl]-4,4'-diyl)bis(azo)]bis[5-amino-4-hydroxynaphthalene-2,7-disulphonate].

9. The method of claim 1, wherein the one or more second specific binding members are added simultaneously or sequentially to the one or more first specific binding members.

10. The method of claim 1, wherein the signal generating compound is alkaline phosphatase or β-galactosidase.

11. The method of claim 1, wherein the signal generating substrate is a fluorescent substrate for the signal generating compound.

12. The method of claim 1, wherein the signal generating substrate is 4-methylumbelliferyl phosphate (MUP) or fluorescein diphosphate (FDP).

13. The method of claim 1, wherein the detectable signal is detected using a fluorescence microscope to acquire fluorescence images.

14. The method of claim 1, wherein the sealant has a density that is heavier than the aqueous phase.

15. The method of claim 1, wherein the sealant is an oil.

16. The method of claim 15, wherein the oil is a heavy fluorinated oil.

17. The method of claim 16, wherein the heavy fluorinated oil is a perfluorocarbon.

18. The method of claim 1, wherein the plurality of reaction vessels is a nanowell array.

19. The method of claim 1, further comprising in step (e) adding an inhibitor of signal generating compound.

20. The method of claim 19, wherein the inhibitor is levamisole.

21. The method of claim 1, further comprising incubating the mixture for a period of time before adding to the mixture one or more second specific binding members or after adding to the mixture one or more second specific binding members, wherein the period of time is an incubation period and is about 40 minute to about 300 minutes.

22. The method of claim 1, wherein the fluid sample is serum, plasma or a whole blood sample.

23. The method of claim 1, further comprising contacting the fluid sample with one or more detergents, a surfactant, a nonpolar solvent, sonication, heating, or combination thereof, prior to contacting the fluid sample to the plurality of solid supports.

24. The method of claim 1, wherein the solid support is a magnetic solid support.

25. The method of claim 1, wherein the aqueous phase is displaced by the sealant in step (g) by tilting the plurality of reaction vessels.

26. The method of claim 1, wherein the analyte is a biological molecule.

27. The method of claim 26, wherein the biological molecule is a protein, a peptide, a DNA molecule, a RNA molecule, a sugar, or a lipid.

28. The method of claim 1, wherein the fluorescent digital immunoassay includes a femto-liter droplet array.

29. The method of claim 3, wherein the colorant is a pigment-based composition.

30. The method of claim 3, wherein the colorant is one of Chinese Ink, disodium; 4-amino-5-hydroxy-3-[(4-nitrophenyl)diazenyl]-6-phenyldiazenylnaphthalene-2,7-disulfonate, sodium; 4-[(2-hydroxynaphthalen-1-yl)diazenyl]benzenesulfonate, tetrasodium 3,3'-[(3,3'-dimethyl[1,1'-biphenyl]-4,4'-diyl)bis(azo)]bis[5-amino-4-hydroxynaphthalene-2,7-disulphonate], or a combination thereof.

31. The method of claim 30, wherein the colorant is a combination of sodium; 4-[(2-hydroxynaphthalen-1-yl)diazenyl]benzenesulfonate and tetrasodium 3,3'-[(3,3'-dimethyl[1,1'-biphenyl]-4,4'-diyl)bis(azo)]bis[5-amino-4-hydroxynaphthalene-2,7-disulphonate].

\* \* \* \* \*